US007875284B2

(12) United States Patent
Reyes et al.

(10) Patent No.: US 7,875,284 B2
(45) Date of Patent: Jan. 25, 2011

(54) METHODS OF MANUFACTURING AND MODIFYING TAXANE COATINGS FOR IMPLANTABLE MEDICAL DEVICES

(75) Inventors: Priscilla Reyes, Duncan, OK (US);
William F. Moore, Bloomington, IN (US); Randy Joe Myers, Bloomington, IN (US); Patrick H. Ruane, Hayward, CA (US); Melinda S. Morrell, Vienna, VA (US)

(73) Assignees: Cook Incorporated, Bloomington, IN (US); Med Institute, Inc., West Lafayette, IN (US)

( * ) Notice: Subject to any disclaimer, the term of this patent is extended or adjusted under 35 U.S.C. 154(b) by 581 days.

(21) Appl. No.: 11/823,283

(22) Filed: Jun. 27, 2007

(65) Prior Publication Data
US 2008/0020013 A1 Jan. 24, 2008

Related U.S. Application Data

(63) Continuation-in-part of application No. 11/715,975, filed on Mar. 8, 2007.

(60) Provisional application No. 60/781,264, filed on Mar. 10, 2006, provisional application No. 60/818,175, filed on Jun. 30, 2006, provisional application No. 60/830,726, filed on Jul. 13, 2006, provisional application No. 60/830,660, filed on Jul. 13, 2006.

(51) Int. Cl.
*A61F 2/00* (2006.01)
(52) U.S. Cl. ........................................ 424/423; 623/1.1
(58) Field of Classification Search .................. None
See application file for complete search history.

(56) References Cited

U.S. PATENT DOCUMENTS

| 4,739,762 | A | 4/1988 | Palmaz | 128/343 |
| 5,133,732 | A | 7/1992 | Wiktor | 606/195 |
| 5,292,331 | A | 3/1994 | Boneau | 606/198 |
| 5,380,299 | A | 1/1995 | Fearnot et al. | 604/265 |
| 5,421,955 | A | 6/1995 | Lau et al. | 216/48 |
| 5,440,056 | A | 8/1995 | Klein et al. | 549/510 |
| 5,609,629 | A | 3/1997 | Fearnot et al. | 623/1 |
| 5,824,049 | A | 10/1998 | Ragheb et al. | 623/1 |
| 5,873,904 | A | 2/1999 | Ragheb et al. | 623/1 |
| 6,090,127 | A | 7/2000 | Globerman | 606/194 |
| 6,096,070 | A | 8/2000 | Ragheb et al. | 623/1 |
| 6,221,153 | B1 | 4/2001 | Castor et al. | 117/11 |
| 6,299,604 | B1 | 10/2001 | Ragheb et al. | 604/265 |
| 6,306,166 | B1 | 10/2001 | Barry et al. | 623/1.46 |
| 6,530,951 | B1 | 3/2003 | Bates et al. | 623/1.45 |
| 6,589,546 | B2 | 7/2003 | Kamath et al. | 424/423 |
| 6,599,275 | B1 | 7/2003 | Fischer, Jr. | 604/265 |
| 6,689,802 | B2 | 2/2004 | DiMarco et al. | 514/365 |
| 6,730,064 | B2 | 5/2004 | Ragheb et al. | 604/265 |
| 6,774,278 | B1 | 8/2004 | Ragheb et al. | 623/11 |
| 6,858,644 | B2 | 2/2005 | Benigni et al. | 514/449 |
| 6,878,832 | B2 | 4/2005 | Saiji | 549/510 |
| 6,918,927 | B2 | 7/2005 | Bates et al. | 623/1.15 |
| 6,960,655 | B2 * | 11/2005 | Di Cintio et al. | 536/20 |
| 6,977,085 | B2 | 12/2005 | Werling et al. | 424/489 |
| 6,982,276 | B2 | 1/2006 | DiMarco et al. | 514/365 |
| 7,060,285 | B2 | 6/2006 | Muller | 424/400 |
| RE39,251 | E | 8/2006 | Guo | 514/365 |
| 7,153,879 | B2 | 12/2006 | DiMarco et al. | 514/365 |
| 2002/0142050 | A1 | 10/2002 | Straub et al. | 424/499 |
| 2003/0028243 | A1 | 2/2003 | Bates et al. | 623/1.15 |
| 2003/0028244 | A1 | 2/2003 | Bates et al. | 623/1.15 |
| 2003/0036794 | A1 | 2/2003 | Ragheb et al. | 623/1.15 |
| 2003/0144344 | A1 | 7/2003 | Benigni et al. | 514/449 |
| 2003/0236513 | A1 | 12/2003 | Schwarz et al. | 604/890.1 |
| 2004/0039441 | A1 | 2/2004 | Rowland et al. | 623/1.42 |
| 2004/0047909 | A1 | 3/2004 | Ragheb et al. | 424/471 |
| 2004/0063977 | A1 | 4/2004 | Saiji | 549/510 |
| 2004/0068241 | A1 | 4/2004 | Fischer, Jr. | 604/265 |
| 2004/0073284 | A1 | 4/2004 | Bates et al. | 623/1.11 |
| 2004/0243225 | A1 | 12/2004 | Ragheb et al. | 623/1.42 |

(Continued)

FOREIGN PATENT DOCUMENTS

EP 0 717 041 A1 6/1996

(Continued)

OTHER PUBLICATIONS

Kamath, K. R. et al. "The Taxus drug-eluting stent: A new paradigm in controlled delivery", Adv. Drug Delivery Reviews, vol. 58, No. 3, pp. 412-436 (2006).

(Continued)

*Primary Examiner*—Robert A Wax
*Assistant Examiner*—Bethany Barham
(74) *Attorney, Agent, or Firm*—Brinks Hofer Gilson & Lione

(57) ABSTRACT

This disclosure relates to endolumenal medical devices coated with a taxane therapeutic agent in one or more solid form(s) having varying dissolution rates. Particularly preferred coatings comprise amorphous paclitaxel, dihydrate paclitaxel, or combinations thereof that provide durable coatings that release paclitaxel over a desired period of time, which can be on the order of hours, days or weeks. Preferred embodiments relate to medical device coatings of paclitaxel, or paclitaxel analogs or derivatives, having one or more polymorph solid forms that provide a prolonged release of paclitaxel within a body vessel without requiring a polymer carrier or barrier layer to achieve the desired rate of paclitaxel elution.

20 Claims, 27 Drawing Sheets

U.S. PATENT DOCUMENTS

| | | | |
|---|---|---|---|
| 2006/0079526 A1 | 4/2006 | Wrasidlo et al. | 514/242 |
| 2006/0116420 A1 | 6/2006 | Chidambaram et al. | 514/449 |
| 2006/0204540 A1* | 9/2006 | Kuzma et al. | 424/423 |

FOREIGN PATENT DOCUMENTS

| | | |
|---|---|---|
| EP | 0734 721 A2 | 10/1996 |
| JP | 7-289630 | 11/1995 |
| WO | WO 93/10076 A1 | 5/1993 |
| WO | WO 00/32238 A1 | 6/2000 |
| WO | WO 03/006180 A1 | 1/2003 |

OTHER PUBLICATIONS

International Search Report for PCT/US2007/006223.

Jeong Hoon Lee, Un-Sook Gi, Jin-Hyun Kim, Yongae Kim, Hunseung Oh and Bumchan Min, "Preparation and Characterization of Solvent Induced Dihydrated, Anhydrous, and Amorphous Paclitaxel," *Bull. Korean Chem. Soc.*, 2001, vol. 22, No. 8, 925-928.

Richard T. Liggins, W.L. Hunter, and Helen M. Burt, "Solid-State Characterization of Paclitaxel," *Journal of Pharmaceutical Sciences*, vol. 86, No. 12, Dec. 1997, 1458-1463.

Anil K. Singla, Alka Garg, Deepika Aggarwal, "Paclitaxel and its formulations," *International Journal of Pharmaceutics*, 235 (2002) 179-192.

* cited by examiner

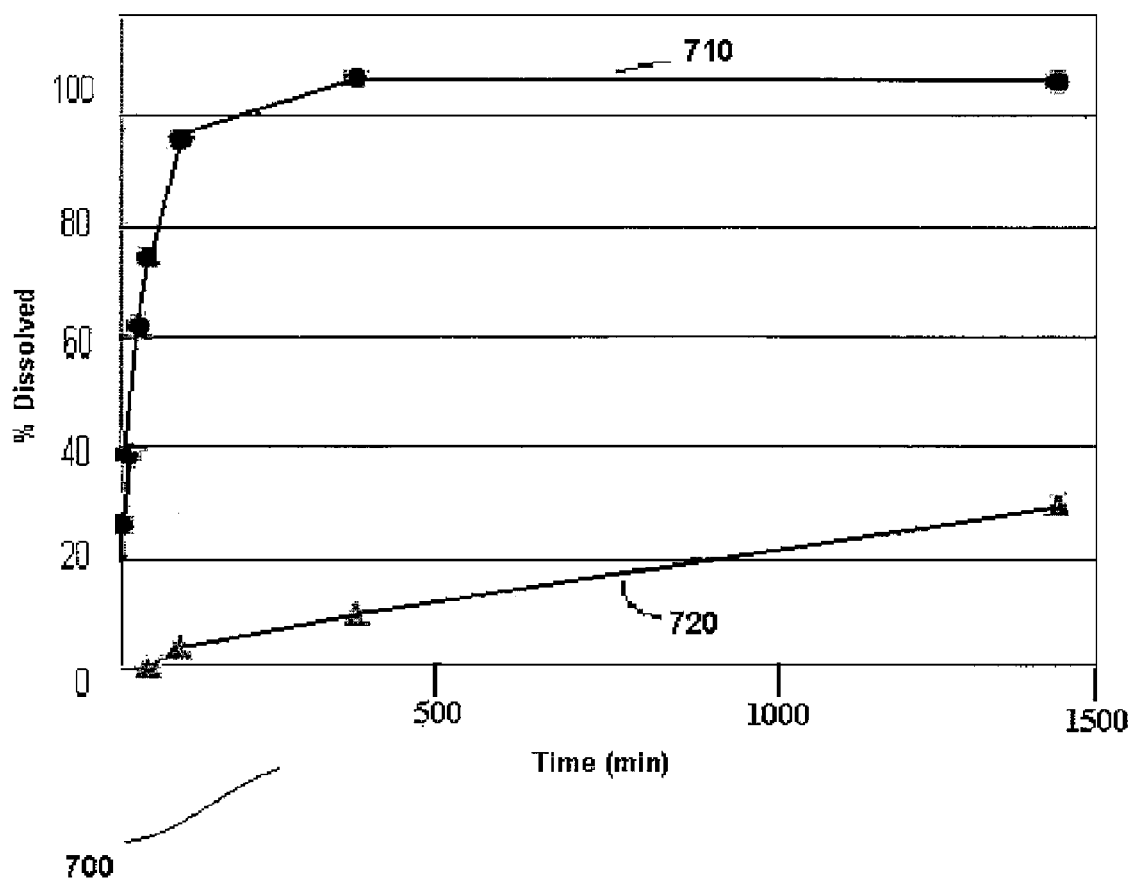

US 7,875,284 B2

METHODS OF MANUFACTURING AND MODIFYING TAXANE COATINGS FOR IMPLANTABLE MEDICAL DEVICES

RELATED APPLICATIONS

This application is a continuation-in-part of U.S. patent application Ser. No. 11/715,975, entitled "Taxane Coatings for Implantable Medical Devices" and filed Mar. 8, 2007, which claimed the benefit of U.S. Provisional Patent Application Ser. No. 60/781,264, entitled "Taxane Coatings for Implantable Medical Devices" and filed Mar. 10, 2006; this application also claims the benefit of the following U.S. Provisional Patent Applications: Ser. No. 60/818,175, entitled "Methods of Manufacturing Taxane Coatings for Endolumenal Medical Devices," and filed Jun. 30, 2006; Ser. No. 60/830,726, entitled "Controlled Release Taxane Coatings for Implantable Medical devices" and filed Jul. 13, 2006; and Ser. No. 60/830,660, entitled "Cyclodextrin Elution Media for Medical Device Coatings Comprising a Taxane Therapeutic Agent" and filed Jul. 13, 2006. Each of the above-referenced patent applications is incorporated herein by reference in their entirety.

TECHNICAL FIELD

The present disclosure relates to releasable taxane therapeutic agent coatings for endolumenal medical devices, including stents.

BACKGROUND

Delivery of a therapeutic agent from an endolumenal medical device can be desirable for a variety of applications. Therapeutic agents can be released from a medical device, such as an expandable stent or valve, to treat or mitigate undesirable conditions including restenosis, tumor formation or thrombosis. Procedures for mitigating certain conditions can include implantation of a device comprising a therapeutic agent. For example, the implantation of stents during angioplasty procedures has substantially advanced the treatment of occluded body vessels. Angioplasty procedures such as Percutaneous Transluminal Coronary Angioplasty (PTCA) can widen a narrowing or occlusion of a blood vessel by dilation with a balloon. Occasionally, angioplasty may be followed by an abrupt closure of the vessel or by a more gradual closure of the vessel, commonly known as restenosis. Acute closure may result from an elastic rebound of the vessel wall and/or by the deposition of blood platelets and fibrin along a damaged length of the newly opened blood vessel. In addition, restenosis may result from the natural healing reaction to the injury to the vessel wall (known as intimal hyperplasia), which can involve the migration and proliferation of medial smooth muscle cells that continues until the vessel is again occluded. To prevent such vessel occlusion, stents have been implanted within a body vessel. However, restenosis may still occur over the length of the stent and/or past the ends of the stent where the inward forces of the stenosis are unopposed. To reduce this problem, one or more therapeutic agents may be administered to the patient. For example, a therapeutic agent may be administered systemically, locally administered through a catheter positioned within the body vessel near the stent, or coated on the stent itself.

A medical device can be coated with a therapeutic agent in a manner suitable to expose tissue near the implantation site of the medical device to the therapeutic agent over a desired time interval, such as by releasing the therapeutic agent from an implanted stent into surrounding tissue inside a body vessel. Various approaches can be used to control the rate and dose of release of therapeutic agents from an endolumenal medical device. The design configuration of an implantable medical device can be adapted to influence the release of therapeutic from the device. A therapeutic agent can be included in the endolumenal medical device in various configurations. In some devices, the therapeutic agent is contained within an implantable frame or within a coating on the surface of the implantable frame. An implantable frame coating can include a bioabsorbable material mixed with a therapeutic agent, or coated over the therapeutic agent. Some endolumenal medical devices comprise an implantable frame with a porous biostable material mixed with or coated over a therapeutic agent. Endolumenal medical devices can also comprise a biostable material containing a dissolvable material and a therapeutic agent, where dissolution of the removable material upon implantation forms pores that release the therapeutic agent.

The design of a controlled release medical device can also depend on the desired mode of implantation of the device. The device can be adapted to the appropriate biological environment in which it is used. For example, a coated medical device for percutaneous transcatheter implantation can be sized and configured for implantation from the distal portion of a catheter, and adapted for expansion at the point of treatment within the body vessel by balloon or self-expansion. An endolumenal medical device can also be adapted to withstand a desired amount of flexion or impact, and should provide delivery of a therapeutic agent with a desired elution rate for a desired period of time.

Paclitaxel, and taxane analogues and derivatives thereof, can be used as a therapeutic agent coated on and released from implantable devices, such as stents, to mitigate or prevent restenosis. Paclitaxel is believed to disrupt mitosis (M-phase) by binding to tubulin to form abnormal mitotic spindles (i.e., a microtubule stabilizing agent).

Taxane therapeutic agent molecules having the same molecular structure may be arranged in different solid forms. Taxane therapeutic agent molecules can exist in solvated or non-solvated solid forms that can be characterized and differentiated by one or more physical properties, including the rate of dissolution in various elution media (e.g., cyclodextrin or porcine serum) prior to implantation. Typically, taxane therapeutic agents in a solvated solid form dissolve more slowly in blood than non-solvated solid forms, but are less durable than the non-solvated solid forms. Once dissolved, the taxane therapeutic agent molecules having identical molecular structures but originating from different solid forms are indistinguishable in solution. Solid forms of paclitaxel at room temperature include: amorphous paclitaxel ("aPTX"), dihydrate crystalline paclitaxel ("dPTX") and anhydrous crystalline paclitaxel. These different solid forms of paclitaxel can be characterized and identified using various solid-state analytical tools, for example as described by Jeong Hoon Lee et al., "Preparation and Characterization of Solvent Induced Dihydrate, Anhydrous and Amorphous Paclitaxel," *Bull. Korean Chem. Soc.* v. 22, no. 8, pp. 925-928 (2001), incorporated herein by reference in its entirety. For example, amorphous and dihydrate taxane solid forms may be readily identified and differentiated by visual appearance and elution rates. The dihydrate taxane solid form typically has an opaque white color, while the amorphous dihydrate taxane solid form typically has a clear transparent appearance. In addition, the presence of different solid forms of the taxane therapeutic agent in a medical device coating can be identified and quantified by contacting the coating with an elution medium that selectively dissolves one solid form more readily than a second solid form. In solution with an elution medium, such as porcine serum or blood, the presence of the taxane therapeutic agent can be identified, for example by using ultraviolet (UV) spectroscopy or high pressure liquid chromatography (HPLC). In certain elution media such as porcine serum, the solvated taxane therapeutic agent structures dissolve more slowly than the non-solvated solid forms. Non-solvated solid forms include amorphous or anhydrous solid forms.

U.S. Pat. No. 6,858,644, filed Nov. 26, 2002 by Benigni et al. ("Benigni"), teaches a crystalline solvate comprising paclitaxel and a solvent selected from the group consisting of dimethylsulfoxide, N,N'-dimethylformamide, N,N'-dimethylacetamide, N-methyl-2-pyrrolidone, 1,3-dimethyl-2-imidazolidinone, 1,3-dimethyl-3,4,5,6-tetrahydro-2-(1H)-pyrimidinone, and acetonitrile and combinations thereof. However, Benigni does not describe implantable device coatings comprising crystalline paclitaxel forms with different elution rates. Benigni discloses various solid forms of paclitaxel, including a first solid form reported as a highly water insoluble crystalline, granular, solvent-free form. The first solid form is substantially non-hygroscopic under normal laboratory conditions (relative humidity (RH) approximately 50-60%; 20-30° C.). However, when contacted with an atmosphere having a relative humidity greater than about 90%, or in aqueous suspensions, dispersions or emulsions, the first paclitaxel solid form reportedly converts (as a function of time, temperature, agitation, etc.) to a thermodynamically more stable second solid form. The second solid form is described as a trihydrate orthorhombic form having six water sites per two independent paclitaxel molecules (one paclitaxel "dimer"). These hydrated crystals reportedly present a fine, hair-like appearance and are even less water soluble than the first solid form. The second solid form is reportedly formed in aqueous suspensions or through crystallization from aqueous solvents in the presence of a large excess of water. This form is also disclosed in patent application EP 0 717 041, which describes the second solid form as being characterized by single crystal X-ray diffraction studies as being orthorhombic, with unit cells containing two crystallographically independent molecules of paclitaxel associated with hydrogen bonds to form a "dimer". Mastropaolo, et al. disclosed a crystalline solvate of paclitaxel obtained by evaporation of solvent from a solution of Taxol® in dioxane, water and xylene. Proc. Natl. Acad. Sci. USA 92, 6920-24 (July, 1995). This solvate is indicated as being unstable, and, in any event, has not been shown to effect purification of crude paclitaxel. The thin plate-like crystals are reported to contain five water molecules and three dioxane molecules per two molecules of paclitaxel. None of these references describe a durable taxane coating having an elution profile that can be altered by treatment of a medical device coating to vary the solid form composition of the coating.

There remains a need for intravascularly-implantable endolumenal medical devices comprising a coating of a releasable therapeutic agent having sufficient durability to resist the undesirable premature release of the therapeutic agent from the device prior to implantation at a point of treatment within a body vessel. For example, a coating comprising a releasable therapeutic agent is typically applied to an endolumenal medical device prior to crimping the medical device onto a delivery catheter. Coatings desirably have sufficient durability to withstand the crimping process with minimal loss of a therapeutic agent. Many medical device coatings adapted for controlled release of taxane therapeutic agent such as paclitaxel rely on a polymer that is applied in combination with the releasable therapeutic agent to both controls the release of the therapeutic agent from the medical device surface and to impart desired mechanical durability to the coating. For example, published U.S. patent application Ser. No. 10/213,126 (filed Aug. 5, 2002 and later published as US2004/0024448) discloses a stent coating comprising a releasable therapeutic agent combined with a fluoropolymer elastomeric to provide desirable mechanical properties such as good flexibility and durability. Similarly, U.S. patent application Ser. No. 10/662,877 (filed Sep. 16, 2004, and later published as US2004/0117007) discloses incorporation of polymers in a stent coating to "impart desirable properties of adhesion, cohesion, durability, and flexibility." Alternatively, medical device coatings comprising a dihydrate solvated taxane therapeutic agent such as dihydrate paclitaxel (paclitaxel-2H$_2$O) may provide a desired sustained release of paclitaxel in the absence of a polymer coating, but may lack a desired level of durability (See, e.g., Jeong Hoon Lee et al., "Preparation and Characterization of Solvent Induced Dihydrated, Anhydrous and Amorphous Paclitaxel," *Bull. Korean Chem. Soc.* v. 22, no. 8, pp. 925-928 (2001)). Other solid forms of taxane therapeutic agents, such as the amorphous solid form, provide more durable coatings but often provide for an undesirably rapid release of the taxane therapeutic agent upon implantation for certain applications.

In addition, existing packaging systems may not provide adequate protection of coatings of taxane therapeutic agents. Packaging systems for medical devices with taxane therapeutic agents may include a thermoform tray insert in a foil pouch, or a thermoform tray having a Tyvek® lid in a foil pouch, into which the coated medical device is vacuum sealed. Such conventional packaging for coated medical devices do not provide for regulation of ambient conditions such as circulation of air or exposure to light and oxygen. Without such appropriate regulation, the efficacy of the therapeutic agent coating maybe reduced.

What are needed are methods for treating medical device coatings that decrease the rate of post-implantation release of a taxane therapeutic agent without compromising a desired level of coating durability. For example, methods are needed to convert a highly durable but rapidly-eluting taxane therapeutic agent medical device coating to a less durable but slower-eluting taxane therapeutic medical device coating prior to implantation of the coated medical device in a patient. Such methods would permit the sale and transport of the highly durable medical device coating without undesirably compromising the physical quality of the coating, followed by the implantation of a medical device coating with a desirably longer period of elution within a body vessel. Without such methods, a trade-off exists between selecting coatings with a desired durability for packaging and transport, and desirably sustained elution of the taxane therapeutic agent upon implantation.

There is also a need for a medical device with a coating of a releasable therapeutic agent coating having sufficient durability to resist the undesirable premature release of the therapeutic agent from the device prior to implantation at a point of treatment within a body vessel.

Also needed are coating methods that provide a controlled release of a taxane therapeutic agent without requiring a polymer to provide a desired release rate. Preferably, an implanted medical device releases a therapeutic agent at the site of medical intervention to promote a therapeutically desirable outcome, such as mitigation of restenosis.

In addition, there is a need for sufficiently durable medical device coatings comprising or consisting of a sustained-release taxane therapeutic agent while being free from contact with non-biocompatible organic solvents.

Packaging adapted to maintain a taxane therapeutic agent is also needed. For example, packages adapted to provide a chamber in which a taxane therapeutic agent can be treated to decrease the elution rate of the coating are also needed.

In particular, there remains a need for intravascularly-implantable medical devices capable of releasing a taxane therapeutic agent at a desired rate and over a desired time period upon implantation, where the rate of release may be altered by treatment of the coating after deposition and preferably prior to implantation.

SUMMARY

The present disclosure relates to methods of manufacturing and treating therapeutic taxane coatings on medical devices. Preferred methods relate to a post-deposition treatment of medical device coatings including a taxane therapeutic agent in one or more solid forms so as to alter the durability and/or elution properties of the taxane therapeutic agent in the medical device coating. For example, the medical device coating may include paclitaxel in an amorphous solid form. Such treatments of deposited medical device coatings prior to implantation may alter the solid form of at least a portion of the taxane therapeutic agent, thereby changing the elution rate of the taxane therapeutic agent from the coating after implantation. Preferably, the methods comprise a conditioning step effective to decrease the elution rate of a coating consisting essentially of one or more taxane therapeutic agents in a medical device coating without undesirably compromising the durability of the coating. For example, the treatment may be a conditioning process that converts a portion of paclitaxel from an amorphous solid form to a hydrated solid form that is slower-eluting than the amorphous solid form.

The post-deposition treatment of a medical device coating comprising a taxane therapeutic agent, or "conditioning" of the coating, is performed to alter the solid form composition of taxane therapeutic agent in the coating. The coating may be treated after the initial coating and radial compression of the coated medical device. Typically, a higher durability coating may be required for crimping a radially expandable coated medical device, packaging and transport of the coated medical device. Where applicable, the post-deposition treatment conditioning step may occur after crimping of the coated medical device to minimize loss of the therapeutic agent from the coating. For example, the amorphous solid form of paclitaxel is more durable than the hydrated solid forms of paclitaxel. Accordingly, a medical device may be coated with paclitaxel in the amorphous solid form prior to radial compression (e.g., crimping of a stent) of the coated medical device. The radially compressed coated medical device may be subsequently treated by conditioning the coating in a manner effective to convert at least a fraction of the amorphous solid form to a hydrated solid form of paclitaxel. Optionally, conditioning may occur within packaging suitable for transport of the coated medical device to a medical service provider. During the conditioning step, a medical device coating comprising a taxane therapeutic agent is desirably maintained at an elevated humidity and temperature level (e.g, at least about 40%, more preferably about 80%, and at least 80° F.) for a time period (e.g., about 12 hours) effective to desirably alter the elution profile of the taxane therapeutic agent without undesirably compromising the durability of the coating during the implantation process. Typically, the conditioning step is performed prior to implantation to slow the rate of release of the taxane therapeutic agent from the coating after implantation. The conditioning of a medical device coating is preferably effective to alter the percentage of each solid form of a coated taxane therapeutic agent within the coating, thereby changing the durability of the coating and/or the elution profile of the taxane therapeutic agent from a medical device coating without including a polymer in the coating.

Preferably, the taxane therapeutic agent is paclitaxel, although any suitable paclitaxel analog or derivative can also be used. The medical device coating can have one or more of the taxane solid forms in coatings having a desired elution rate of the taxane therapeutic agent, while also having a desired durability and suitable level of surface uniformity.

Preferred methods of treating or manufacturing a medical device coating may include a conditioning step calibrated to desirably slow the release of the taxane therapeutic agent from the coating, without compromising the desired level of durability of the coating on the medical device. For example, a conditioning step may convert a fraction of the non-solvated taxane solid form, such as amorphous paclitaxel, in a medical device to a solvated taxane solid form, such as dihydrate paclitaxel. The amorphous paclitaxel solid form is more durable than the dihydrate paclitaxel solid form, but dissolves significantly more rapidly than the dihydrate paclitaxel solid form. As a result, the conditioning step may slow the rate of paclitaxel release from a taxane medical device coating upon implantation without undesirably compromising the durability of the coating as a result of the conditioning step. The conditioning step is desirably calibrated to avoid converting so much of the (more durable, faster eluting) amorphous paclitaxel solid form to the (less durable, slower eluting) dihydrate paclitaxel that the overall desired of coating durability is lost.

Coatings having undesirably low durability may readily flake or peel off during manipulation of the coating during subsequent manufacturing steps, such as loading of the coated medical device onto a delivery catheter, or during an implantation procedure. Solvated solid forms of taxane therapeutic agents, such as dihydrate paclitaxel, typically have desirably sustained elution rates, as exemplified by a solubility of less than about 40 wt % after 24 hours in porcine serum at 37° C., or having a solubility of less than 20% wt. after 1 hour in a 0.5% aqueous solution of Heptakis-(2,6-di-O-methyl)-β-cyclodextrin at 25° C. However, the solvated solid forms of taxane therapeutic agents, particularly coatings comprising greater than about 75 wt % of the solvated solid form, may have an undesirably low durability, as evidenced by an undesirably high percentage of coating weight reduction during the crimping process. The solvated taxane therapeutic agent solid form may be identified by a vibrational spectrum having at least three peaks between about 1735 $cm^{-1}$ and 1700 $cm^{-1}$, for example in a Raman or Infrared Spectrum.

In contrast, non-solvated solid forms of taxane therapeutic agents typically elute more rapidly, as evidenced by a solubility of greater than 50% after 24 hours in porcine serum at 37° C. or a solubility of greater than 50% wt. after 1 hour in a 0.5% aqueous solution of Heptakis-(2,6-di-O-methyl)-β-cyclodextrin at 25° C. However, non-solvated solid forms of taxane therapeutic agents may desirably be substantially more durable than solvated solid forms. The non-solvated taxane therapeutic agent solid forms include amorphous or anhydrous solid forms. The amorphous solid form of a therapeutic agent is characterized by a vibrational spectrum having a single broad peak between 1735 $cm^{-1}$ and 1700 $cm^{-1}$; the anhydrous solid form of a taxane therapeutic agent is characterized by two vibrational peaks between 1735 $cm^{-1}$ and 1700 $cm^{-1}$.

Preferably, the coating includes a taxane therapeutic agent in a layer that is free of a polymer that alters the release rate of the therapeutic agent. The entire medical device coating does not require a polymer to deliver the taxane therapeutic agent at a desired rate upon implantation, but instead includes the taxane therapeutic agent in one or more solid forms to provide the desired release rate. For instance, the coating may include a layer comprising the taxane therapeutic agent in one or more solid forms, the layer being at least substantially free of a polymer, containing less than about 0.10 micrograms of any polymer per $mm^2$ of abluminal surface area and preferably less than a total of 1 microgram of any polymer in the layer or in the entire coating. Accordingly, taxane therapeutic agent coatings with desirable elution rates can be obtained without including a polymer affecting the elution rate of the taxane therapeutic agent.

Therefore, in a first embodiment, methods of manufacture comprise the step of coating a medical device with a taxane therapeutic agent in a non-solvated solid form, followed by the step of conditioning the medical device coating to provide a coating comprising a higher fraction of the taxane therapeutic agent in a solvated solid form having a desirably slower elution rate compared to the non-solvated solid form. The conditioning step may be calibrated to prevent undesirably low durability coatings. The medical device may also be coated with a coating comprising a mixture of the solvated and non-solvated solid forms, followed by conditioning of the coating to increase the weight percentage of the solvated solid form in the coating.

Preferably, the medical device coating comprising the solvated solid taxane therapeutic agent solid form is maintained at a humidity level of 75% or higher during the conditioning step for a time period effective to increase the weight percentage of the solvated taxane therapeutic agent solid form. After conditioning, the coating preferably comprises a weight percentage of up to about 75% of the solvated solid form of the taxane therapeutic agent. The solvated solid taxane therapeutic agent is preferably a dihydrate solid form, most preferably dihydrate paclitaxel. The conditioned medical device coating also preferably comprises about 25% or more of the taxane therapeutic agent in the amorphous or anhydrous solid form.

Most preferably, the increase in the coating weight percentage of the solvated taxane therapeutic agent solid form during the conditioning step is substantially equal to a decrease in the coating weight percentage of the amorphous taxane therapeutic agent solid form during the conditioning step. The coating may be substantially free of a solvated solid form of the taxane therapeutic agent prior to the conditioning step, or the coating may comprise both the non-solvated solid forms and the solvated solid form of the taxane therapeutic agent prior to the conditioning step. For example, a coating may comprise less than about 1 wt % of the solvated taxane therapeutic agent solid form prior to conditioning, including a coating substantially free of the solvated taxane therapeutic agent solid form, and about 75 wt % of the solvated taxane therapeutic agent solid form after conditioning.

Preferably, conditioned coatings comprising a mixture of amorphous and dihydrate taxane therapeutic agent solid forms include an amount of amorphous taxane effective to impart a desired level of durability to the coating. Typically, conditioned coatings with at least about 5-10% amorphous taxane therapeutic agent solid form, and more preferably about 25% amorphous taxane therapeutic agent solid form, and have a desired level of durability to withstand a stent crimping and delivery procedures.

In one embodiment, a method of manufacturing a coated endolumenal medical device having at least one coated surface, the method includes the steps of: applying a taxane therapeutic agent to at least one surface of an endolumenal medical device to form a coating of the taxane therapeutic agent on at least one surface of the endolumenal medical device; carrying out one or more intermediate steps; and conditioning the taxane therapeutic agent coating, such that the resulting taxane therapeutic agent coating has a lower durability and a lower solubility than that of the coating prior to conditioning. The intermediate steps may include packaging of the medical device, radially compressing the medical device and/or a sterilization step. The conditioning step and the sterilization step may be performed as separate steps.

In another embodiment, kits including an endolumenal device having at least one surface coated with a taxane therapeutic agent and a package adapted to contain said device are provided. The kits may be characterized in that a therapeutic agent coating on the device may include a first solid form of a taxane therapeutic agent characterized by a vibrational spectrum having fewer than three peaks between 1735 and 1700 $cm^{-1}$ and a solubility of greater than 50% wt. after 24 hours in porcine serum at 37° C., and/or less than about 25% weight percentage of a second solid form of the taxane therapeutic agent characterized by a vibrational spectrum comprising at least three peaks between 1735 and 1700 $cm^{-1}$ and a solubility of less than 20% wt. after 24 hours in porcine serum at 37° C. Exposure of the device to a conditioning environment comprising a temperature of between 30 and 60° C. and a relative humidity of 75-100% for a time period of between 12-24 hours increases the weight percentage of said second solid form of the taxane therapeutic agent. The conditioning step preferably increase the fraction of the second solid form to greater than about 50%. The package may be adapted to enable the medical device while contained within the package to be exposed on demand to said conditioning environment. Optionally, the package configuration may be adapted to be changed to expose the medical device to said conditioning environment. Preferably, the package comprises a conditioning compartment containing a fluid, or adapted to be modified to admit a fluid (liquid and/or gas), such as water vapor. The endolumenal device may be radially compressed onto a delivery device prior to sealing in the package, such as crimping a coated vascular stent around a distal portion of a delivery catheter.

BRIEF DESCRIPTION OF THE DRAWINGS

FIG. 6A shows elution profiles for coatings of amorphous paclitaxel and solvated paclitaxel eluting in porcine serum.

DETAILED DESCRIPTION

Figure 1A:
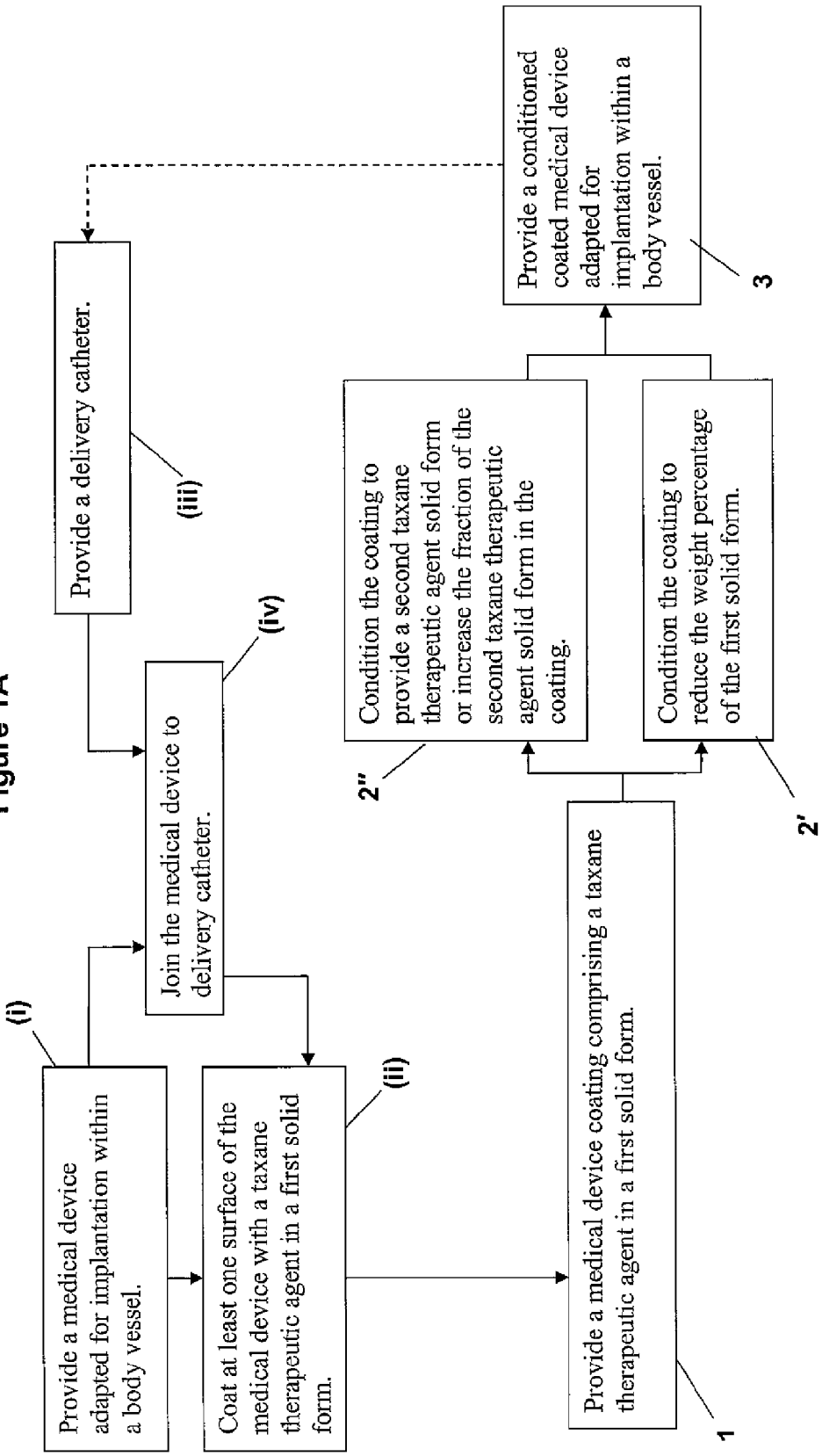
FIG. 1A is a schematic of preferred methods of manufacturing a medical device comprising a taxane therapeutic agent coating.

The present invention relates to medical device coatings that include a taxane therapeutic agent. Preferred compositions comprise one or more taxanes in one or more solid forms selected to provide desired properties of dissolution rate and/or durability. The coatings are preferably at least substantially free of a polymer, and may consist only of taxane therapeutic agent(s) in one or more solid forms. One particularly preferred taxane therapeutic agent is paclitaxel. Unless otherwise specified, description of paclitaxel coatings herein relate to a preferred embodiment of the taxane therapeutic agent, and is intended to be illustrative of all taxane therapeutic agents capable of forming two or more of the solid forms described, without limiting the scope of the therapeutic agent to paclitaxel.

Methods of manufacturing and treating coated medical devices comprising a releasable taxane therapeutic agent coating are provided. The methods preferably comprise the steps of depositing or providing a taxane therapeutic agent on a medical device in a first solid form in a coating, followed by conditioning the coating to provide a coating comprising a second solid form having desirable solubility and durability properties. The first solid form is preferably a non-solvated taxane therapeutic agent solid form having an undesirably high solubility in tissue but a desirable durability (such as an amorphous or anhydrous solid form of paclitaxel), while the second solid form is preferably a solvated taxane therapeutic agent solid form having a desirably lower solubility in tissue (such as the dihydrate solid form of paclitaxel).

In addition, the coating is preferably free of a polymer, or contains less than about 0.50 micrograms, 0.10 micrograms or 0.05 micrograms of a polymer per $mm^2$ of abluminal surface area and preferably less than 10 micrograms, 5 micrograms, 1 micrograms or 0.5 micrograms of a polymer total in the coating. Most preferably, the coating is free of a polymer, or contains less than about 0.50 micrograms, 0.10 micrograms or 0.05 micrograms of any polymer per $mm^2$ of abluminal surface area and preferably less than 10 micrograms, 5 micrograms, 1 micrograms or 0.5 micrograms of any polymer total in the coating.

The solvated and non-solvated solid forms of the taxane therapeutic agent differ in how the molecules of the therapeutic agent are arranged in the solid coating on the medical device, but preferably have identical molecular structures. Once dissolved, taxane therapeutic agent molecules originating from different solid forms are indistinguishable in solution or within the body. However, the taxane solid forms can have different rates of elution from the medical device, and different levels of durability. Medical device coatings described herein can provide for desired release rates of a taxane therapeutic agent depending on the solid form(s) of the therapeutic agent in the coating, and can have one or more layers. The taxane therapeutic agent coatings can provide controlled release of the taxane therapeutic agent from the medical device from coatings in the absence of a polymer carrier or barrier layer.

The conditioned coatings preferably comprise a taxane therapeutic agent with a desired level of durability for an intended use. Coatings consisting of dihydrate taxane therapeutic agents demonstrated a low durability, and a high propensity for dissociation from the stent coating upon crimping. In contrast, the amorphous solid form of the taxane therapeutic agents demonstrated greater durability and substantially lower tendency to dissociate from a coated stent upon crimping of the stent. In aqueous media such as porcine serum and blood, the amorphous taxane therapeutic agent solid form is typically more soluble than the dihydrate taxane therapeutic agent. Therefore, the release rate and the durability of the coating can be altered by incorporating a desired amount of dihydrate or amorphous solid forms of the taxane therapeutic agent in one or more coating layers. Preferred coatings comprise one or more durable layers comprising a suitable amount of an amorphous taxane therapeutic agent solid form to impart a desired durability to the coating. For example, after conditioning of the coating, the outer layer can comprise about 5, 10, 15, 20, 25% or more, of an amorphous taxane therapeutic agent to impart durability to a coating.

DEFINITIONS

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents and other references mentioned herein are incorporated by reference in their entirety. The materials, methods, and examples disclosed herein are illustrative only and not intended to be limiting.

The terms "absorption," "bioresorption" and "bioabsorption" can be used interchangeably to refer to the ability of the polymer or its degradation products to be removed by biological events, such as by fluid transport away from the site of implantation or by cellular activity (e.g., phagocytosis). The term "bioabsorbable" will generally be used in the following description to encompass resorbable, absorbable, bioresorbable, and biodegradable.

A "biocompatible" material is a material that is compatible with living tissue or a living system by not being undesirably toxic or injurious for an intended medical application.

The term "coating," as used herein and unless otherwise indicated, refers generally to material attached to a medical device. Preferably, the coating is a releasable therapeutic agent, such as a taxane therapeutic agent, adhered to at least one surface of an implantable medical device. A coating can include material covering any portion of a medical device, and can be configured as one or more coating layers. A coating can have a substantially constant or a varied thickness and composition. Coatings can be adhered to any portion of a medical device surface, including the luminal surface, the abluminal surface, or any portions or combinations thereof.

The term "coating layer," as used herein, refers to a stratified portion of a coating having a measurable composition distinguishable physically or chemically from an adjacent layer or material. Coating layers may be identified by one or more measurable properties (such as rate of elution, appearance, durability, infrared spectrum, crystal structure), and may be differentiated from an adjacent coating layer by at least one measurable property (e.g. different elution rates, chemical compositions, melting points, and the like). Coating layers are preferably substantially parallel and may be oriented parallel to a medical device surface. A coating layer material can be positioned in contact with the medical device surface, or in contact with other material(s) between the medical device surface and the coating layer material. A coating layer can cover any portion of the surface of a medical device, including material positioned in separate discrete portions of the medical device or as a continuous layer over an entire surface. Coatings and coating layers may also be at least partially confined within portions of a medical device, such as pores, holes of wells.

The recitation of "conditioning of a coating" refers to subjecting a coating to physical conditions effective to change the durability and/or solubility of the coating in an elution medium. The physical conditions of conditioning may include maintaining the coating at a specified temperature and/or humidity for a specified period of time. Alternatively, conditioning may include contacting the coating with a fluid, such as water or steam. The conditioning of a coating preferably provides a desired modification of physical properties, such as durability or elution rate, suitable for an intended use. For example, a coating comprising a paclitaxel taxane therapeutic agent as an amorphous paclitaxel solid form may be conditioned by maintaining the coating at a temperature and a relative humidity for a time period effective to provide a dihydrate paclitaxel solid form within the coating.

The phrase "controlled release" refers to an alteration of the rate of release of a therapeutic agent from a medical device coating in a given environment. A coating or configuration that alters the rate at which the therapeutic agent is released from a medical device provides for the controlled release of the therapeutic agent. A "sustained release" refers to prolonging the rate or duration of release of a therapeutic agent from a medical device. The rate of a controlled release of a therapeutic agent may be constant or vary with time. A controlled release may be described with respect to a drug elution profile, which shows the measured rate at which the therapeutic agent is removed from a drug-coated device in a given elution medium (e.g., a solvent) as a function of time. A controlled release elution profile may include, for example, an initial burst release associated with the introduction of the medical device into the physiological environment, followed by a more gradual subsequent release. A controlled release can also be a gradient release in which the concentration of the therapeutic agent released varies over time or a steady state release in which the therapeutic agent is released in equal amounts over a certain period of time (with or without an initial burst release).

The term "effective amount" refers to an amount of an active ingredient sufficient to achieve a desired affect without causing an undesirable side effect. In some cases, it may be necessary to achieve a balance between obtaining a desired effect and limiting the severity of an undesired effect. It will be appreciated that the amount of active ingredient used will vary depending upon the type of active ingredient and the intended use of the composition of the present invention.

The term "elution," as used herein, refers to removal of a material from a coating by contact with an elution medium. The elution medium can remove the material from the coating by any process, including by acting as a solvent with respect to the removable material. For example, in coated medical devices adapted for introduction to the vascular system, blood can act as an elution medium that dissolves a therapeutic agent releasably associated with a portion of the surface of the medical device. The therapeutic agent can be selected to have a desired solubility in a particular elution medium. Unless otherwise indicated, the term "release" referring to the removal of the therapeutic agent from a coating in contact with an elution medium is intended to be synonymous with the term "elution" as defined above. Similarly, an "elution profile" is intended to be synonymous with a "release profile," unless otherwise indicated.

An "elution medium," as used herein, refers to a material (e.g., a fluid) that removes a therapeutic agent from a coating upon contact of the coating with the elution medium for a desired period of time. A suitable elution medium is any substance or change in conditions (e.g., increased temperature, changing pH, and the like) causing the therapeutic agent to be released from the coating. The elution medium is desirably a fluid. More desirably, the elution medium is a biological fluid such as blood or porcine serum, although any other chemical substance can be used as an elution medium. For example, alternative elution media include phosphate buffered saline, an aqueous solution including a cyclodextrin such as Heptakis-(2,6-di-O-methyl)-β-cyclodextrin (HCD), Sodium Dodecyl Sulfate (SDS) and reaction conditions including elevated temperature and/or changes in pH, or combinations thereof, that release the therapeutic agent at a desired rate. Preferably, the elution medium is a fluid that provides an elution profile that is similar to the elution profile obtained upon implantation of the medical device within a body vessel and/or a desired time period for elution. For example, porcine serum can provide an elution profile that is similar to the elution profile in blood for some coating configurations.

A therapeutic agent is "enclosed" if the therapeutic agent is surrounded by the coating or other portions of the medical device, and does not form a portion of the surface area of the medical device prior to release of the therapeutic agent. When a medical device is initially placed in an elution medium, an enclosed therapeutic agent is preferably not initially in contact with the elution medium.

The term "hydrophobic," as used herein, refers to a substance with a solubility in water of less than 0.1 mg/mL at room temperature (about 25° C.).

The term "luminal surface," as used herein, refers to the portion of the surface area of a medical device defining at least a portion of an interior lumen. Conversely, the term "abluminal surface," as used herein, refers to portions of the surface area of a medical device that do not define at least a portion of an interior lumen. For example, where the medical device may be a vascular stent having a cylindrical frame formed from a plurality of interconnected struts and bends defining a cylindrical lumen, the abluminal surface can include the exterior surface, sides and edges of the struts and bends, while the luminal surface can include the interior surface of the struts and bends.

The term "interface," as used herein, refers to a common boundary between two structural elements, such as two coating layers in contact with each other.

The term "implantable" refers to an ability of a medical device to be positioned at a location within a body, such as within a body vessel. Furthermore, the terms "implantation" and "implanted" refer to the positioning of a medical device at a location within a body, such as within a body vessel.

The term "mixture" refers to a combination of two or more substances in which each substance retains its own chemical identity and properties.

A "non-bioabsorbable" or "biostable" material refers to a material, such as a polymer or copolymer, which remains in the body without substantial bioabsorption.

The term "pharmaceutically acceptable," as used herein, refers to those compounds of the present invention which are, within the scope of sound medical judgment, suitable for use in contact with the tissues of humans and lower mammals without undue toxicity, irritation, and allergic response, are commensurate with a reasonable benefit/risk ratio, and are effective for their intended use, as well as the zwitterionic forms, where possible, of the compounds of the invention.

As used herein, the term "polymorph" refers to a particular solid form of a taxane therapeutic agent, having particular physical properties such as X-ray diffraction, IR spectra, melting point, and the like. Polymorphs include solvate crystalline solid forms, amorphous solid forms and anhydrous solid forms of a taxane therapeutic agent. The polymorphs may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the polymorphs disclosed herein may exist as tautomers and both tautomeric forms are intended to be encompassed by the scope of the invention, even though only one tautomeric structure is depicted.

As used herein, the term "solid form" in reference to taxane molecules refers to an arrangement of molecules comprising a core taxane structure in the solid phase, including any polymorph or solvate crystal solid structure. Solid forms can include solvated crystalline forms comprising water molecules positioned between taxane molecules, non-crystalline amorphous taxane molecular arrangements or anhydrous taxane molecular arrangements substantially free of water molecules. Examples of solid forms of paclitaxel taxane molecules include anhydrous paclitaxel, amorphous paclitaxel and dihydrate paclitaxel.

As used herein, the phrase "therapeutic agent" refers to any implantable pharmaceutically active agent that results in an intended to provide a therapeutic effect on the body to treat or prevent conditions or diseases.

When naming substances that can exist in multiple enantiomeric forms, reference to the name of the substance without an enantiomeric designation, such as (d) or (l), refers herein to the genus of substances including the (d) form, the (l) form and the racemic mixture (e.g., d,l), unless otherwise specified. For example, recitation of "poly(lactic acid)," unless otherwise indicated, refers to a compound selected from the group consisting of: poly(L-lactic acid), poly(D-lactic acid) and poly(D,L-lactic acid). Similarly, generic reference to compounds that can exist in two or more polymorphs is understood to refer to the genus consisting of each individual polymorph species and any combinations or mixtures thereof.

As used herein, "derivative" refers to a chemically or biologically modified version of a chemical compound that is structurally similar to a parent compound and (actually or theoretically) derivable from that parent compound. A derivative may or may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). For example, a hydrogen may be substituted with a halogen, such as fluorine or chlorine, or a hydroxyl group (—OH) may be replaced with a carboxylic acid moiety (—COOH). The term "derivative" also includes conjugates, and prodrugs of a parent compound (i.e., chemically modified derivatives which can be converted into the original compound under physiological conditions). For example, the prodrug may be an inactive form of an active agent. Under physiological conditions, the prodrug may be converted into the active form of the compound. Prodrugs may be formed, for example, by replacing one or two hydrogen atoms on nitrogen atoms by an acyl group (acyl prodrugs) or a carbamate group (carbamate prodrugs). More detailed information relating to prodrugs is found, for example, in Fleisher et al., Advanced Drug Delivery Reviews 19 (1996) 115; Design of Prodrugs, H. Bundgaard (ed.), Elsevier, 1985; or H. Bundgaard, Drugs of the Future 16 (1991) 443. The term "derivative" is also used to describe all solvates, for example hydrates or adducts (e.g., adducts with alcohols), active metabolites, and salts of the parent compound. The type of salt that may be prepared depends on the nature of the moieties within the compound. For example, acidic groups, for example carboxylic acid groups, can form, for example, alkali metal salts or alkaline earth metal salts (e.g., sodium salts, potassium salts, magnesium salts and calcium salts, as well as salts with physiologically tolerable quaternary ammonium ions and acid addition salts with ammonia and physiologically tolerable organic amines such as, for example, triethylamine, ethanolamine or tris-(2-hydroxyethyl)amine). Basic groups can form acid addition salts, for example with inorganic acids such as hydrochloric acid, sulfuric acid or phosphoric acid, or with organic carboxylic acids and sulfonic acids such as acetic acid, citric acid, benzoic acid, maleic acid, fumaric acid, tartaric acid, methanesulfonic acid or p-toluenesulfonic acid. Compounds which simultaneously contain a basic group and an acidic group, for example a carboxyl group in addition to basic nitrogen atoms, can be present as zwitterions. Salts can be obtained by customary methods known to those skilled in the art, for example by combining a compound with an inorganic or organic acid or base in a solvent or diluent, or from other salts by cation exchange or anion exchange.

As used herein, "analog" or "analogue" refer to a chemical compound that is structurally similar to another but differs slightly in composition (as in the replacement of one atom by an atom of a different element or in the presence of a particular functional group), but may or may not be derivable from the parent compound. A "derivative" differs from an "analog" in that a parent compound may be the starting material to generate a "derivative," whereas the parent compound may not necessarily be used as the starting material to generate an "analogue."

Any concentration ranges, percentage range, or ratio range recited herein are to be understood to include concentrations, percentages or ratios of any integer within that range and fractions thereof, such as one tenth and one hundredth of an integer, unless otherwise indicated. Also, any number range recited herein relating to any physical feature, such as polymer subunits, size or thickness, are to be understood to include any integer within the recited range, unless otherwise indicated. It should be understood that the terms "a" and "an" as used above and elsewhere herein refer to "one or more" of the enumerated components. For example, "a" polymer refers to one polymer or a mixture comprising two or more polymers.

Taxane Therapeutic Agents

The present invention relates to methods of coating compositions comprising taxane therapeutic agents ("taxane"), such as paclitaxel. Taxanes in general, and paclitaxel in particular, are taxane therapeutic compounds considered to function as a cell cycle inhibitors by acting as an anti-microtubule agent, and more specifically as a stabilizer. As used herein, the term "paclitaxel" refers to a compound of the chemical structure shown as structure (1) below, consisting of a core structure with four fused rings ("core taxane structure," shaded in structure (1)), with several substituents.

(1)

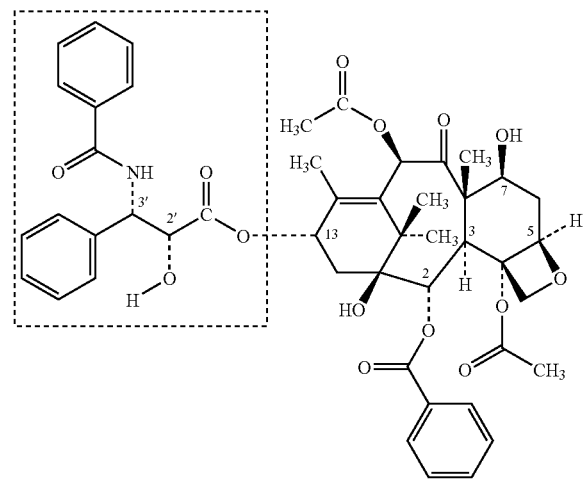

Other taxane analog or derivative compounds are characterized by variation of the paclitaxel structure (1). Preferred taxane analogs and derivatives core vary the substituents attached to the core taxane structure. In one embodiment, the therapeutic agent is a taxane analog or derivative including the core taxane structure (1) and the methyl 3-(benzamido)-2-hydroxy-3-phenylpropanoate moiety (shown in structure (2) below) at the 13-carbon position ("C13") of the core taxane structure (outlined with a dashed line in structure (1)).

(2)

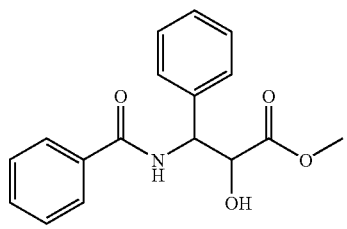

methyl 3-(benzamido)-2-hydroxy-3-phenylpropanoate

It is believed that structure (2) at the 13-carbon position of the core taxane structure plays a role in the biological activity of the molecule as a cell cycle inhibitor. Examples of therapeutic agents having structure (2) include paclitaxel (Merck Index entry 7117), docetaxol (TAXOTERE, Merck Index entry 3458), and 3'-desphenyl-3'-(4-nitrophenyl)-N-debenzoyl-N-(t-butoxycarbonyl)-10-deacetyltaxol.

Representative examples of paclitaxel derivatives or analogues that can be used as therapeutic agents include 7-deoxy-docetaxol, 7,8-cyclopropataxanes, N-substituted 2-azetidones, 6,7-epoxy paclitaxels, 6,7-modified paclitaxels, 10-desacetoxytaxol, 10-deacetyltaxol (from 10-deacetylbaccatin III), phosphonooxy and carbonate derivatives of taxol, taxol 2',7-di(sodium 1,2-benzenedicarboxylate, 10-desacetoxy-11,12-dihydrotaxol-10,12(18)-diene derivatives, 10-desacetoxytaxol, Protaxol (2'- and/or 7-O-ester derivatives), (2'- and/or 7-O-carbonate derivatives), asymmetric synthesis of taxol side chain, fluoro taxols, 9-deoxotaxane, (13-acetyl-9-deoxobaccatine III, 9-deoxotaxol, 7-deoxy-9-deoxotaxol, 10-desacetoxy-7-deoxy-9-deoxotaxol, derivatives containing hydrogen or acetyl group and a hydroxy and tert-butoxycarbonylamino, sulfonated 2'-acryloyltaxol and sulfonated 2'-O-acyl acid taxol derivatives, succinyltaxol, 2'-γ-aminobutyryltaxol formate, 2'-acetyl taxol, 7-acetyl taxol, 7-glycine carbamate taxol, 2'-OH-7-PEG (5000) carbamate taxol, 2'-benzoyl and 2',7-dibenzoyl taxol derivatives, other prodrugs (2'-acetyltaxol; 2',7-diacetyltaxol; 2'-succinyltaxol; 2'-(beta-alanyl)-taxol); 2'-gamma-aminobutyryltaxol formate; ethylene glycol derivatives of 2'-succinyltaxol; 2'-glutaryltaxol; 2'-(N,N-dimethylglycyl)taxol; 2'-(2-(N,N-dimethylamino)propionyl)taxol; 2'-orthocarboxybenzoyl taxol; 2'-aliphatic carboxylic acid derivatives of taxol, Prodrugs {2'-(N,N-diethylaminopropionyl)taxol, 2'-(N,N-diethylglycyl)taxol, 7-(N,N-dimethylglycyl)taxol, 2',7-di-(N,N-dimethylglycyl)taxol, 7-(N,N-diethylaminopropionyl) taxol, 2',7-di(N,N-diethylaminopropionyl)taxol, 2'-(L-glycyl)taxol, 7-(L-glycyl)taxol, 2',7-di(L-glycyl)taxol, 2'-(L-alanyl)taxol, 7-(L-alanyl)taxol, 2',7-di(L-alanyl)taxol, 2'-(L-leucyl)taxol, 7-(L-leucyl)taxol, 2',7-di(L-leucyl)taxol, 2'-(L-isoleucyl)taxol, 7-(L-isoleucyl)taxol, 2',7-di(L-isoleucyl) taxol, 2'-(L-valyl)taxol, 7-(L-valyl)taxol, 2'7-di(L-valyl) taxol, 2'-(L-phenylalanyl)taxol, 7-(L-phenylalanyl)taxol, 2',7-di(L-phenylalanyl)taxol, 2'-(L-prolyl)taxol, 7-(L-prolyl) taxol, 2',7-di(L-prolyl)taxol, 2'-(L-lysyl)taxol, 7-(L-lysyl) taxol, 2',7-di(L-lysyl)taxol, 2'-(L-glutamyl)taxol, 7-(L-glutamyl)taxol, 2',7-di(L-glutamyl)taxol, 2'-(L-arginyl) taxol, 7-(L-arginyl)taxol, 2',7-di(L-arginyl)taxol}, taxol analogues with modified phenylisoserine side chains, (N-debenzoyl-N-tert-(butoxycarbonyl)-10-deacetyltaxol, and taxanes (e.g., baccatin III, cephalomannine, 10-deacetylbaccatin III, brevifoliol, yunantaxusin and taxusin); and other taxane analogues and derivatives, including 14-beta-hydroxy-10 deacetybaccatin III, dibenzoyl-2-acyl paclitaxel derivatives, benzoate paclitaxel derivatives, phosphonooxy and carbonate paclitaxel derivatives, sulfonated 2'-acryloyltaxol; sulfonated 2'-O-acyl acid paclitaxel derivatives, 18-site-substituted paclitaxel derivatives, chlorinated paclitaxel analogues, C4 methoxy ether paclitaxel derivatives, sulfonamide taxane derivatives, brominated paclitaxel analogues, Girard taxane derivatives, nitrophenyl paclitaxel, 10-deacetylated substituted paclitaxel derivatives, 14-beta-hydroxy-10 deacetyl-baccatin III taxane derivatives, C7 taxane derivatives, C10 taxane derivatives, 2-debenzoyl-2-acyl taxane derivatives, 2-dibenzoyl and -2-acyl paclitaxel derivatives, taxane and baccatin III analogues bearing new C2 and C4 functional groups, n-acyl paclitaxel analogues, 10-deacetylbaccatin III and 7-protected-10-deacetylbaccatin III derivatives from 10-deacetyl taxol A, 10-deacetyl taxol B, and 10-deacetyl taxol, benzoate derivatives of taxol, 2-aroyl-4-acyl paclitaxel analogues, ortho-ester paclitaxel analogues, 2-aroyl-4-acyl paclitaxel analogues and 1-deoxy paclitaxel and 1-deoxy paclitaxel analogues.

A composition comprising a taxane compound can include formulations, prodrugs, analogues and derivatives of paclitaxel such as, for example, TAXOL (Bristol Myers Squibb, New York, N.Y.), docetaxel, 10-desacetyl analogues of paclitaxel and 3'-N-desbenzoyl-3'-N-t-butoxy carbonyl analogues of paclitaxel. Paclitaxel has a molecular weight of about 853 amu, and may be readily prepared utilizing techniques known to those skilled in the art (see, e.g., Schiff et al., Nature 277: 665-667, 1979; Long and Fairchild, Cancer Research 54: 4355-4361, 1994; Ringel and Horwitz, J. Nat'l Cancer Inst. 83 (4): 288-291, 1991; Pazdur et al., Cancer Treat. Rev. 19 (4): 351-386, 1993; WO 94/07882; WO 94/07881; WO 94/07880; WO 94/07876; WO 93/23555; WO 93/10076; WO94/00156; WO 93/24476; EP 590267; WO 94/20089; U.S. Pat. Nos. 5,294,637; 5,283,253; 5,279,949; 5,274,137; 5,202,448; 5,200,534; 5,229,529; 5,254,580; 5,412,092; 5,395,850; 5,380,751; 5,350,866; 4,857,653; 5,272,171; 5,411,984; 5,248,796; 5,248,796; 5,422,364; 5,300,638; 5,294,637; 5,362,831; 5,440,056; 4,814,470; 5,278,324; 5,352,805; 5,411,984; 5,059,699; 4,942,184; Tetrahedron Letters 35 (52): 9709-9712, 1994; J. Med. Chem. 35: 4230-4237, 1992; J. Med. Chem. 34: 992-998, 1991; and J. Natural Prod. 57 (10): 1404-1410, 1994; J. Natural Prod. 57 (11): 1580-1583, 1994; J. Am. Chem. Soc. 110: 6558-6560, 1988), or obtained from a variety of commercial sources, including for example, Sigma Chemical Co., St. Louis, Mo. (T7402—from *Taxus brevifolia*).

In one aspect, the therapeutic agent is selected from the taxane analogues and derivatives disclosed in U.S. Pat. No. 5,440,056 as having the structure (3):

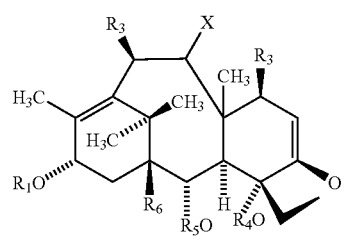

(3)

wherein X may be oxygen (paclitaxel), hydrogen (9-deoxy derivatives), thioacyl, or dihydroxyl precursors; $R_1$ is selected from paclitaxel or TAXOTERE side chains or alkanoyl of the formula (4):

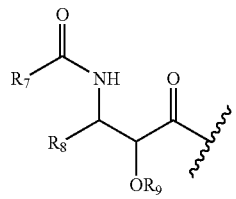

(4)

wherein $R_7$ is selected from hydrogen, alkyl, phenyl, alkoxy, amino, phenoxy (substituted or unsubstituted); $R_8$ is selected from hydrogen, alkyl, hydroxyalkyl, alkoxyalkyl, aminoalkyl, phenyl (substituted or unsubstituted), alpha or beta-naphthyl; and $R_9$ is selected from hydrogen, alkanoyl, substituted alkanoyl, and aminoalkanoyl; where substitutions refer to hydroxyl, sulfhydryl, alkoxyl, carboxyl, halogen, thioalkoxyl, N,N-dimethylamino, alkylamino, dialkylamino, nitro, and sulfate (—$OSO_3H$), and/or may refer to groups containing such substitutions; $R_2$ is selected from hydrogen or oxygen-containing groups, such as hydrogen, hydroxyl, alkoxyl, alkanoyloxy, aminoalkanoyloxy, and peptidyalkanoyloxy; $R_3$ is selected from hydrogen or oxygen-containing groups, such as hydrogen, hydroxyl, alkoxyl, alkanoyloxy, aminoalkanoyloxy, and peptidyalkanoyloxy, and may further be a silyl containing group or a sulphur containing group; $R_4$ is selected from acyl, alkyl, alkanoyl, aminoalkanoyl, peptidylalkanoyl and aroyl; $R_5$ is selected from acyl, alkyl, alkanoyl, aminoalkanoyl, peptidylalkanoyl and aroyl; $R_6$ is selected from hydrogen or oxygen-containing groups, such as hydrogen, hydroxyl alkoxyl, alkanoyloxy, aminoalkanoyloxy, and peptidyalkanoyloxy.

In one aspect, the therapeutic agent is selected from the paclitaxel analogues and derivatives disclosed in PCT International Patent Application No. WO 93/10076 as cell cycle inhibitors. The analogue or derivative may have a side chain attached to the taxane nucleus at C13, as shown in the structure below (formula 5), in order to confer antitumor activity to the taxane.

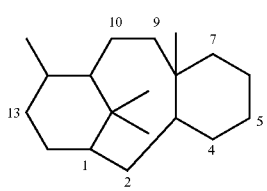

(5)

WO 93/10076 discloses that the taxane nucleus may be substituted at any position with the exception of the existing methyl groups. The substitutions may include, for example, hydrogen, alkanoyloxy, alkenoyloxy, aryloyloxy. In addition, oxo groups may be attached to carbons labeled 2, 4, 9, and/or 10. As well, an oxetane ring may be attached at carbons 4 and 5. As well, an oxirane ring may be attached to the carbon labeled 4. In one aspect, the taxane-based cell cycle inhibitor useful in the present invention is disclosed in U.S. Pat. No. 5,440,056, which discloses 9-deoxo taxanes. These are compounds lacking an oxo group at the carbon labeled 9 in the taxane structure shown above in formula (5). The taxane ring may also be substituted at the carbons labeled 1, 7 and 10 (independently) with H, OH, O—R, or O—CO—R where R is an alkyl or an aminoalkyl. As well, it may be substituted at carbons labeled 2 and 4 (independently) with aroyl, alkanoyl, aminoalkanoyl or alkyl groups. The side chain of formula (4) may be substituted at $R_7$ and $R_8$ (independently) with phenyl rings, substituted phenyl rings, linear alkanes/alkenes, and groups containing H, O or N. $R_9$ may be substituted with H, or a substituted or unsubstituted alkanoyl group.

Methods of Manufacturing Coated Medical Devices

FIG. 1A shows a schematic flow diagram of preferred methods of manufacturing a coated medical device comprising a taxane therapeutic agent having a desirable durability and elution profile. In a first embodiment, the methods of manufacturing preferably comprise step 1 of providing a medical device coating comprising a taxane therapeutic agent in a first solid form, followed by the step 2' of conditioning the coating to provide a second taxane therapeutic agent solid form and/or step 2" of conditioning the coating to reduce the weight percentage of the first solid form in the coating so as to provide a conditioned coated medical device in step 3.

A medical device coating comprising a taxane therapeutic agent may be provided according to step 1 by any suitable method or configuration. One suitable method of providing the coated medical device is shown schematically by steps (i) and (ii) in FIG. 1A. In step (i), any medical device adapted for implantation in a body vessel may be provided. Examples of suitable medical devices include vascular stents, stent grafts and drainage stents, including the specific medical devices described below. In step (ii), the medical device is coated on at least one surface with a taxane therapeutic agent by any suitable method, including the coating methods described below. The taxane therapeutic agent may be coated in a first solid form, which is preferably a non-solvated solid form having a desirable durability suitable to withstand processing steps prior to the conditioning process of steps 2' and/or 2". Methods of coating the medical device with a non-solvated solid form, including amorphous or anhydrous paclitaxel, as well as methods of identifying the solid form(s) present in a coating, include the methods provided below.

In a second embodiment, the methods of manufacturing a coated medical device further comprise steps of providing a delivery catheter according to step (iii) and joining the medical device to the delivery catheter according to step (iv). Any suitable delivery catheter may be provided according to step (iii), including a catheter comprising an expandable balloon. According to step (iv), the medical device may be joined to the delivery catheter by any suitable method, including crimping the medical device around the a portion of the delivery catheter.

Figure 1B:
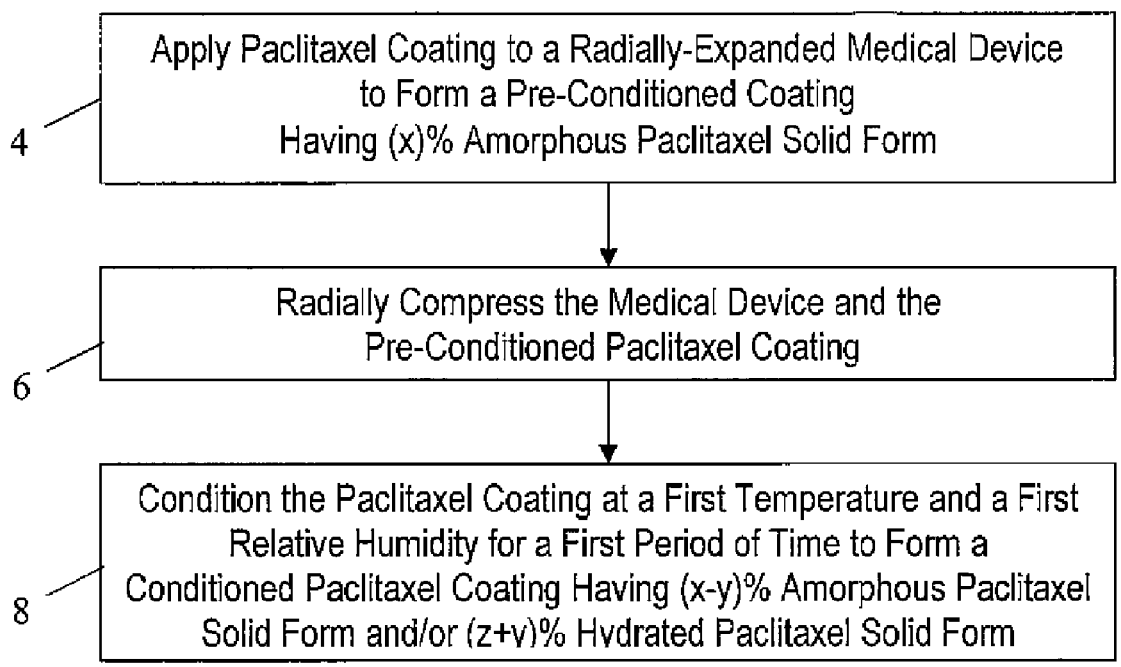
FIG. 1B is a schematic of an exemplary method of manufacturing a medical device comprising a taxane therapeutic agent coating.

FIG. 1B is a schematic of an exemplary method of manufacturing a medical device comprising a taxane therapeutic agent coating according to one aspect of the process illustrated by FIG. 1A. In the example of FIG. 1B, the medical device coating of step (1) in FIG. 1A is provided by performing the step of applying a paclitaxel coating (4) to a radially-expanded medical device to form a pre-conditioned coating having (x) % of the paclitaxel in an amorphous paclitaxel solid form (described below). The medical device may be, for example, a radially expandable vascular stent or a balloon portion of a catheter. The coating preferably consists essentially of paclitaxel, without other materials in amounts that alter the elution rate of the paclitaxel at an intended site of implantation within a body vessel. The paclitaxel coating may be applied by any suitable method, such as spray coating. The coating is preferably sufficiently durable, containing a minimum (x) % of the paclitaxel in an amorphous solid form to provide a desired level of durability. For instance, the coating preferably includes enough paclitaxel in the amorphous solid form to withstand radial compression (6) without losing an undesirable amount of the coating.

The pre-conditioned paclitaxel coated medical device is preferably radially compressed (6). The radial compression (6) may include crimping a vascular stent or deflating and folding a catheter balloon. Preferably, the medical device is radially compressed to a radial profile that is low enough to permit entry of the radially compressed medical device into a body vessel and translation therethrough to a site of implantation. For example, radial compression to an outer diameter of 6-10 French may be performed for most applications involving intralumenal insertion of the medical device through a blood vessel. The minimum percentage (x) % of amorphous paclitaxel may be, for example, at least about 20% by weight of the paclitaxel in the coating may be in the amorphous solid form.

In the next step (8) of the method illustrate in FIG. 1B, the radially-compressed coating is conditioned to decrease the amount of paclitaxel in the amorphous solid form and/or provide at least a portion of the coating having paclitaxel in a hydrated solid form (e.g., dihydrate paclitaxel). In one aspect, the radially-compressed coating is heated to a first temperature and a first relative humidity for a first period of time sufficient to convert a portion of the amorphous paclitaxel solid for to the hydrated paclitaxel solid form. This conversion may be described as converting a coating having (x) % amorphous paclitaxel to a conditioned coating having (x-y) % amorphous paclitaxel. The percentage (x) is typically about 25% or higher (e.g., 25-95%) and the percentage (y) is typically at least about 5% (e.g., 5-95%). Preferably, the paclitaxel coating has enough amorphous paclitaxel to impart a desired durability permitting the radial compression of the coated medical device (e.g., crimping or folding to about 6 French outer diameter) without losing more than 10% weight of the coating, preferably without losing more than 7%, 6% or 5% of the weight of the coating.

In addition, or in the alternative, hydrated paclitaxel may be formed during the conditioning process from a paclitaxel source other than the amorphous paclitaxel in the coating before conditioning (e.g., anhydrous paclitaxel in the coating or the additional deposition of paclitaxel during the conditioning process itself). In a paclitaxel coating having (z) % paclitaxel in solid forms other than the amorphous paclitaxel present in the coating prior to the conditioning step, the conditioning step may be described as producing a coating with (z+y) % of the coating in the hydrated paclitaxel solid form. The percentage (z) is typically at least about 5% (e.g., 5-95%).

The conditioning step (8) preferably includes maintaining the coating at a temperature and relative humidity level for a time sufficient to provide a hydrated paclitaxel solid form and/or to decrease the fraction of paclitaxel in the amorphous solid form. The temperature, humidity and time are selected to provide a conditioned coating with a desired rate of elution. By increasing the amount of paclitaxel in the hydrated solid form, both the durability and the elution rate of the coating is decreased. One example of a suitable conditioning step includes maintaining the paclitaxel coating at a first temperature of about 50° C., a first relative humidity of about 90% for a first time of at least about 12 hours. These conditioning conditions are believed to be effective to convert a paclitaxel coating having about 90% amorphous paclitaxel to a coating having about 25% amorphous paclitaxel and about 75% dihydrate. However, other temperatures, humidity levels and time intervals may also be used (described below).

Figure 2A:
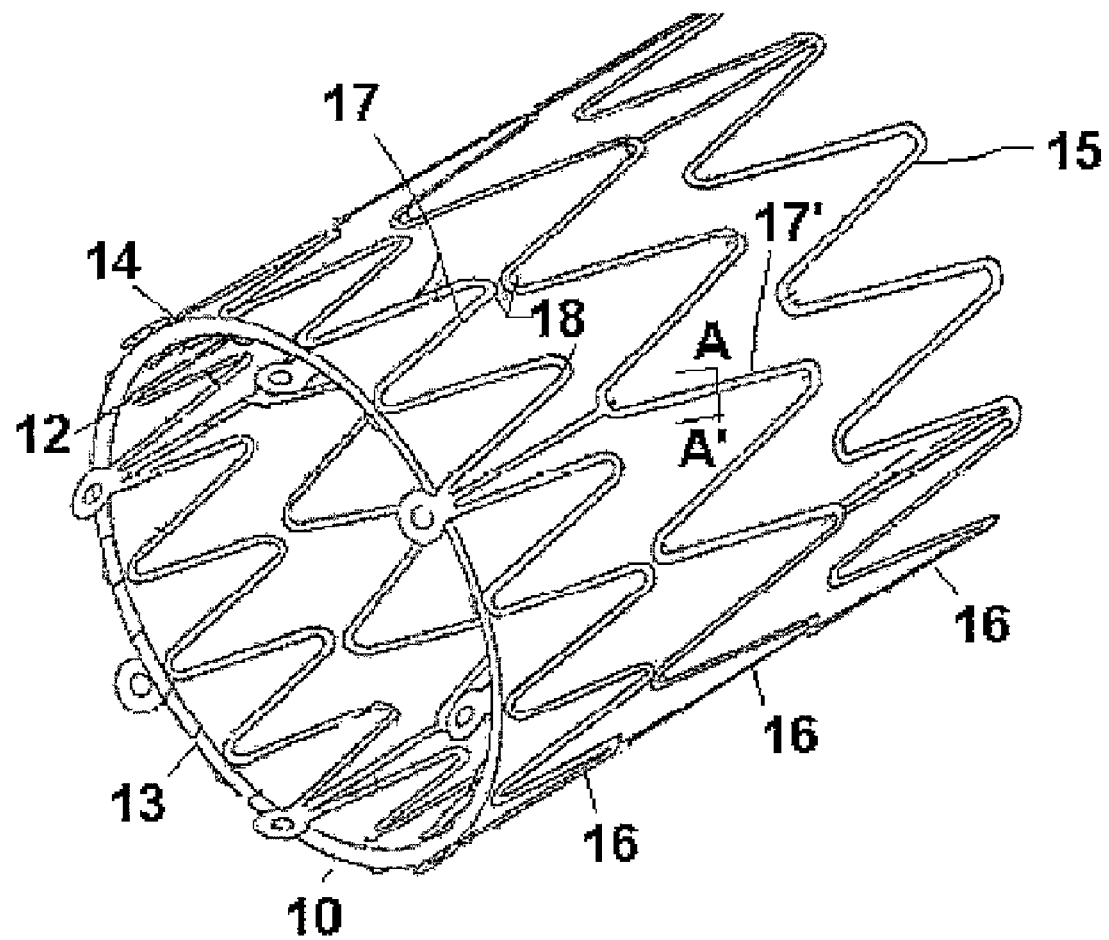
FIG. 2A shows a coated endolumenal medical device.

The coated medical device provided in step 1, or the uncoated medical device in step (i) of FIG. 1A (or the radially-expanded medical device recited in step (4) of FIG. 1B) is preferably a radially expandable vascular stent, such as the stent shown in FIG. 2A (although other devices such as catheter balloons may also be used). FIG. 2A shows a self-expanding vascular stent 10 having a luminal surface 12. The coated medical device provided in step 1 may further comprise a coating 37 applied to the abluminal surface 14 of the vascular stent 10. The vascular stent 10 extends from a proximal end 13 to a distal end 15. The vascular stent 10 has a tubular shape formed from a series of joined hoops 16 formed from interconnected struts 17 and bends 18, and defines the interior lumen.

Preferably, the conditioning step comprises maintaining a medical device comprising a taxane therapeutic agent in a first solid form under physical conditions of temperature, pressure or humidity effective to reduce the weight percentage of the first solid form (step 2'), conditions effective to provide a second solid form of the taxane therapeutic agent (step 2"), or a combination of step 2' and step 2" in combination or series. The first solid form is preferably more durable than the second solid form. For example, a non-conditioned coating having a higher percentage of the first solid form would typically lose a lower percentage of the coating weight during the crimping process than an otherwise comparable conditioned coating having a lower weight percentage of the first solid form. However, in this example, the conditioned coating would desirably elute more slowly within body vessel or in porcine serum, compared to the pre-conditioned coating. The conditioned coating would desirably maintain at least a minimum level of durability for an intended purpose. Preferably, the first solid form is a non-solvated solid form (such as amorphous paclitaxel) and the second solid form is a solvated solid form (such as dihydrate paclitaxel). In one aspect, the pre-conditioned coating provided in step 1 of FIG. 1A comprises both the first solid form and the second solid form of the taxane therapeutic agent, and the conditioning step preferably increases the weight percentage of the second solid form in the coating.

Specific parameters for the conditioning process can be varied to provide a decrease in the first solid form of the taxane therapeutic agent in the coating (step 2') or to provide (or increase) a second weight percentage of the second solid form of the taxane therapeutic agent in the coating (step 2"). Preferably, the conditioning process includes elevating the relative humidity to at least about 40%, and more preferably about 50%, 60%, 75%, 80%, 90%, 95% or 100% relative humidity. More preferably, the conditioning process includes maintaining a coating comprising a taxane therapeutic agent in a first solid form at a humidity of at least about 40%, a temperature of about 25-50° C. or higher and a pressure of about 1 atmosphere for a time period of about 5-12 hours, or longer. Preferably, these conditions of humidity and temperature are maintained for a period of about 10-24 hours, including periods of 12, 13, 14, 15 and 16 hours and most preferably about 12-15 hours. The conditioning process may also include variations on these parameters, such as higher humidity or temperature. The humidity during conditioning is preferably between about 40% and about 100%, most preferably about 75% to about 100%, and the temperature is preferably between about 30° C. and 50° C. or higher, most preferably between about 35° C. and about 50° C. Conditioning temperatures of 26.7° C. (80° F.) to 32.2° C. (90° F.), 28.9° C. (84° F.) to 30.6° C. (87° F.) and 29.4° C. (85° F.) to 30.6° C. (87° F.), including 30° C. (86° F.) may be used for forming a dihydrate paclitaxel solid form. Higher levels of relative humidity and longer time periods are preferred for lower temperatures in this range, such as 100% relative humidity with 26.7° C. (80° F.) for about 24 hours or about 90% relative humidity for 50° C. for 12 hours.

A coating may include one or more coating layers each comprising or consisting essentially of a taxane therapeutic agent in one or more solid forms. Preferred multilayer coatings include an outer layer comprising an amorphous solid form of a taxane therapeutic agent prior to conditioning to provide a highly durable outer surface. The outer layer preferably covers the exposed surface of the underlying coating layer(s). The outer layer can optionally include a mixture of other solid forms of the taxane therapeutic agent with the amorphous solid form. Multilayer coatings can include any number of coating layers beneath the outer coating, including 2, 3, 4, 5, 6, 7, and 8-layer coatings. One preferred two-layer coating configuration includes a first layer consisting essentially of a dihydrate paclitaxel solid form, and a second layer comprising an amorphous paclitaxel solid form. The second layer can be a mixture of the amorphous and the dihydrate solid forms of paclitaxel. After conditioning, the outer layer preferably includes a solvated solid form, such as dihydrate paclitaxel.

Figure 2B:
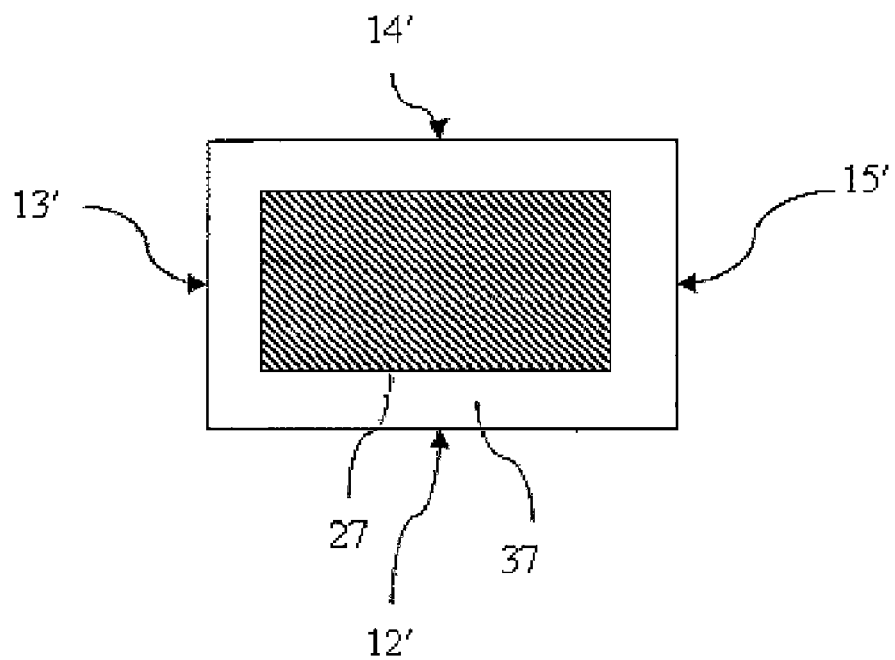
FIG. 2B shows a cross sectional view of a portion of the medical device of FIG. 1A prior to conditioning of the coating.

The unconditioned coated medical device provided in step 1 or the conditioned coated medical device provided in step 3 may have various coating configurations, including the configuration shown in FIG. 2B. FIG. 2B shows a cross section along line A-A' of an unconditioned, coated strut 17' from the vascular stent 10 shown in FIG. 2A. The coating 37 shown in FIG. 2B is described after the coating step (ii) (i.e., during step 1 in FIG. 1A) and before the conditioning step(s) (2') and/or (2") in FIG. 1A. Referring to FIG. 2B, the strut 17' can have any suitable cross sectional configuration, such as a rectangular cross section, and can be formed from any suitable material 27 such as a nickel titanium alloy, stainless steel or a cobalt chromium alloy. The coating 37 may optionally be applied to one or more of the abluminal side 14', proximal edge 13', distal edge 15' and the luminal side 12' of the strut 17'. In the illustrative embodiment of FIG. 2B, the coating 37 covers both the luminal side 12' and the abluminal side 14'. Alternatively, the coating 37 may be applied to the abluminal side 14' but not the luminal side 12', or vice versa, depending on the intended application. The abluminal surface 14', proximal edge 13' and distal edge 15' are coated with a coating 37 adhered to the surface of the vascular stent 10. Preferably, the coating 37 includes one or more solid forms of a taxane therapeutic agent, such as paclitaxel. In one aspect, the coating 37 can consist essentially of a single solid form of the taxane therapeutic agent, such as a dihydrate solvated paclitaxel. In another aspect, the coating 37 includes a single layer comprising a mixture of two or more solid forms of the taxane therapeutic agent, such as a mixture of dihydrate solvated paclitaxel and amorphous paclitaxel. In yet another aspect, the coating 37 can include two or more layers each comprising one or more solid forms of the taxane therapeutic agent. The coating 37 is preferably at least substantially free of a polymer that alters the elution rate of the taxane therapeutic agent. For example, the coating preferably has less than about 0.1 micrograms per $mm^2$ of the coating of a polymer that alters the elution rate of the taxane therapeutic agent. The coating 37 may optionally include two or more layers each comprising or consisting essentially of a taxane therapeutic agent in one or more solid forms. Preferred multilayer coatings include an outer layer comprising an amorphous solid form of a taxane therapeutic agent. The outer layer preferably covers the exposed surface of the underlying coating layer(s). The outer layer can optionally include a mixture of other solid forms of the taxane therapeutic agent with the amorphous solid form. Multilayer coatings can include any number of layers beneath the outer coating, including 2, 3, 4, 5, 6, 7, and 8 layer coatings. One preferred two-layer coating configuration includes a first layer consisting essentially of a dihydrate paclitaxel solid form, and a second layer comprising an amorphous paclitaxel solid form. The second layer can be a mixture of the amorphous and the dihydrate solid forms of paclitaxel.

Figure 2C:
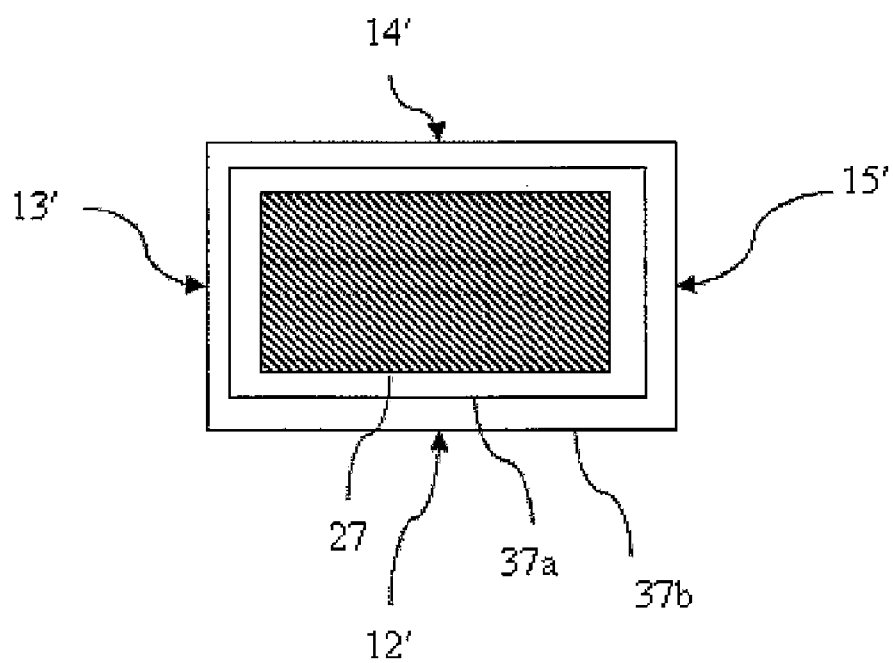
FIG. 2C shows a cross-sectional view of the portion of the medical device of FIG. 2B after a post-deposition conditioning step.
Figure 4A:
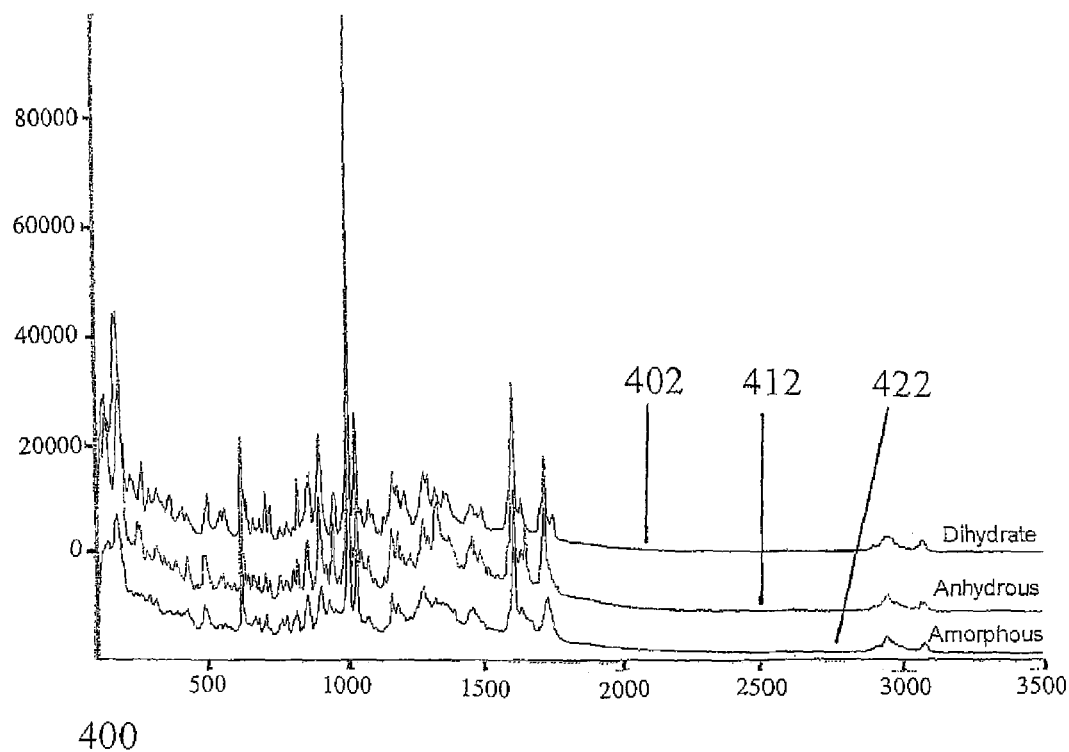
FIG. 4A shows a series of confocal Raman spectra for various solid forms paclitaxel.
Figure 4B:
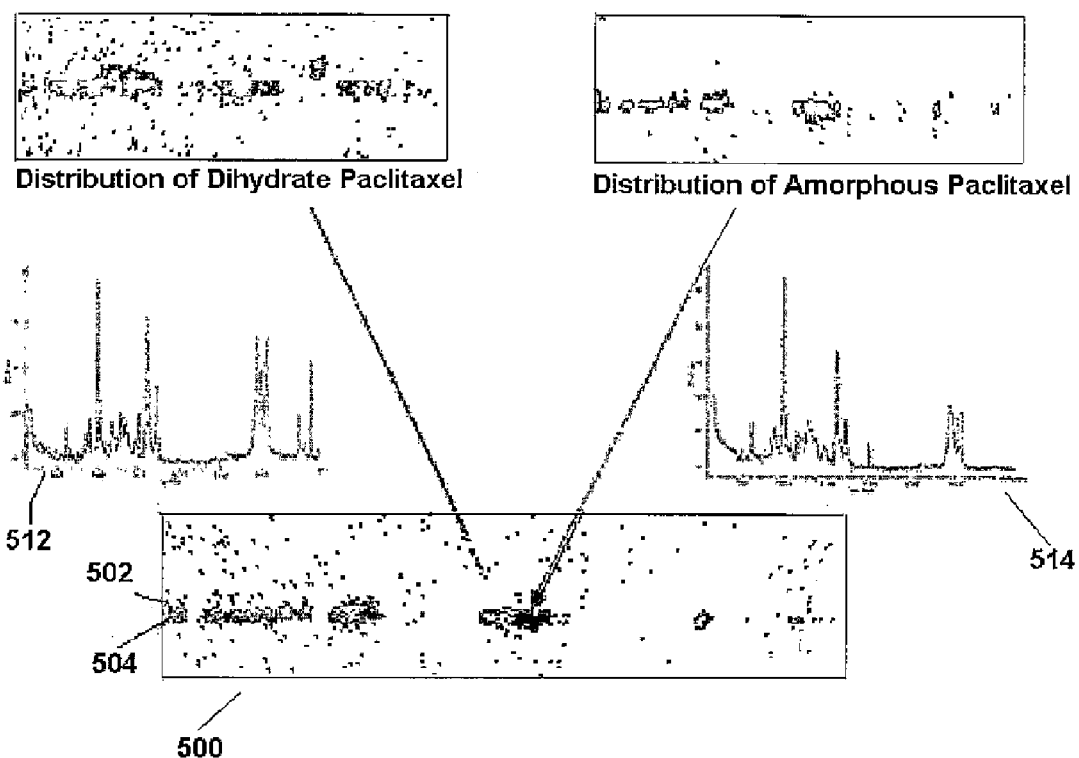
FIG. 4B shows the spatial distribution of two different solid forms of paclitaxel as a function of coating depth, obtained using confocal Raman spectroscopy.

FIG. 2C shows a cross section along line A-A' of coated strut 17' from the vascular stent 10 shown in FIG. 2A after conditioning the coating 37 shown in FIG. 2B. Referring to FIG. 2C, the strut is similar to the coated strut 17' in FIG. 2B, except as indicated below. The abluminal side 14', proximal edge 13', distal edge 15' and the luminal side 12' are all coated with a coating comprising a first portion 37a enclosed by a second portion 37b adhered to the surface of the vascular stent 10. The first coating portion 37a in FIG. 2C may have substantially unchanged from the composition of coating 37 in FIG. 2B, being formed of a taxane therapeutic agent in a first solid form, or a mixture of the taxane therapeutic agent having a first fraction of the taxane therapeutic agent in a first solid form and a second fraction of the taxane therapeutic agent in a second solid form. After the conditioning step, a second portion of the coating 37b (typically the outer portion of the coating 37 in FIG. 2B) contains a higher fraction of the taxane therapeutic agent in the second solid form compared to the first coating portion 37a. The conditioning step is preferably performed in a manner effective to convert at least a portion of the taxane therapeutic agent in the first solid form in FIG. 2B to the second solid form to form the second coating portion 37b in FIG. 2C. Preferably, the entire coating 37a, 37b consists of the taxane therapeutic agent in the first solid form and/or the second solid form (where present). Most preferably, the conditioning step converts a portion of the taxane therapeutic agent in the coating 37 in FIG. 2B from an amorphous solid form to a hydrated solid form, such as a dihydrate solid form. For example, a coating 37 in FIG. 2B consisting essentially of amorphous paclitaxel may be conditioned by methods described herein to form the coating in FIG. 2C having a first coating portion 37a with a first fraction of the amorphous paclitaxel (e.g., 60-80%) and a second coating portion 37b with a second fraction of amorphous paclitaxel (e.g., 20-30%) and a third fraction of dihydrate paclitaxel (e.g., 70-80%). As a result, the second coating portion 37b may have a slower elution rate than the unconditioned coating 37 would have. The second coating portion 37b may also have a slower elution rate than the first coating portion 37a. While the first coating portion 37a and the second coating portion 37b are depicted as being concentrically arranged around a strut 27, other embodiments provide for conditioned coatings containing a mixture of the first coating portion 37a and the second coating portion 37b within a single layer (side-by-side), for example as shown in FIG. 4B.

Various medical devices having a coating comprising a taxane therapeutic agent are provided. The medical device preferably comprises a coating having one or more layers. Preferably, the coating includes one or more solid forms of a taxane therapeutic agent described with respect to the first embodiment. The coating is preferably a single-layer of a therapeutically effective amount of the taxane therapeutic agent. Preferably, the single-layer consists of the taxane therapeutic agent in one or more solid forms. The therapeutically effective amount can depend upon the type and severity of the condition to be treated; the type and activity of the specific therapeutic agent employed; the method by which the medical device is administered to the patient; the age, body weight, general health, gender and diet of the patient; the time of administration, route of administration, and rate of excretion of the specific compound employed; the duration of the treatment; drugs used in combination or coincidental with the specific compound employed; and like factors well known in the medical arts.

To obtain the desired dosage of therapeutic agent, the solid form of the taxane therapeutic agent in the coating may be varied. In one embodiment, the coating contains from about 0.01 micrograms to about 10 micrograms of the taxane therapeutic agent per $mm^2$ of the surface area of the structure, preferably about 0.05 micrograms to about 5 micrograms, about 0.03 micrograms to about 3 micrograms, about 0.05 micrograms to about 3 micrograms, about 0.5 micrograms to about 4.0 micrograms, most preferably between about 0.5 and 3.0 micrograms, of the taxane therapeutic agent per $mm^2$ of the abluminal surface area of the structure. Desirably, a total of about 1-500 micrograms of a taxane therapeutic agent (such as paclitaxel) is coated on one or more surface of a medical device.

The thickness of the coating layer comprising the taxane therapeutic agent is between 0.1 micrometer and 20 micrometers, between 0.1 micrometer and 10 micrometers, or between 0.1 micrometer and 5 micrometers. For the purposes of local delivery from a stent, the daily dose that a patient will receive depends at least on the length of the stent. The total coating thickness is preferably about 50 μm or less, preferably less than about 20 micrometers and most preferably about 0.1-10 micrometers.

For example, a 6×20 mm stent may be coated with about 0.05-5 micrograms/$mm^2$ of paclitaxel, more preferably about 0.5-3 micrograms/$mm^2$, can be applied to the abluminal surface of the stent. Particularly preferred doses of a taxane therapeutic agent on the abluminal surface of a stent include: 0.06, 0.30, 1.00 and 3.00 micrograms/$mm^2$. In another embodiment, the abluminal side of a 6×20 mm stent (surface area of about 73 $mm^2$) is coated with about 20-220 micrograms of paclitaxel. Examples of particularly preferred coatings for a 6×20 mm vascular stent having an abluminal surface area of about 73 $mm^2$, and a compressed diameter of about 7 F are described below.

The coated medical device may also include a taxane therapeutic agent at least partially contained within the medical device frame material. The medical device may have pores, holes, wells, slots, grooves, or the like for containing the therapeutic agent (see, e.g., co-pending U.S. patent application Ser. No. 10/870,079, filed Jun. 17, 2004 and incorporated herein by reference). Alternatively, the therapeutic agent and/or polymer may be incorporated into a biodegradable medical device that releases the agent as the device degrades, or the therapeutic agent and/or polymer may be incorporated into or placed on the medical device in any other known manner.

Solid Forms of Taxane Therapeutic Agent Compositions

The different solid forms of the taxane therapeutic agent preferably contain one or more types of taxane therapeutic agent(s) arranged in different crystalline or non-crystalline forms in the coating, although a mixture of two or more taxane therapeutic agents can also be used. Preferably, the taxane therapeutic agent is paclitaxel. The solvated solid forms further comprise water molecules to form a solvated solid form, such as dihydrate paclitaxel (paclitaxel.$2H_2O$). The molar ratio between the taxane therapeutic agent and the waters of hydration in a solvated solid form may include integer ratios as well as non-integer ratios, such as 2.$2H_2O$ per paclitaxel water molecules. Preferably, the solvated solid form comprises a molar ratio of about 1.0 to 5.0 water molecules per molecule of taxane therapeutic agent, including ratios 1.2, 1.3, 1.4, 1.5, 1.6, 1.7, 1.8, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 and 5.0, and higher, water molecules of hydration per molecule of taxane therapeutic agent in the solvated solid form.

Figure 3A:
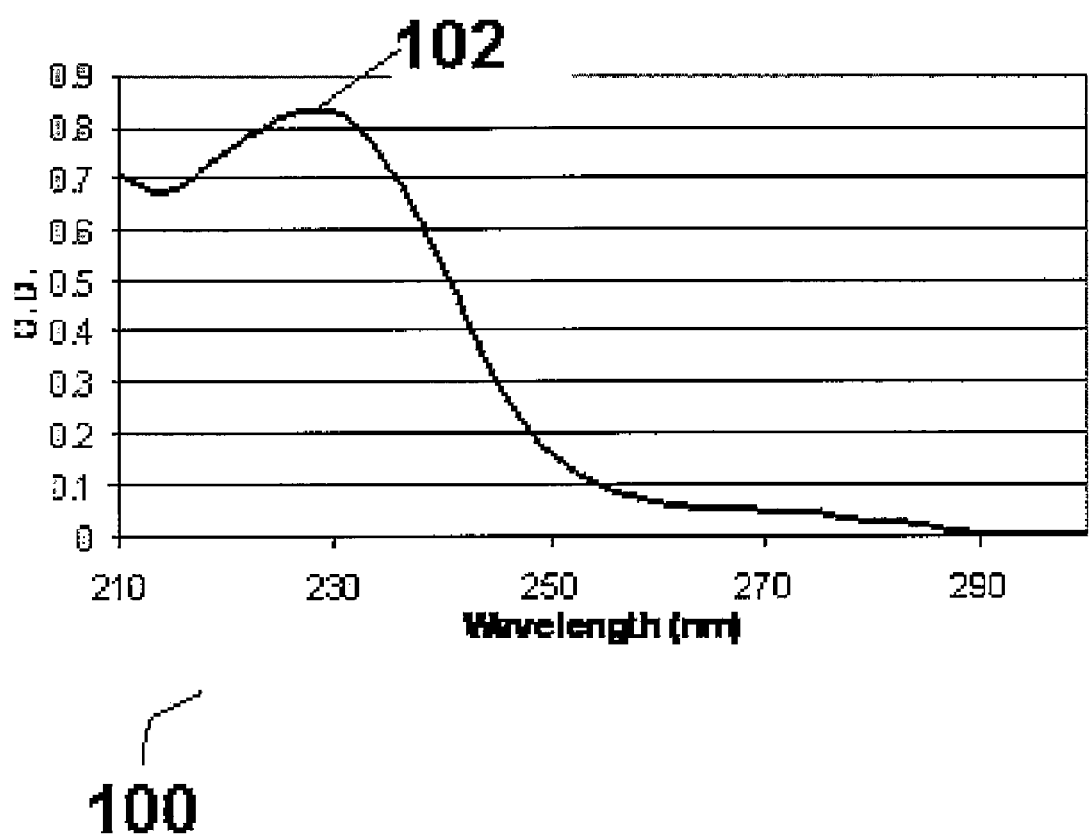
FIG. 3A shows an ultraviolet (UV) absorption spectrum of paclitaxel in ethanol.

The presence of a taxane therapeutic agent in a coating structure can be identified by detecting the core taxane structure, for example by ultraviolet detection methods. For example, samples of the coating may be destructively tested by dissolving the coating in any suitable elution medium that permits measurement of a characteristic peak of the taxane therapeutic agent in solution in an ultraviolet (UV) spectrum of the taxane therapeutic agent in the solution. The characteristic peak is preferably associated with the core taxane structure. Methanol and ethanol are preferred examples of a suitable solvents. FIG. 3A shows an ultraviolet (UV) spectrum 100 (Agilent In-line UV Spectrophotometer) of paclitaxel in ethanol, obtained from a 25.67 micromolar solution of paclitaxel in ethanol. Paclitaxel provides a characteristic peak at 227 nm (102) indicative of the presence of the core taxane structure of paclitaxel in the solution. Taxane therapeutic agent can be identified from a UV spectrum of the elution medium characterized by the characteristic peak at about 227 nm, which can be correlated to the presence of the taxane therapeutic agent in the solution, regardless of the solid form from which the taxane molecule originated.

Different solid forms of taxane therapeutic agents in medical device coatings can have identical molecular structures, but differ in the arrangement of the taxane molecules in the coating. Various solid forms of the taxane therapeutic agent can be identified and differentiated on the basis of one or more physical properties including melting point, solubility and appearance. In addition, various other analytical methods can be used to identify different solid forms of the taxane therapeutic agents, including vibrational spectroscopy (including Raman or Infrared Spectra), solubilities, melting points, X-ray Diffraction (XRD), $^{13}$C Nuclear Magnetic Resonance (NMR), and Temperature Programmed Desorption (TPD)).

As referred to in steps (ii) or step (1) of FIG. 1A, different solid forms of the taxane therapeutic agent (including amorphous, anhydrous or dihydrate forms) can be formed by dissolving the solid taxane therapeutic agent, typically obtained in the anhydrous form, in different solvents, as described below. These three solid forms of paclitaxel can be prepared and identified by the methods described in J. H. Lee et al, "Preparation and Characterization of Solvent Induced Dihydrated, Anhydrous and Amorphous Paclitaxel," *Bull. Korean Chem. Soc.*, v. 22, no. 8, pp. 925-928 (2001), which is incorporated herein by reference in its entirety.

Figure 3B:
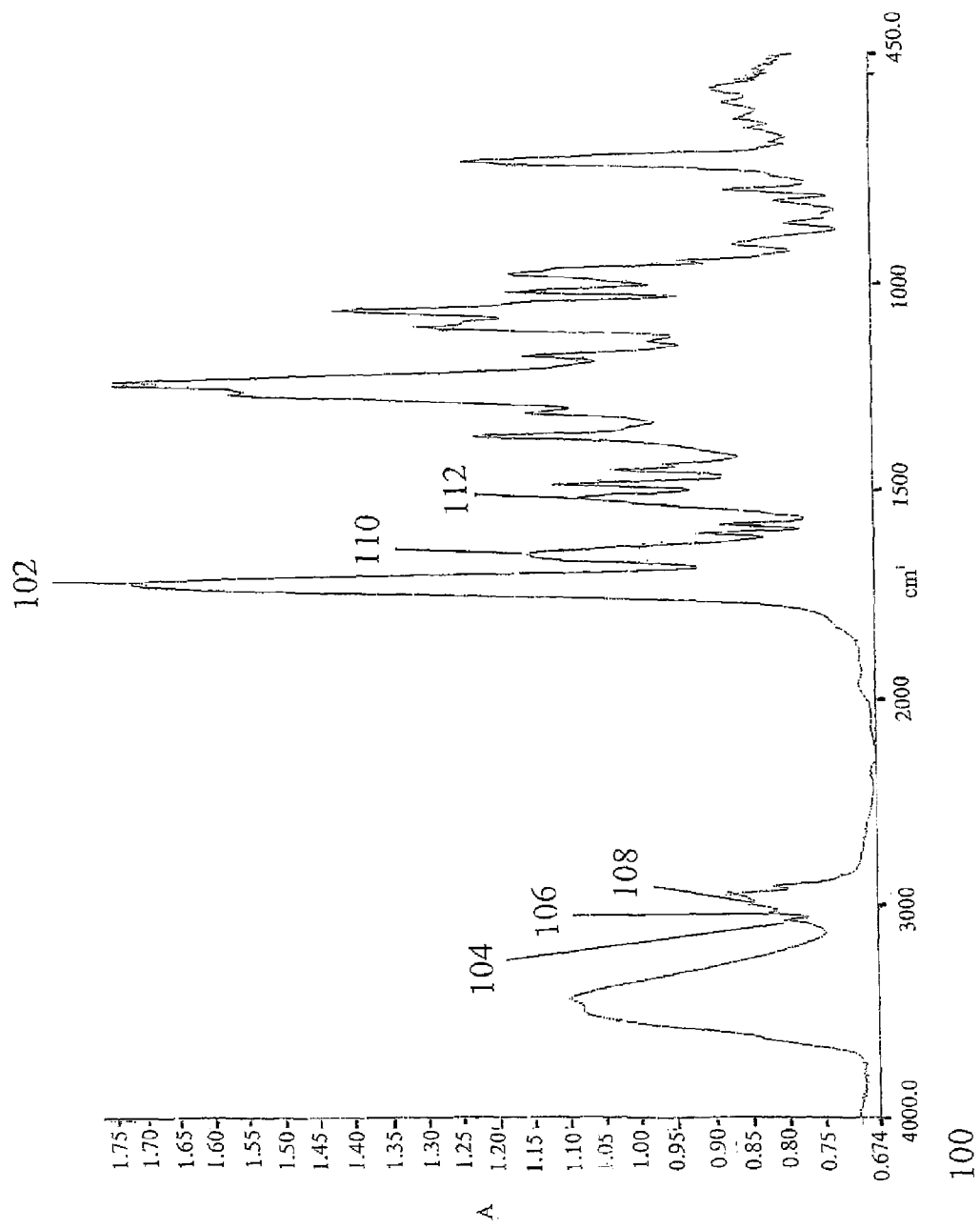
FIG. 3B shows an infrared spectrum of a first solid form of paclitaxel.

In a first aspect of the first embodiment, medical devices comprising an amorphous taxane therapeutic agent, such as amorphous paclitaxel ("aPTX"), are provided as the first solid form of the taxane therapeutic agent in step 1 or step (ii) of FIG. 1A. Bulk amorphous paclitaxel can be prepared by dissolving the taxane therapeutic agent in any suitable aprotic organic solvent, preferably in methylene chloride (dichloromethane), followed by removal of the solvent to leave an amorphous solid. Chloroform can also be used as the organic solvent. For example, amorphous taxane therapeutic agent can be formed by first dissolving the solid taxane therapeutic agent in dichloromethane, followed by crystallization at and evaporation of the dichloromethane and subsequent vacuum drying of the sample. Desirably, the synthesis method is carried out in a low humidity environment (preferably below about 40% relative humidity, more preferably below about 30% and most preferably below about 20% relative humidity or less), and at about 23° C. FIG. 3B shows an infrared vibrational spectrum of an amorphous paclitaxel prepared via the method of Example 1. The spectrum of amorphous paclitaxel 100 includes a single broad peak at about 1723 cm$^{-1}$ (102), as well as the following other characteristic peaks: 3064 cm$^{-1}$ (104), 3029 cm$^{-1}$ (106), 2942 cm$^{-1}$ (108), 1650 cm$^{-1}$ (110), and 1517 cm$^{-1}$ (112). The melting points of the amorphous paclitaxel samples prepared according to Example 1 were about 190° C.-210° C. An amorphous taxane therapeutic agent can be identified by the presence of a single broad peak between about 1700-1740 cm$^{-1}$ in the infrared spectrum, typically at about 1723 cm$^{-1}$. The amorphous taxane therapeutic agent was found to be more soluble in porcine serum than the dihydrate taxane therapeutic agent, but less soluble than the anhydrous taxane therapeutic agent.

Figure 3C:
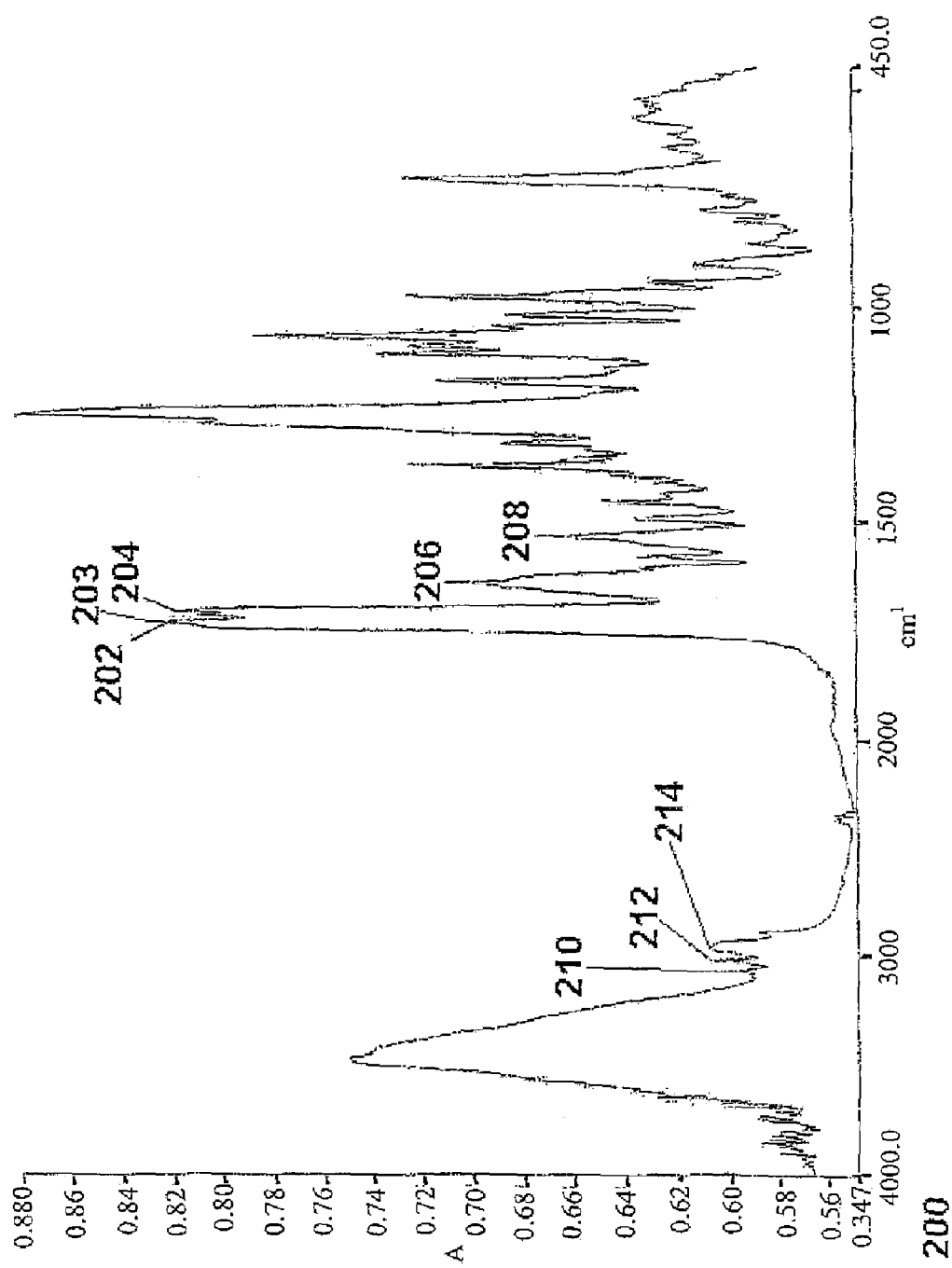
FIG. 3C shows an infrared spectrum of a second solid form of paclitaxel.
Figure 3D:
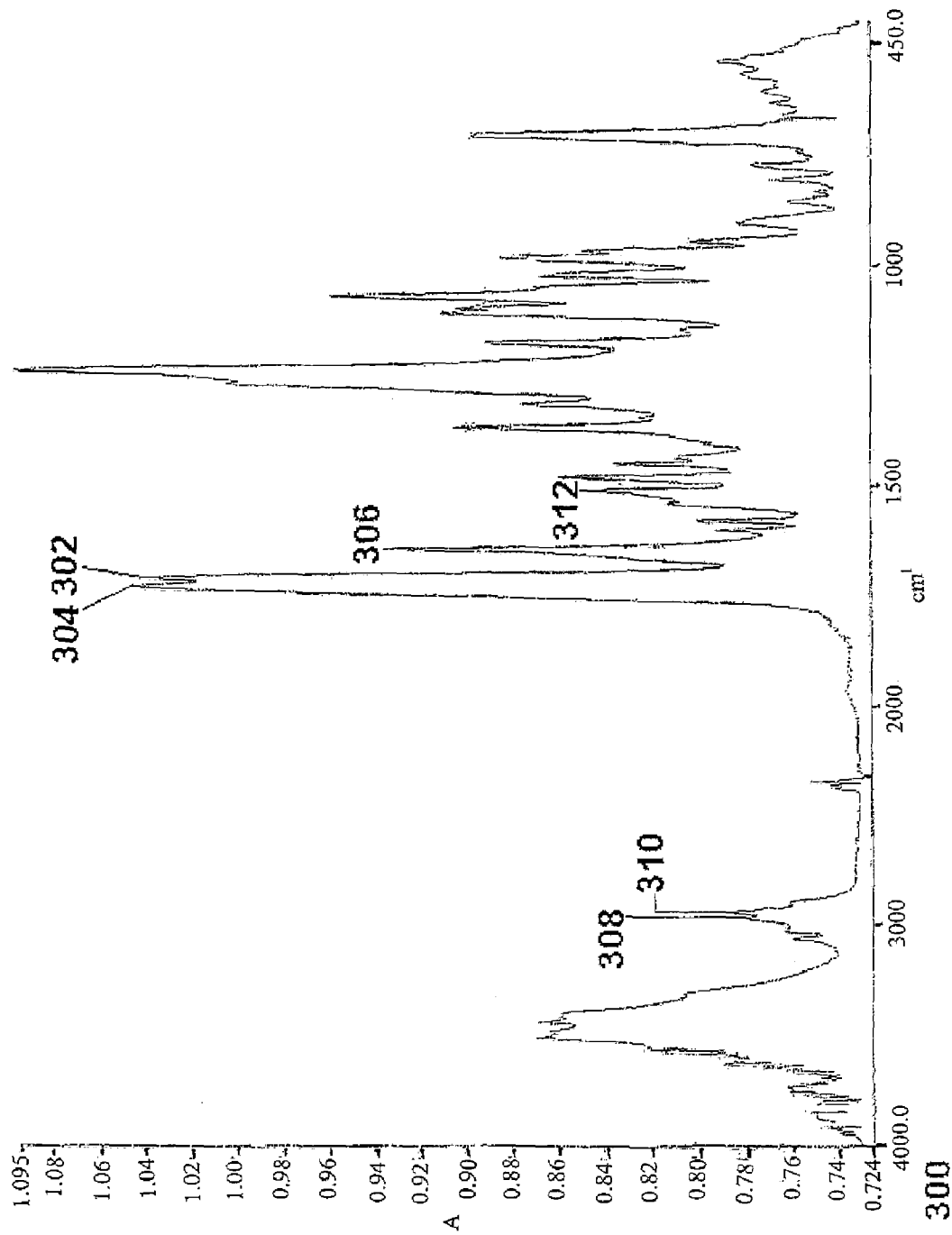
FIG. 3D shows an infrared spectrum of a third solid form of paclitaxel.

In a second aspect of the first embodiment, the composition comprises an anhydrous taxane therapeutic agent, such as anhydrous paclitaxel. Anhydrous taxane therapeutic agents preferably contain less than about 1.00% water (more preferably less than about 0.60%, 0.55% or 0.50% water), as measured by Karl Fischer analysis. Bulk samples of anhydrous taxane therapeutic agent can be prepared by dissolving a taxane therapeutic agent such as paclitaxel in any suitable alcohol-based solvent, followed by evaporation of the solvent to leave an crystalline solid. Typically, the taxane therapeutic agent is first dissolved in a methanol solvent, followed by the gradual addition of hexane to the solution. For example, as described in more detail in Example 1, anhydrous taxane therapeutic agent can be formed by first dissolving paclitaxel in methanol to form a solution, followed by addition of hexane to the solution and subsequent evaporation of the methanol and hexane. Acetone, ethyl acetate or diethyl ether are also suitable solvents for combination with hexane in forming the anhydrous solid form of a taxane therapeutic agent. The anhydrous paclitaxel prepared according to Example 1 was characterized by Infrared Spectrophotometry. FIG. 3D shows an infrared vibrational spectrum of an anhydrous paclitaxel prepared according to the method of Example 1. The spectrum of anhydrous paclitaxel 300 includes a pair of peaks between about 1700-1740 cm$^{-1}$, typically two peaks at about 1714 cm$^{-1}$ (302) and about 1732 cm$^{-1}$ (304), as well as the following other characteristic peaks: 3065 cm$^{-1}$ (308), 2944 cm$^{-1}$ (310), 1646 cm$^{-1}$ (306), and 1514 cm$^{-1}$ (312). The melting points of the anhydrous paclitaxel samples prepared according to Example 1 were about 220° C.-221° C. The anhydrous taxane therapeutic agent was found to be more soluble in porcine serum than the amorphous taxane therapeutic agent, and significantly more soluble than the dihydrate taxane therapeutic agent.

A conditioned coated medical device according to step 3 of the first embodiment preferably comprises a solvated taxane therapeutic agent, such as dihydrate paclitaxel ("dPTX"), as well as a suitable amount of a non-solvated solid form of the taxane therapeutic agent. The conditioning step(s) (e.g., steps 2' and/or step 2" in FIG. 1A) preferably convert at least a portion of the taxane therapeutic agent in the coating to the dihydrate solid form. The conditioning steps may, for example, convert at least a portion of a taxane therapeutic agent from an amorphous or anhydrous solid form within the coating to a dihydrate solid form. Typically, at least the outermost portion of the taxane therapeutic agent in a coating is converted to the dihydrate solid form.

Dihydrate taxane therapeutic agent may also be formed in bulk for the purpose of calibrating the detection of dihydrate taxane therapeutic agent measured in a coating. Bulk samples of dihydrate paclitaxel can be prepared by dissolving the taxane therapeutic agent in any suitable alcohol-based solvent, followed by evaporation of the solvent to leave a crystalline solid. Typically, the taxane therapeutic agent is first dissolved in a methanol or ethanol solvent, followed by the gradual addition of water to the solution. Specifically, bulk dihydrate taxane therapeutic agent may be prepared by a multi-step process: (1) first, dissolving a solid anhydrous taxane therapeutic agent in methanol to form a solution, followed by (2) adding water to the solution in a step-wise manner, followed by (3) crystallization. The water is preferably added very slowly, in a drop-by-drop manner, waiting for solution to become clear before the addition of the next drop of water, until the solution includes 80% v/v methanol and 20% v/v water. The dihydrate taxane therapeutic agent can be collected by filtration and vacuum evaporation of the methanol and water. Desirably, the synthesis method is carried out in a high humidity environment (preferably at least about 20% relative humidity, more preferably about 40% or greater relative humidity), and at temperatures of about 23° C. or higher. Alternatively, studies have reported formation of paclitaxel dihydrate by incubation of anhydrous paclitaxel in water for 24 hours at 25° C. See, e.g., R. T. Liggins et al., "Solid-State Characterization of Paclitaxel," *Journal of Pharmaceutical Sciences*, v. 86, No. 12, p. 1461 (December 1997). The vibrational spectrum of the dihydrate paclitaxel prepared according to Example 1 may be obtained by Infrared Spectrophotometry. FIG. 3C shows an infrared vibrational spectrum of a dihydrate paclitaxel prepared according to the method of Example 1. The spectrum of dihydrate paclitaxel 200 includes three or more peaks between about 1700-1740 $cm^{-1}$, typically three peaks at about 1705 $cm^{-1}$ (204), about 1716 $cm^{-1}$ (203) and about 1731 $cm^{-1}$ (202), as well as the following other characteristic peaks: 3067 $cm^{-1}$ (210), 3017 $cm^{-1}$ (212), 2963 $cm^{-1}$ (214), 1639 $cm^{-1}$ (206), and 1532 $cm^{-1}$ (208). The melting points of the dihydrate paclitaxel samples prepared according to Example 1 were about 209° C.-215° C. Dehydration of dihydrate paclitaxel has been reported during heating at a rate of 10° C./min over a temperature range of between about 35° C. and about 100° C. measured by DSC (with peaks observed at about 50° C. and about 72° C.), and between about 25° C. and about 85° C. measured by Thermogravimetric Analysis (TGA), with lower temperatures reported at slower heating rates. R. T. Liggens et al., "Solid-State Characterization of Paclitaxel," *Journal of Pharmaceutical Sciences*, v. 86, No. 12, pp. 1458-1463, 1461 (December 1997) ("Liggins"). The dihydrate paclitaxel has been reported to not show weight loss or evidence of dehydration when stored for several weeks when stored at 25° C. at 200 torr. Liggens et al., page 1461. The solubility of the bulk sample of dihydrate taxane therapeutic agent may be measured in various elution media to obtain a dihydrate control elution profile. The elution profile of a taxane therapeutic agent measure in the elution media may be compared to the dihydrate control elution profile to identify the amount of dihydrate solid form present in a taxane therapeutic agent coating to identify the amount of the dihydrate present in the coating by comparison with the dihydrate control elution profile.

Suitable solvent systems for the synthesis of amorphous, dihydrate and anhydrous taxane therapeutic solid forms, as well as characteristic melting point ranges and infrared spectrum peaks useful in identifying each solid form, are provided in Table 1. Other solvent systems can also be used to form one or more of the taxane solid forms described herein, and other IR peaks can be used to identify the type(s) of solid forms present in a taxane therapeutic agent solid sample.

TABLE 1

Preparation and Identification of Taxane Solid Forms

| | Desired Taxane Solid Form | | |
|---|---|---|---|
| | Amorphous | Anhydrous | Dihydrate |
| Solvent: | Dichloromethane | Methanol/Hexane | Methanol/Water |
| Melting Point: | 190-210° C. | 220-221° C. | 209-215° C. |
| Characteristic IR peaks: | Single peak between 1700-1740 $cm^{-1}$ | Two peaks between 1700-1740 $cm^{-1}$ | Three or more peaks between 1700-1740 $cm^{-1}$ |
| | 3064 $cm^{-1}$ (104), 3029 $cm^{-1}$ (106), 2942 $cm^{-1}$ (108) | 3065 $cm^{-1}$ (308), 2944 $cm^{-1}$ (310) | 3067 $cm^{-1}$ (210), 3017 $cm^{-1}$ (212), 2963 $cm^{-1}$ (214) |
| | 1650 $cm^{-1}$ (110) | 1646 $cm^{-1}$ (306) | 1639 $cm^{-1}$ (206) |
| | 1517 $cm^{-1}$ (112) | 1514 $cm^{-1}$ (312) | 1532 $cm^{-1}$ (208) |

Differentiation of taxane solid states by vibrational spectroscopy can also be performed using Raman scattering. Raman scattering describes the phenomenon whereby incident light scattered by a molecule is shifted in wavelength from the incident wavelength. The magnitude of the wavelength shift depends on the vibrational motions the molecule is capable of undergoing, and this wavelength shift provides a sensitive measure of molecular structure. That portion of the scattered radiation having shorter wavelengths than the incident light is referred to as anti-Stokes scattering, and the scattered light having wavelengths longer than the incident beam as Stokes scattering. Raman scattering is a spectroscopic method useful for the detection of coatings, as the Raman spectra of different coatings or coating layers can be more distinct than the spectra obtained by direct light absorption or reflectance. FIG. 4A shows an overlay of three Raman spectral traces 400 recorded as an average of 10 spectra of three solid paclitaxel coatings on a stainless steel surface using a FT-Raman spectrometer, with excitation from a 532 nm laser with a power output of 8 mW. The three spectral traces correspond to the dihydrate (402), anhydrous (412) and amorphous (422) paclitaxel samples. Each spectral trace was collected over a 10 second integration each (total acquisition time of 100 seconds), using an air objective (100×, NA=0.9). Differences in the characteristic vibrational peaks can be used to differentiate the dihydrate, anhydrous and amorphous forms of the solid paclitaxel. The characteristic vibrational peaks correspond to the infrared characteristic peaks discussed with respect to the infrared spectra of FIGS. 3B-3D, and include the peaks listed in Table 1. Most notably, the presence of a single peak between 1700-1740 cm$^{-1}$ indicates the presence of an amorphous taxane therapeutic agent solid form, the presence of three or more peaks between 1700-1740 cm$^{-1}$ indicates the presence of the dihydrate taxane therapeutic agent solid form, and the presence of two peaks between 1700-1740 cm$^{-1}$ indicates the presence of the anhydrous taxane therapeutic agent solid form.

Confocal Raman microscopy allows improved axial and lateral resolution and fluorescence rejection over conventional Raman microscopy. Confocal Raman microscopy can be applied to reveal compositional or structural gradients as a function of depth within a sample. A depth profile of a coating can be obtained by confocal Raman microscopy by plotting the intensity of a component-specific vibrational band as a function of the distance from the sample surface. FIG. 4B shows a depth profile 500 of a coating comprising a mixture of dihydrate and amorphous solid forms of paclitaxel. The depth profile 500 was obtained by confocal Raman microscopy, by spatially detecting and plotting the intensity of scattered light matching a first spectrum 512 obtained from a dihydrate paclitaxel sample in a first color 502, followed by similarly detecting and plotting the intensity of scattered light matching a second spectrum 514 obtained from an amorphous paclitaxel sample. The depth profile 500 indicates that the dihydrate paclitaxel 502 is largely localized on the surface of the coating while the amorphous paclitaxel is predominantly distributed in a layer 504 below the dihydrate paclitaxel.

Figure 5A:
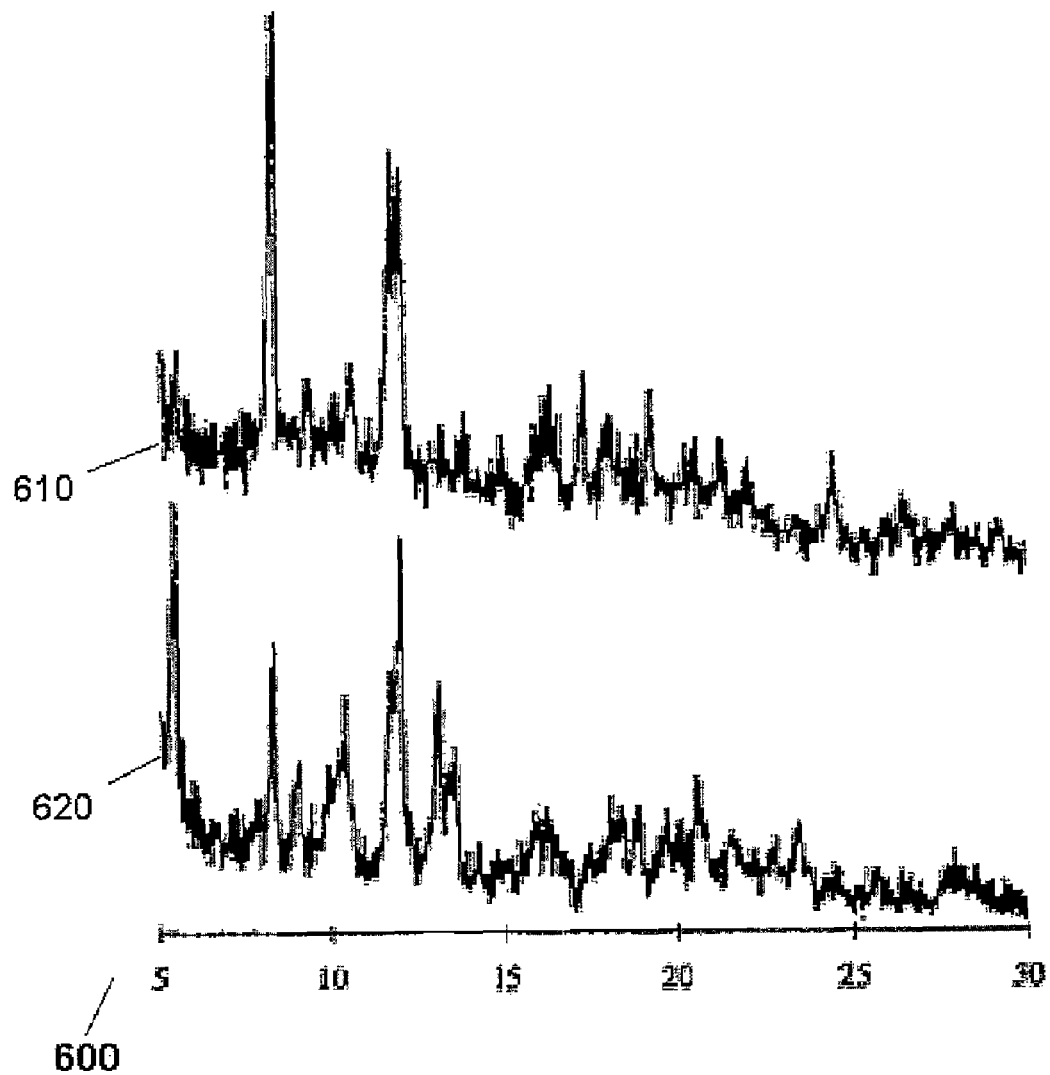
FIG. 5A shows a powder X-ray diffraction (XRPD) spectrum of two different solid forms of paclitaxel.

Powder X-ray Diffraction (XRPD) can also be used to differentiate various solid forms of taxane therapeutic agents. FIG. 5A shows the XRPD patterns 600 for amorphous 610 and dihydrate 620 solid forms of paclitaxel, with corresponding selected d-spacings of selected peaks provided in Table 2. Notably, the dihydrate paclitaxel can provide peaks different from the amorphous paclitaxel at 6.1, 9.5, 13.2 and 13.8° 2θ (obtained at 25° C.).

TABLE 2

XRPD Selected d-Spacings and Peak Intensities

| °2θ | d-spacing (Å) | Anhydrous | Dihydrate |
|---|---|---|---|
| 6.1 | 14.5 | | Strong* |
| 8.8 | 10.0 | Strong* | Strong* |
| 9.5 | 9.3 | | Medium** |
| 10.9 | 8.11 | | Medium** |
| 11.1 | 7.96 | Medium** | |
| 12.1 | 7.31 | Medium** | Strong* |
| 12.3 | 7.19 | Medium** | Strong* |
| 13.3 | 6.65 | | Medium** |
| 13.8 | 6.41 | | Medium** |
| 14.1 | 6.27 | Weak*** | |
| 19.3 | 4.59 | Weak*** | |
| 25.9 | 3.44 | Medium** | |

*= Strong Peak (relative intensity is more than 50);
**= Medium Peak (relative intensity between 20 and 50);
***= Weak Peak (relative intensity less than 20)

The data in FIG. 5A and Table 2 was obtained from R. T. Liggins et al., "Solid-State Characterization of Paclitaxel," *Journal of Pharmaceutical Sciences*, v. 86, No. 12, pp. 1458-1463 (December 1997), which is incorporated herein by reference. As described by Liggins et al., the anhydrous sample 610 can be obtained by drying paclitaxel (Hauser, Boulder, Colo.) at ambient temperature and reduced pressure (200 torr) in a vacuum oven (Precision Scientific, Chicago, Ill.). Liggins et al. report that the anhydrous sample 610 contained about 0.53% water, measured by Karl-Fischer analysis. The dihydrate sample 620 can be obtained by adding the anhydrous sample above to distilled water and stirring at ambient temperature for 24 hours, followed by filtration and collection of suspended solid paclitaxel and subsequent drying to constant weight. Liggins et al. report that the dihydrate sample 620 contained about 4.47% water (about 2.22 mol water/mol paclitaxel). Additional details relating to the spectra of FIG. 5A or the data in Table 2 are found in the Liggins et al. reference.

Figure 5B:
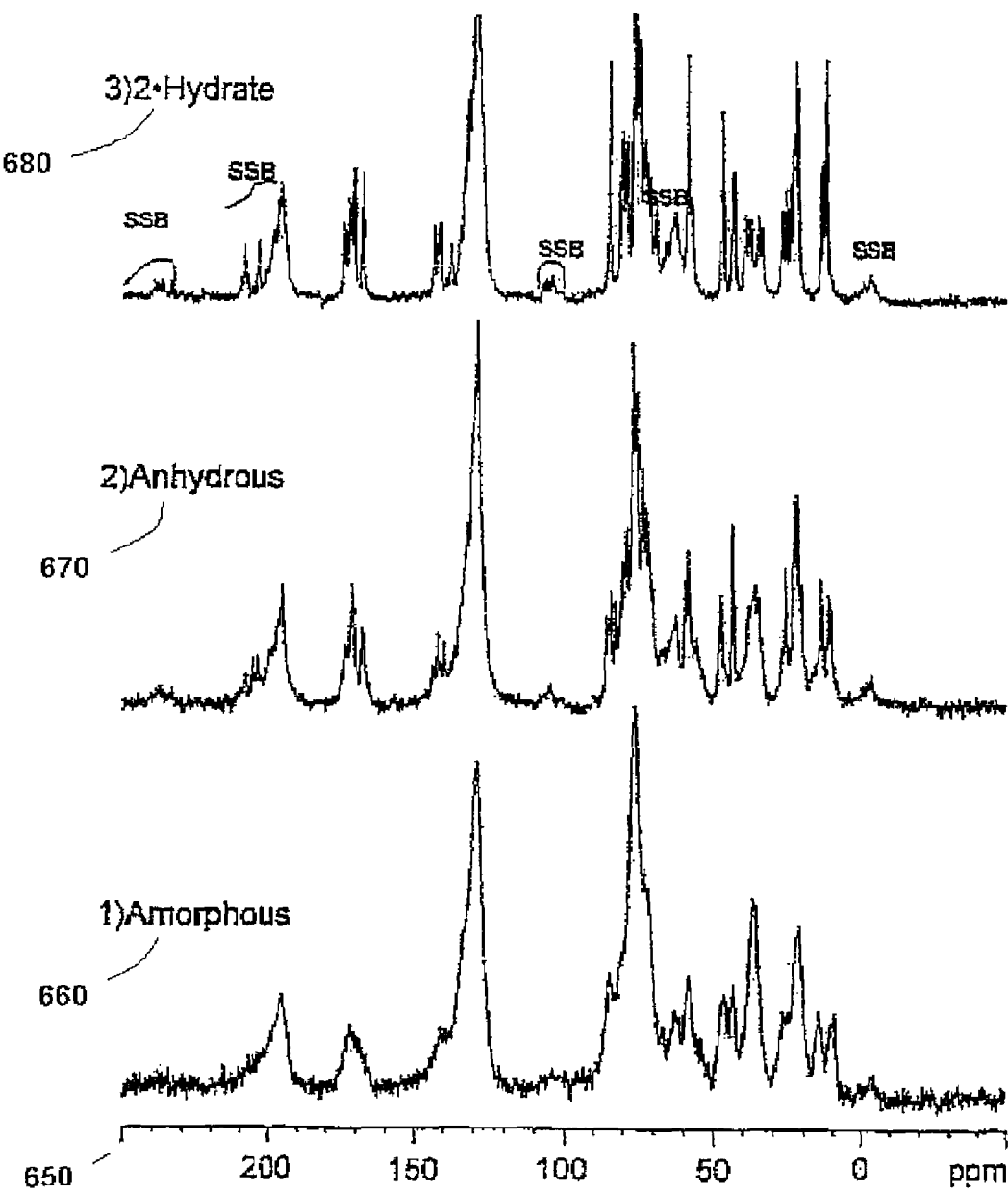
FIG. 5B shows a $^{13}C$ NMR spectrum of three different solid forms of paclitaxel.

A $^{13}$C Nuclear Magnetic Resonance (NMR) can also be used to differentiate various solid forms of taxane therapeutic agents. FIG. 5B shows the $^{13}$C NMR spectra 650 for amorphous 660, anhydrous 670 and dihydrate 680 solid forms of paclitaxel. The data in FIG. 5B was obtained from Jeong Hoon Lee et al., "Preparation and Characterization of Solvent Induced Dihydrated, Anhydrous and Amorphous Paclitaxel," *Bull. Korean Chem. Soc.* v. 22, no. 8, pp. 925-928 (2001), incorporated herein by reference. As described by Lee et al., the spectra 650 in FIG. 5B can be obtained using a cross polarization/magic angle spinning (CP/MAS) $^{13}$C solid form NMR (Bruker DSX-300, Germany) experiment operating at 75.6 MHz. Standard pulse sequences and phase programs supplied by Bruker with the NMR spectrometer can be used to obtain the spectra 650. For each sample, about 250 mg sample can be spun at about 5 kHz in a 4 mm rotor, and cross polarization can be achieved with contact time of 1 ms. This process can be followed by data acquisition over 35 ms with high proton decoupling. A three-second relaxation delay can be used. The spectra 650 are referenced to adamantane, using glycine as a secondary reference (carbonyl signal of glycine was 176.04 ppm). Referring to FIG. 5B, the $^{13}$C solid form NMR spectrum of the dihydrate paclitaxel 680 shows greater sharpness and peak splitting than either of the other solid forms of paclitaxel, the spectrum of the anhydrous paclitaxel 670 shows greater sharpness and peak splitting than the spectrum from amorphous paclitaxel 660, and the spectrum from amorphous paclitaxel 660 shows less resolution and peak splitting than the spectrum from anhydrous paclitaxel 670.

The presence of different solid forms of the taxane therapeutic agent in a medical device coating can preferably be identified by contacting the coating with an elution medium that selectively dissolves one solid form more readily than a second solid form. In solution with an elution medium, such as porcine serum or blood, the presence of the taxane therapeutic agent can be identified, for example by using ultraviolet (UV) spectroscopy or high pressure liquid chromatography (HPLC).

Preparation of Taxane Therapeutic Agent Coatings

The medical device coatings provided in step 1 or step (ii) of FIG. 1A may be prepared in by a variety of methods. Medical device coatings can comprise one or more of the solid forms of the taxane therapeutic agents, deposited on the medical device by spray coating a taxane therapeutic agent spray coating solution in any suitable manner. The coatings can be applied by a coating method described herein. The coating layer(s) may be deposited on the medical device in any suitable manner. For example, the coating may also be deposited onto the medical device by spraying, dipping, pouring, pumping, brushing, wiping, vacuum deposition, vapor deposition, plasma deposition, electrostatic deposition, epitaxial growth, or any other method known to those skilled in the art. Preferably, however, the medical device coatings are applied by spraying methods, such as those described herein.

Taxane Therapeutic Agent Spray Coating Solutions

Spray coating methods are preferably used to deposit taxane therapeutic agents onto the surface(s) of a medical device in one or more different solid forms. The spray coating can be performed by any suitable coating technique, but typically includes the step of dissolving the taxane therapeutic agent in a suitable solvent and spraying the resulting solution onto the surface of the medical device. Changing the solvent(s) in the solution can change the solid forms of the resulting taxane therapeutic agent deposited on a medical device. To deposit a coating of a dihydrate taxane therapeutic agent, a recrystallized dihydrate taxane therapeutic agent from the first embodiment can be dissolved in a suitable organic alcohol solvent, such as methanol. To deposit a coating layer comprising a mixture of dihydrate and amorphous taxane solid forms, the taxane is preferably dissolved in a spray solvent comprising a mixture of water and a protic solvent such as methanol. Importantly, varying the ratio of water to methanol and/or the concentration of the taxane in the spray solvent comprising the taxane typically changes the composition of the resulting coating layer that is spray deposited. Generally, increasing the amount of methanol in the spray solution results in a coating layer with a higher proportion of amorphous taxane.

Preferred spray solutions for obtaining durable coating are also listed herein, along with the preferred resulting minimum ratio of dihydrate to amorphous solid forms obtained by ultrasonic spray coating of the preferred solution. Importantly, the ratio of amorphous to dihydrate solid forms in a solid taxane solid coating may be changed by altering the methanol to water ratio and/or the concentration of the taxane therapeutic agent in the spray solution. Decreasing the concentration of the taxane in the spray solution may require a lower methanol to water ratio (i.e., less methanol and more water by volume) to obtain a given dihydrate to amorphous ratio in the solid coating formed after spraying and evaporation of the solvent. The spray solution can be made with any suitable concentration of the taxane therapeutic agent, although concentrations of about 0.5-5 mM are preferred, with concentrations of about 4.68 mM, 2.34 mM, 1.74 mM, 1.17 mM or 0.70 mM being particularly preferred. The relationship between the concentration of the taxane therapeutic agent in the spray solution, the ratio of methanol to water in the spray solution and the ratio of dihydrate to amorphous solid forms in the solid coating formed by spray coating the spray solution is illustrated with respect to paclitaxel in Tables 3a and 3b. Table 3a provides preferred spray solvent compositions for the spray deposition of a coating layer comprising a mixture of dihydrate paclitaxel and amorphous paclitaxel using a 4.68 mM paclitaxel concentration in the spray solution. Table 3a shows the ratio of methanol to water in a spray coating solution comprising about 4.68 mM paclitaxel, and the ratio of amorphous:dihydrate paclitaxel in a single coating layer deposited on a stent surface by spray coating the solutions with the specified compositions. Table 3b shows the ratio of methanol and water in a spray solution comprising various two-solvent solutions at 2.34 mM paclitaxel, 1.74 mM paclitaxel and 0.70 mM paclitaxel. Preferably, the coatings were applied by spraying a solution of 1.74 mM paclitaxel TABLE 3a Spray Coating Solvent Compositions for 4.68 mM Paclitaxel Solution

| dPTX:aPTX ratio | Solvent (% MeOH:H$_2$0) |
| --- | --- |
| >90%:<10% | 60:40%-90:10% |
| 60:40%-70:30% | 92:8%-93.5:6.5% |
| 40:60%-50:50% | 93.5:6.5%-94.55.5% |
| 30:70%-40:60% | 95.5%-97.5:2.5% |

TABLE 3b

Spray Coating Solvent Compositions at Lower Paclitaxel Concentrations

| dPTX:aPTX ratio | Solvent (% MeOH:H$_2$0) | [PTX] mM |
| --- | --- | --- |
| 52:48% | 88:12% | 2.34 |
| 42:58% | 90:10% | |
| 25:75% | 93:7% | |
| 78:22% | 70:30% | 0.70 |
| 65:35% | 75:25% | |
| 55:45% | 80:20% | |

In one aspect, the amount of hydrated solid form of a taxane therapeutic agent is increased by applying an additional layer of the taxane therapeutic agent to an existing coating of the taxane therapeutic agent. Increasing the number of spray applications of the 1.74 mM paclitaxel solution increased the amount of dihydrate paclitaxel solid form at a given methanol to water ratio. As shown in Table 3c, applying each of two 1.74 mM paclitaxel solutions in a methanol-water binary solvent system (a first solution consisting of 68% methanol and 32% water or a second solution consisting of 65% methanol and 35% water) by spray coating resulted in higher fractions of dihydrate paclitaxel solid form after multiple spray coating applications (e.g., passes of the spray gun over the surface) than a single application.

TABLE 3c

Multiple Spray Applications of a Paclitaxel Solution

| dPTX:aPTX ratio | Solvent (% MeOH:H$_2$0) | [PTX] mM |
| --- | --- | --- |
| 33:67 (1 application) | 68:32% | 1.74 |
| 60:40 (4 applications) | 68:32% | |
| 34:66 (1 pass) | 65:35% | |
| 39:61 (4 passes) | 65:35 | |

In addition to selecting an appropriate solvent system, other coating parameters such as the spraying apparatus, spray rate, and nozzle configuration can be selected to provide coatings comprising one or more solid forms of a taxane therapeutic agent. The coating of the medical device will now be described using three illustrative methods: spray gun coating, electrostatic deposition (ESD), and ultrasonic deposition (USD). However, the medical device may be coated using any suitable manner.

Ultrasonic Spray Coating

Preferably, the taxane therapeutic agent is spray coated onto a medical device surface using an ultrasonic spray deposition (USD) process. Ultrasonic nozzles employ high frequency sound waves generated by piezoelectric transducers which convert electrical energy into mechanical energy. The transducers receive a high frequency electrical input and convert this into vibratory motion at the same frequency. This motion is amplified to increase the vibration amplitude at an atomizing surface.

Ultrasonic nozzles are typically configured such that excitation of a piezoelectric crystals creates a longitudinal standing wave along the length of the nozzle. The ultrasonic energy originating from the transducers may undergo a step transition and amplification as the standing wave traverses the length of the nozzle. The nozzle is typically designed such that a nodal plane is located between the transducers. For ultrasonic energy to be effective for atomization, the nozzle tip must be located at an anti-node, where the vibration amplitude is greatest. To accomplish this, the nozzle's length should be a multiple of a half-wavelength. In general, high frequency nozzles are smaller, create smaller drops, and consequently have smaller maximum flow capacity than nozzles that operate at lower frequencies.

Liquid introduced onto the atomizing surface absorbs some of the vibrational energy, setting up wave motion in the liquid on the surface. For the liquid to atomize, the vibrational amplitude of the atomizing surface should be adequately controlled. Below a certain amplitude, the energy may be insufficient to produce atomized drops. If the amplitude is excessively high, cavitation may occur. The input power is preferably selected to provide an amplitude producing a desired spray having a fine, low velocity mist. Since the atomization mechanism relies largely on liquid being introduced onto the atomizing surface, the rate at which liquid is atomized depends on the rate at which it is delivered to the surface.

For example, the medical device may be coated using an ultrasonic spray nozzle, such as those available from Sono-Tek Corp., Milton, N.Y. The spray solution can be loaded into a syringe, which is mounted onto a syringe pump and connected to a tube that carries the solution to the ultrasonic nozzle. The syringe pump may then used to purge the air from the solution line and prime the line and spay nozzle with the solution. The stent may be loaded onto a stainless steel mandrel in the ultrasonic coating chamber. The stent may optionally be retained around a mandrel during coating. Alternatively, the stent may be secured and rotated on a clip or in within a steam of rapidly flowing gas such as nitrogen. Preferably, contact between the stent and the mandrel is minimized so as to prevent a "webbed" coating between struts. Typically, the luminal surface is not coated although the coating may be applied to any surface, if desired.

The medical device may be a vascular stent mounted around a mandrel. The mandrel may be fastened onto a motor, positioned below the ultrasonic nozzle. The motor rotates the mandrel at a pre-set speed and translationally moves the stent underneath the ultrasonic spray. In one aspect, the rotational speed is set to 10 rpm and the translational speed is set to 0.01 mm per second. In another aspect, the rotational speed is set to 60 rpm and the translational speed is set to 0.05 mm per second. In yet another embodiment, the rotational speed is set to 30-150, preferably about 110 rpm, and the translational speed is set to 0.19 mm per second. Other speeds and combinations may also be used in the present invention. Preferred coating parameters for USD using a Sono-tek Model 06-04372 ultrasonic nozzle are provided in Table 4 below:

TABLE 4

Ultrasonic Spray Deposition Parameters for Sono-tek Model 06-04372

| Flow rate (mL/min) | Coating velocity (in/sec) | Rotation Speed (rpm) | Nozzle Power (watts) | Process Gas (psi) | Distance (mm) |
|---|---|---|---|---|---|
| 0.01-2 | 0.01-0.5 | 30-150 | 0.9-1.2 | 0.1-2.5 | 1-25 |

Importantly, ultrasonic spray coating is preferably performed at an ambient temperature of about 85-87° F. and in a coating chamber at a pressure of less than about 0.05 psi. The temperature is preferably selected to provide a desirably uniform, solvent-free coating. Preferably, the coating is performed at a temperature of about 60-90° F., preferably about 85-87° F. The quality of the coating may be compromised if coating is performed outside the preferred temperature range. The temperature during ultrasonic spray coating should be high enough to rapidly evaporate the methanol in the spray solution before contacting the stent (i.e., at least about 80° F.).

Most preferably, the ultrasonic spray coating is performed at a flow rate of about 0.03 mL/min, a coating velocity of about 0.025 in/sec, a rotation speed of about 60 rpm, a nozzle power of about 1 watt, a process gas pressure of about 2 psi, a distance of about 12 mm between the nozzle and medical device, and a temperature of about 85° F. within a coating chamber. The coating chamber is purged with nitrogen to displace oxygen in the system. During the process, the stent is kept at ambient temperature and in a closed chamber.

Taxane coatings desirably comprise at least one layer including a durable amorphous solid form. Preferably, coatings comprising a mixture of amorphous and dihydrate taxane solid forms preferably include a minimum amount of amorphous taxane to impart a desired level of durability to the coating. Typically, coatings with at least about 25-30% amorphous taxane (i.e., dPTX:aPTX ratio including about 70-75% dPTX) have a desired level of durability to withstand a stent crimping procedure. Preferred spray solution compositions are selected to provide a coating having a taxane therapeutic agent with a dihydrate:amorphous solid form ratio with desired properties of elution rate, surface uniformity and durability. For example, preferred solvent systems for ultrasonic spray coating include a dihydrate:amorphous paclitaxel coating (e.g., from a SonoTek 06-04372 ultrasonic nozzle) with 60-70% w dihydrate (remainder amorphous) paclitaxel, and may be prepared by selecting paclitaxel, methanol and water concentrations according to Tables 3a-3b while spray coating at about 84-87° F. within the parameters specified in Table 4 above. The coatings can also be applied (in total or in part) by a coating method described with respect to the third embodiment, or any other suitable manner. For example, the coating may also be deposited onto the medical device by spraying, dipping, pouring, pumping, brushing, wiping, vacuum deposition, vapor deposition, plasma deposition, electrostatic deposition, epitaxial growth, or any other method known to those skilled in the art. Preferably, however, the medical device coatings are applied by spraying methods, such as those described with respect to the third embodiment above.

Pressure Spray Gun Coating

In another aspect of the third embodiment, medical device coatings comprising a taxane therapeutic agent are applied to a surface of a medical device using a spray gun. Spray gun coating may be performed with a spray solution of paclitaxel in ethanol, without using methanol or water in the spray solution. The surface of the medical device can be bare, surface modified, or a primer coating previously applied to the medical device. Preferably, the coating applied to the surface consists essentially of the taxane therapeutic agent, and is substantially free of polymers or materials that alter the elution rate of the taxane therapeutic agent. The taxane therapeutic agents described with respect to the first embodiment above can be dissolved in a solvent(s) and sprayed onto the medical device under a fume hood using a conventional spray gun, such as a spray gun manufactured by Badger (Model No. 200), or a 780 series spray dispense valve (EFD, East Providence, R.I.).

Alignment of the spray gun and stent may be achieved with the use of a laser beam, which may be used as a guide when passing the spray gun over the medical device(s) being coated. For spray gun coating, the therapeutic agent is preferably paclitaxel and the solvent is preferably ethanol. Desirably, a solution of about 0.5-5 mM paclitaxel in ethanol is used. More desirably, a solution of about 1-3 mM paclitaxel in ethanol is used. Even more desirably, a solution of about 2.4-4.7 mM paclitaxel in ethanol is used. Other therapeutic agents and solvents may also be used in the present invention. The distance between the spray nozzle and the nozzle size can be selected depending on parameters apparent to one of ordinary skill in the art, including the area being coated, the desired thickness of the coating and the rate of deposition. Any suitable distance and nozzle size can be selected. For example, for coating an 80 mm long stent, a distance of between about 1-7 inches between the nozzle and stent is preferred, depending on the size of the spray pattern desired. The nozzle diameter can be, for example, between about 0.014-inch to about 0.046-inch.

Varying parameters in the spray coating process can result in different solid forms of the taxane therapeutic agent in a deposited coating. Spray coating parameters such as solvent system, fluid pressure (i.e., tank pressure), atomization pressure, ambient temperature and humidity. The solvent is desirably volatile enough to be readily removed from the coating during or after the spray coating process, and is preferably selected from the solvents discussed with respect to the first embodiment for each solid form of a taxane therapeutic agent.

Typically, spray coating in lower humidity, higher atomization pressure and/or lower temperature (e.g., room temperature) conditions, favor the formation of the amorphous solid form of the taxane therapeutic agent. Methods of coating amorphous taxane therapeutic agents using a 780S-SS spray dispense valve (EFD, East Providence, R.I.) can comprise the steps of: dissolving solid paclitaxel in ethanol to form a spray solution of a desired concentration (e.g. 4.68 mM), and spraying the solution onto a medical device with an atomization pressure of about 5-10 psi in an environment having a relative humidity of 30% or lower. Preferably, the spraying step is performed at a temperature of between about 65° F. and 75° F., and with a fluid pressure of between about 1.00 and 5.00 psi. For example, amorphous paclitaxel (aPTX) coatings have been deposited using the EFD 780S-SS spray valve (EFD, East Providence, R.I.) under the following conditions: (1) 4.0 g/L PTX (4.68 mM) in ethanol spray solution, 20% relative humidity, 13.00 psi atomization pressure, 2.00 psi fluid (tank) pressure and 80° F. ambient temperature; and (2) 4.0 g/L PTX in ethanol spray solution, 30% relative humidity, 25.00 psi atomization pressure, 1.50 psi fluid (tank) pressure and 75° F. ambient temperature. An amorphous taxane therapeutic agent coating has a clear or transparent appearance.

Spray coating in higher humidity, lower atomization pressure and/or higher temperature conditions, favor the formation of the dihydrate solid form of the taxane therapeutic agent. Methods of coating dihydrate taxane therapeutic agents are provided which comprise the steps of: dissolving solid paclitaxel in ethanol to form a solution, and spraying the solution onto a medical device. When spray coating with the EFD 780S-SS spray valve (EFD, East Providence, R.I.), the spraying step is preferably performed at a temperature of 75° F. or greater, and with a fluid pressure of between about 1.00 and 5.00 psi. For example, dihydrate paclitaxel (dPTX) coatings have been deposited using an EFD 780S-SS spray valve (EFD, East Providence, R.I.) under the following conditions: (1) 4.0 g/L PTX in ethanol spray solution, 44% relative humidity, 12.00 psi atomization pressure, 2.50 psi fluid (tank) pressure and 80° F. ambient temperature; or (2) 4.0 g/L PTX in ethanol spray solution, 55% relative humidity, 5.00 psi atomization pressure, 1.00 psi fluid (tank) pressure and 70° F. ambient temperature.

Electrostatic Spray Coating

Alternatively, the taxane therapeutic agent may be dissolved in a suitable solvent or combination of solvents and then sprayed onto the medical device using an electrostatic spray deposition (ESD) process. The ESD process generally operates on the principle that a charged particle is attracted towards a grounded target. One typical ESD process may be described as follows. The solution that is to be spray coated is typically charged to several thousand volts (typically negative) and the medical device surface held at ground potential. The charge of the spray solution is generally great enough to cause the solution to jump across an air gap of several inches before landing on the surface. As the spray solution is in transit towards the surface, the spray fans out in a conical pattern, promoting formation of a more uniform coating. In addition to the conical spray shape, electrons are further attracted towards the conducting portions of the surface, rather than towards the non-conductive base the medical device surface is mounted on, leaving the coating mainly on the surface only.

During the ESD spray coating process, the spray solution is forced through a capillary subjected to an electrical field. The spray solution leaves the capillary in the form of a fine spray, the shape of which is determined by the electrical field. The medical device is then coated by placing it in the spray and allowing the solvent to evaporate, leaving the desired coating on the surface of the device.

The ESD method allows for control of the coating composition and surface morphology of the deposited coating. In particular, the morphology of the deposited coating may be controlled by appropriate selection of the ESD parameters, as set forth in WO 03/006180 (Electrostatic Spray Deposition (ESD) of biocompatible coatings on Metallic Substrates), the contents of which are incorporated by reference. For example, a coating having a uniform thickness and grain size, as well as a smooth surface, may be obtained by controlling deposition conditions such as deposition temperature, spraying rate, precursor solution, and bias voltage between the spray nozzle and the medical device being coated. The ESD spray solution preferably includes methanol. It is believed that the addition of methanol increases the polarity of the solvent solution, thereby providing a fine spray that is ideal for use in an electrostatic coating process. For example, the spray solution can comprise about 50-80% methanol (by volume), more desirably about 65-75% methanol and most preferably up to about 70% methanol.

Modification of Medical Device Surface to Promote Adhesion of Coating

Optionally, prior to spray coating of the taxane therapeutic agent, the surface of the medical device can be prepared to promote adhesion of the coating material before depositing the coating. Useful methods of surface preparation can include, but are not limited to cleaning; physical modifications such as etching, drilling, cutting, or abrasion; and chemical modifications such as solvent treatment, the application of primer coatings, the application of surfactants, plasma treatment, ion bombardment, covalent bonding and electrochemical methods such as electropolishing, striking, electroplating and electrochemical deposition. Such surface preparation may serve to activate the surface and promote the deposition or adhesion of the coating on the surface. Surface preparation can also selectively alter the release rate of the taxane therapeutic agent. Any additional coating layers can similarly be processed to promote the deposition or adhesion of another layer, to further control the release of the taxane therapeutic agent, or to otherwise improve the biocompatibility of the surface of the layers. For example, plasma treating an additional coating layer before depositing a taxane therapeutic agent thereon may improve the adhesion of the taxane therapeutic agent, increase the amount of taxane therapeutic agent that can be deposited, and allow the taxane therapeutic agent to be deposited in a more uniform layer.

Sterilization of Medical Devices

The medical devices of the present invention can be sterilized prior to implantation into the body, including before and/or after coating. Preferably, the coated medical device is sterilized using a conventional chemical vapor sterilization process that does not undesirably degrade or alter the taxane therapeutic coating. For example, a conventional ethylene oxide (ETO) sterilization process may be used, which may involve exposing the coated medical device to ETO gas at a temperature of about 120° F. for at least a period suitable for sterilizing the medical device. Since ethylene oxide gas readily diffuses through many common packaging materials and is effective in killing microorganisms at temperatures well below those required for heat sterilization techniques, ETO sterilization can permit efficient sterilization of many items, particularly those made of thermoplastic materials, which cannot withstand heat sterilization. The process generally involves placing an item in a chamber and subjecting it to ethylene oxide vapor. When used properly, ethylene oxide is not only lethal to microorganisms, but it is also non-corrosive, readily removed by aeration.

Notably, the ratio of dihydrate to amorphous solid forms of the taxane therapeutic agent may increase during ETO sterilization. For example, increases of up to about 5% in the proportion of dihydrate paclitaxel were observed in coatings consisting of paclitaxel in both the dihydrate and amorphous solid forms prior to sterilization. Typically, coated medical devices can be sterilized within suitable packaging, such as a bag, pouch, tube or mold.

Alternatively, the medical device may be loaded into final packaging, and gamma irradiated in a gamma chamber. In one embodiment, the implantable medical device is irradiated with between 1 and 100 kGy. In another embodiment, the implantable medical device is irradiated with between 5 and 50 kGy, and in yet another embodiment, the implantable medical device is irradiated with between 25 and 28 kGy.

Therapeutic Agent Elution Profile

Local administration of therapeutic agents may be more effective when carried out over an extended period of time, such as a time period at least matching the normal reaction time of the body to an angioplasty procedure, for example. At the same time, it may be desirable to provide an initial high dose of the therapeutic agent over an initial period. For example, local administration of a therapeutic agent over a period of days or even months may be most effective in treating or inhibiting conditions such as restenosis. The coating may be configured to provide a delayed release of the taxane therapeutic agent when the medical device is implanted, permitting the coatings to be configured to provide for the coated taxane therapeutic agent(s) to be released for desirable periods of time. For example, a coating consisting essentially of the taxane therapeutic agent in one or more solid forms can be configured to release less than 90 percent of the coated taxane therapeutic agent into an aqueous environment (such as blood or porcine serum) over a period of at least about 6 months, two months, one month, one week, or one day. In particular, a coating can have an outer layer after conditioning of more than 50% rapidly-dissolving amorphous paclitaxel over a layer of more than 50% slow-dissolving dihydrate paclitaxel. Preferably, the fraction of the coating of the dihydrate paclitaxel is increased during the conditioning process, after deposition of the coating.

The release characteristics of a coated taxane therapeutic agent can be described by an elution profile. The elution profile of a medical device comprising a taxane therapeutic agent shows the percentage of the taxane therapeutic agent that dissolves as a function of time in a given elution medium. The rate of dissolution of the taxane therapeutic agent can vary based on the elution medium being used and the solid form of the taxane therapeutic agent before dissolution. An elution profile can be obtained by any suitable method that allows for measurement of the release of the taxane therapeutic agent from the coating in a manner that can be measured with a desired level of accuracy and precision. In one embodiment, the elution profile of the release of a taxane therapeutic agent is obtained by contacting the medical device with a suitable elution medium. The elution medium can be formulated to simulate conditions present at a particular point of treatment within a body vessel. For example, an elution medium comprising porcine serum can be used to simulate implantation within a blood vessel. The release of taxane therapeutic agent from the medical device can be measured by any suitable spectrographic method, such as measurement of a UV absorption spectrum of the test fluid after contacting the medical device. Typically, the intensity of absorption at characteristic UV absorption peak, such as about 227 nm, can be correlated to the presence and amount of a taxane therapeutic agent in a sample. The amount of taxane therapeutic agent on the medical device can be determined by contacting the medical device with a suitable elution medium and detecting the amount of taxane therapeutic agent released from the medical device into the elution medium.

An elution medium can be selected to solubilize one solid form of a taxane therapeutic agent more rapidly than other solid forms of the taxane therapeutic agent, while allowing for subsequent measurement of the solubilized taxane therapeutic agent in a manner that can be correlated to the amount of the more soluble solid form of the taxane therapeutic agent released from the medical device. Subsequently, a second elution medium can be selected to quickly solubilize one or more other solid forms of the taxane therapeutic agent that did not dissolve in the first elution medium. Preferably, substantially all the taxane therapeutic agent of at least one solid form is removed from the medical device after contact with an elution medium for a desired period of time. The taxane therapeutic agent is subsequently detected in the elution medium. The detection of the taxane therapeutic agent is correlated to the amount of a particular solid form of the taxane therapeutic agent that was present on the medical device surface prior to contacting the medical device with the elution medium.

In one embodiment, the elution profile of a paclitaxel coating on a medical device is determined by first contacting the medical device with a first elution medium that readily dissolves the amorphous paclitaxel at least about 10-times more rapidly than the dihydrate paclitaxel, and then subsequently detecting the amount of taxane therapeutic agent within the elution medium. The medical device is exposed to the first elution medium and the rate of release of the taxane therapeutic agent from the medical device is determined by detecting the taxane therapeutic agent in the first elution medium for a first desired period of time. After the first desired period of time, the amount of taxane therapeutic agent remaining on the medical device can be determined by contacting the medical device with a second elution medium that readily dissolves the dihydrate paclitaxel, and subsequently detecting the amount of taxane therapeutic agent leaving the medical device in the second elution medium.

Any suitable analytical technique(s) may be used to detect a taxane therapeutic agent in an elution medium. Suitable detection methods, such as a spectrographic technique, permit measurement of a property of the elution medium that can be correlated to the presence or concentration of the taxane therapeutic agent with a desired level of accuracy and precision. In one embodiment, absorption spectroscopy (e.g., UV) can be used to detect the presence of a taxane therapeutic agent, such as in an elution medium. Accordingly, the Beer-Lambert Correlation may be used to determine the concentration of a taxane therapeutic agent in a solution. This correlation is readily apparent to one of ordinary skill in the art, and involves determining the linear relationship between absorbance and concentration of an absorbing species (the taxane therapeutic agent in the elution medium). Using a set of standard samples with known concentrations, the correlation can be used to measure the absorbance of the sample. A plot of concentration versus absorbance can then be used to determine the concentration of an unknown solution from its absorbance. UV absorbance of the taxane therapeutic agent at 227 nm can be measured (see FIG. 2), and the absorbance at this wave length can be correlated to concentration of the taxane in the test solution.

FIG. 6A shows elution profiles 700 for two medical devices in porcine serum elution media at 37° C. The first elution profile 710 was obtained from a first coated vascular stent coated with a single layer of amorphous paclitaxel. The second elution profile 720 was obtained from a second coated vascular stent coated with a single layer of dihydrate paclitaxel. The amorphous paclitaxel coating on the first vascular stent had a clear, transparent visual appearance, while the dihydrate paclitaxel coating on the second vascular stent had an opaque, white and cloudy visual appearance. Referring to the first elution profile 710, obtained from the amorphous paclitaxel coating, 100% of the amorphous paclitaxel dissolved within about 6.5 hours (400 minutes), while less than 40% of the second (dihydrate) coating eluted under the same conditions after about 24 hours.

A preferred first elution medium is an aqueous solution comprising 0.1% to about 10% of a cyclodextrin. In one aspect, an elution profile may be obtained by contacting a coated medical device comprising a taxane therapeutic agent with an elution medium comprising a cyclodextrin. A cyclodextrin is a cyclic oligosaccharide formed from covalently-linked glucopyranose rings defining an internal cavity. The diameter of the internal axial cavity of cyclodextrins increases with the number of glucopyranose units in the ring. The size of the glucopyranose ring can be selected to provide an axial cavity selected to match the molecular dimensions of a taxane therapeutic agent. The cyclodextrin is preferably a modified beta-cyclodextrin, such as Heptakis-(2,6-di-O-methyl)-β-cyclodextrin (HCD). Suitable cyclodedtrin molecules include other β-cyclodextrin molecules, as well as γ-cyclodextrin structures.

The elution medium comprising a cyclodextrin can dissolve a taxane therapeutic agent so as to elute the taxane therapeutic agent from a medical device coating over a desired time interval, typically about 24 hours or less (less than comparable elution times in porcine serum). Preferably, the cyclodextrin elution medium is formulated to provide distinguishable elution rates for different coating configurations, providing different elution profiles for different solid forms of a taxane therapeutic agent in the coating. The elution medium may be contacted with a medical device comprising a taxane therapeutic agent, such as paclitaxel, in any manner providing an elution profile indicative of the arrangement of the taxane therapeutic agent molecules in the coating. For example, the elution medium may contact a medical device coating in a continuous flow configuration, or in a batch testing configuration.

Figure 6B:
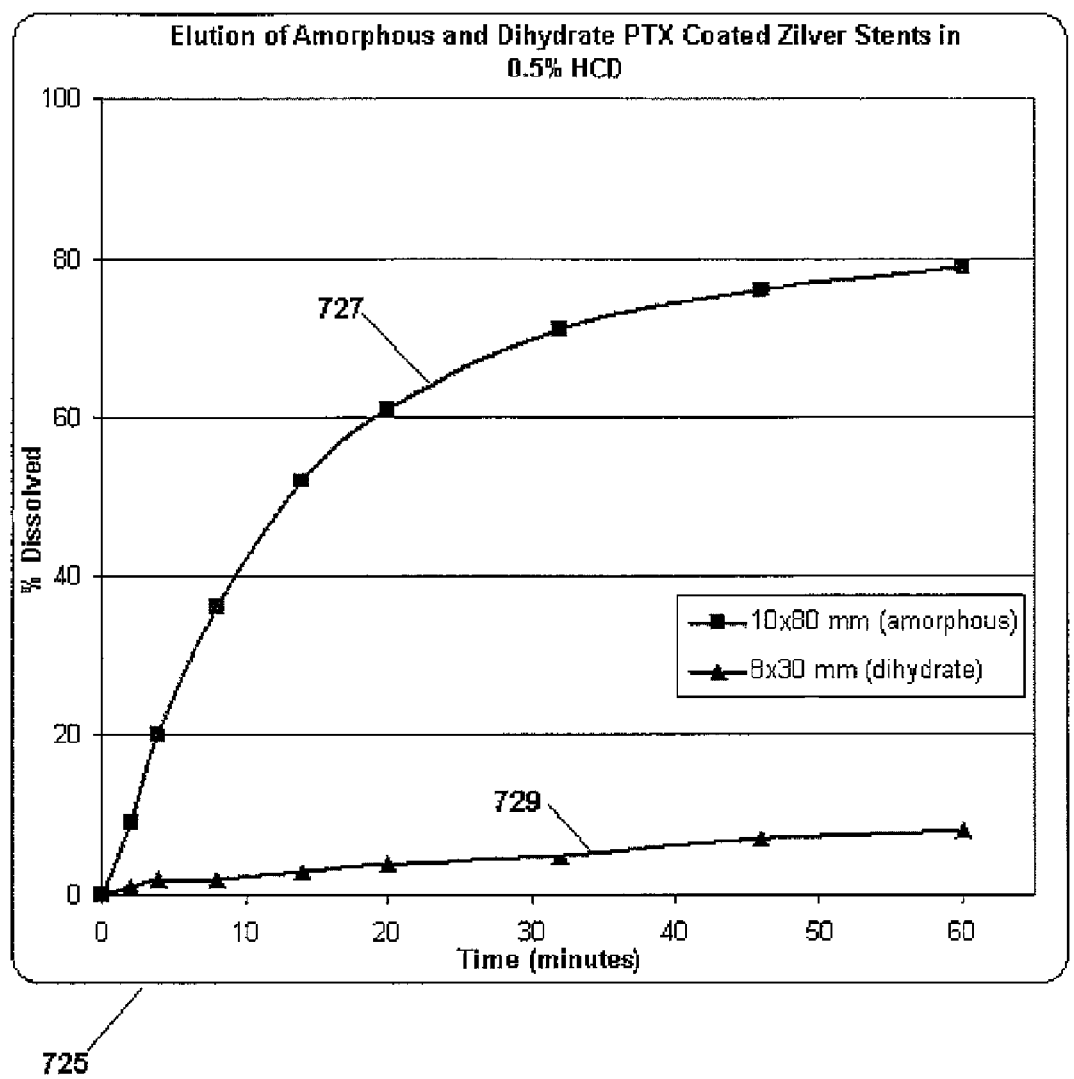
FIG. 6B shows elution profiles for coatings each comprising different amounts of the amorphous and dihydrate solid forms of paclitaxel eluting in porcine serum.

Taxane therapeutic agents typically have different elution profiles in different elution media. FIG. 6B shows elution profiles 725 for the first and second vascular stents in a 0.5% w/w aqueous solution of Heptakis-(2,6-di-O-methyl)-β-cyclodextrin (HCD) elution medium at 25° C. The first elution profile 727 was obtained from the first coated vascular stent coated with a single layer of amorphous paclitaxel. The second elution profile 729 was obtained from the second coated vascular stent coated with a single layer of dihydrate paclitaxel. Referring to the first elution profile 727, obtained from the amorphous paclitaxel coating, about 80% of the amorphous paclitaxel dissolved within about 1 hour, while less than 20% of the dihydrate paclitaxel was released within 1 hour in the second elution profile 729. Accordingly, comparing FIGS. 6A and 6B, both the HCD and porcine serum elution media selectively dissolved the amorphous paclitaxel distinguishably more rapidly than the dihydrate paclitaxel, however the HCD elution medium dissolved the amorphous paclitaxel much more quickly (727) than the porcine serum (710).

Figure 6C:
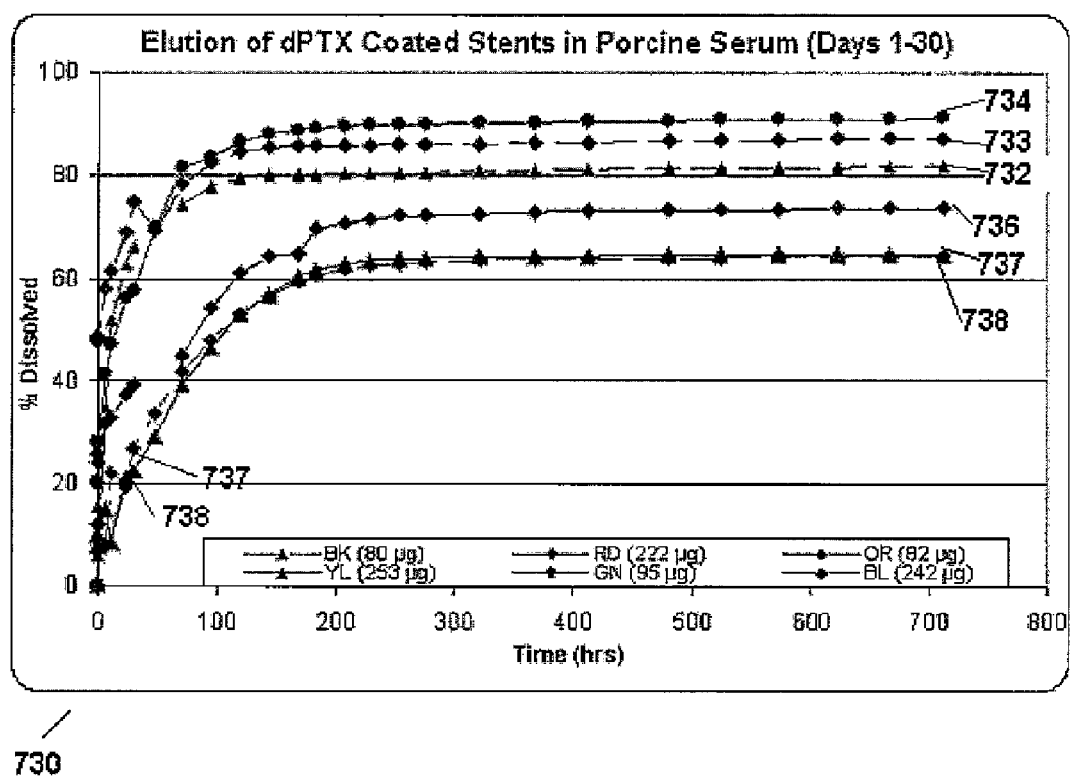
FIG. 6C shows elution profiles for several different coatings having different amounts of the amorphous and dihydrate solid forms of paclitaxel eluting in an aqueous solution comprising Heptakis-(2,6-di-O-methyl)-β-cyclodextrin (HCD).

FIG. 6C shows elution profiles 730 for six medical devices in porcine serum elution media at 37° C. for 30 days. All six medical devices were coated with a single layer of paclitaxel in various solid forms, without a polymer or any release-rate-modifying substance. A first elution profile 732, a second elution profile 733 and a third elution profile 734 were obtained coated vascular stents coated with a single layer of about 1 micrograms/mm$^2$ (±15%) paclitaxel layer with about 70% of the paclitaxel in the less soluble dihydrate solid form and about 30% of the paclitaxel in the more soluble amorphous solid form. Notably, increasing the total amount of paclitaxel in the single-layer coating from 80 micrograms in the first elution profile 732 to 82 micrograms in the second elution profile 733 to 95 micrograms in the third elution profile 734 resulted in a steady increase in the elution rate. A third elution profile 736, a fifth elution profile 737 and a sixth elution profile 738 were obtained coated vascular stents coated with a single layer of about 3 micrograms/mm$^2$ (±15%) paclitaxel layer with about 80% of the paclitaxel in the dihydrate solid form and about 20% of the paclitaxel in the amorphous solid form. Again, increasing the total amount of paclitaxel in the single-layer coating from 222 micrograms in the fourth elution profile 736 to 242 micrograms in the sixth elution profile 738 to 253 micrograms in the fifth elution profile 737 resulted in a steady increase in the elution rate. The rate of elution from the 3 micrograms/mm$^2$ paclitaxel coatings was slower than the rate of elution from the 1 micrograms/mm$^2$ coatings because the amount of the paclitaxel in the less soluble dihydrate solid form was increased from 70% in the 1 microgram/mm$^2$ paclitaxel coatings to 80% in the 3 micrograms/mm$^2$ paclitaxel coatings. Accordingly, the rate of release of a paclitaxel coating can be varied by changing the amount of each solid form of the paclitaxel present in a coating. Thus, by varying the solid form of a taxane therapeutic agent, a lower dose of paclitaxel can be used to provide a more sustained release than a higher dose of paclitaxel, without introducing a polymer to the coating.

Figure 7A:
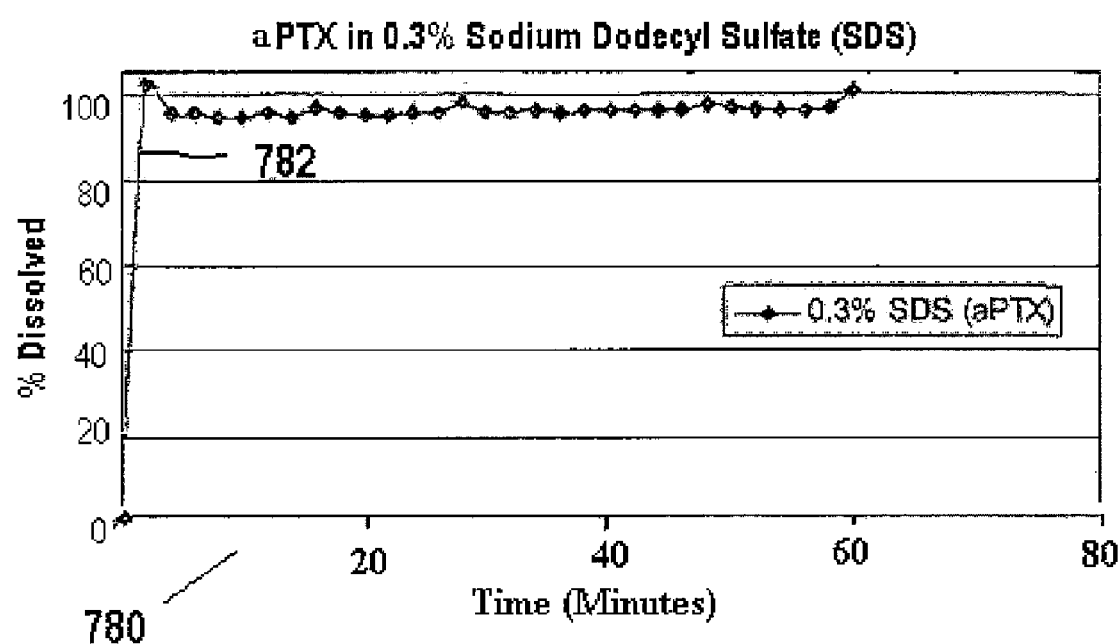
FIG. 7A shows an elution profile for a coating of the amorphous solid form of paclitaxel eluting in sodium dodecyl sulfate (SDS).
Figure 7B:
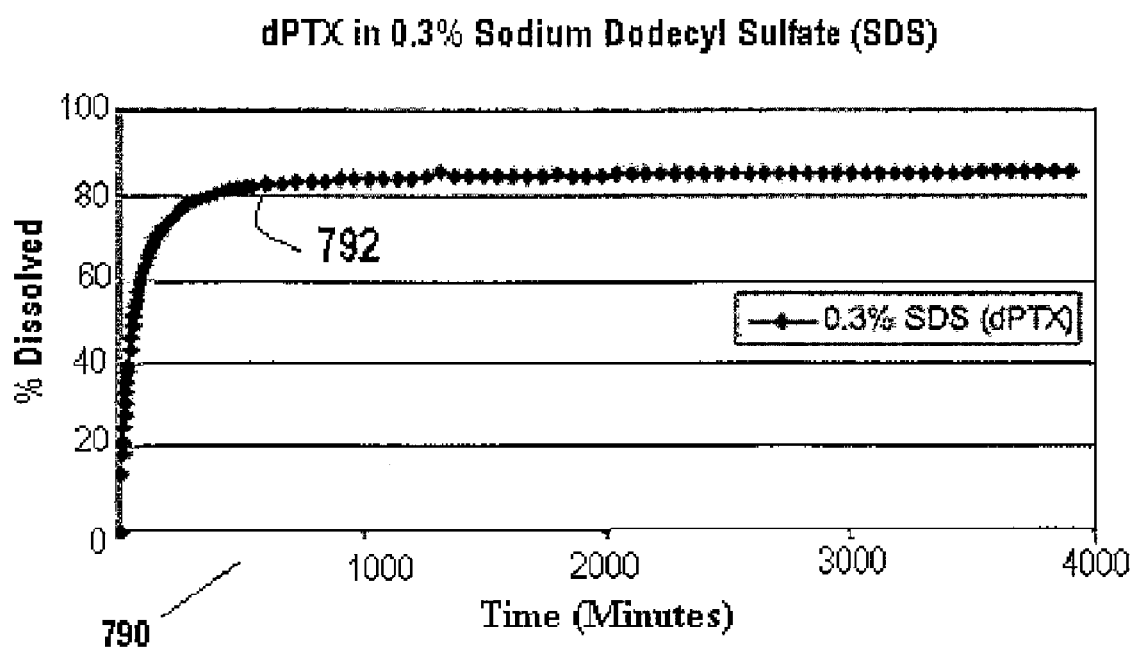
FIG. 7B shows the elution profile for a coating of the dihydrate solid form of paclitaxel eluting in sodium dodecyl sulfate (SDS).

Taxane therapeutic agents can have different elution profiles in different elution media. Another suitable elution medium for taxane therapeutic agent is sodium dodecyl sulfate (SDS). FIG. 7A shows the solubility of amorphous paclitaxel in sodium dodecyl sulfate (SDS). FIG. 7A is a graph 780 showing a first elution profile 782 obtained from a first coated vascular stent coated with a single layer of amorphous paclitaxel (aPTX) in 0.3% SDS elution medium at 25° C. FIG. 7B shows the solubility of dihydrate paclitaxel in sodium dodecyl sulfate (SDS). FIG. 7B is a graph 790 showing a second elution profile 792 obtained from a second coated vascular stent coated with a single layer of dihydrate paclitaxel (dPTX) in the same 0.3% SDS elution medium at 25° C. The rate of elution of amorphous paclitaxel in the first elution profile 782 is more rapid than the rate of elution of the dihydrate paclitaxel in the second elution profile 792. However, both solid forms of paclitaxel are significantly more soluble in the 0.3% SDS elution medium than in the porcine serum elution media (e.g., compare FIG. 6A and FIGS. 7A-7B).

Figure 8A:
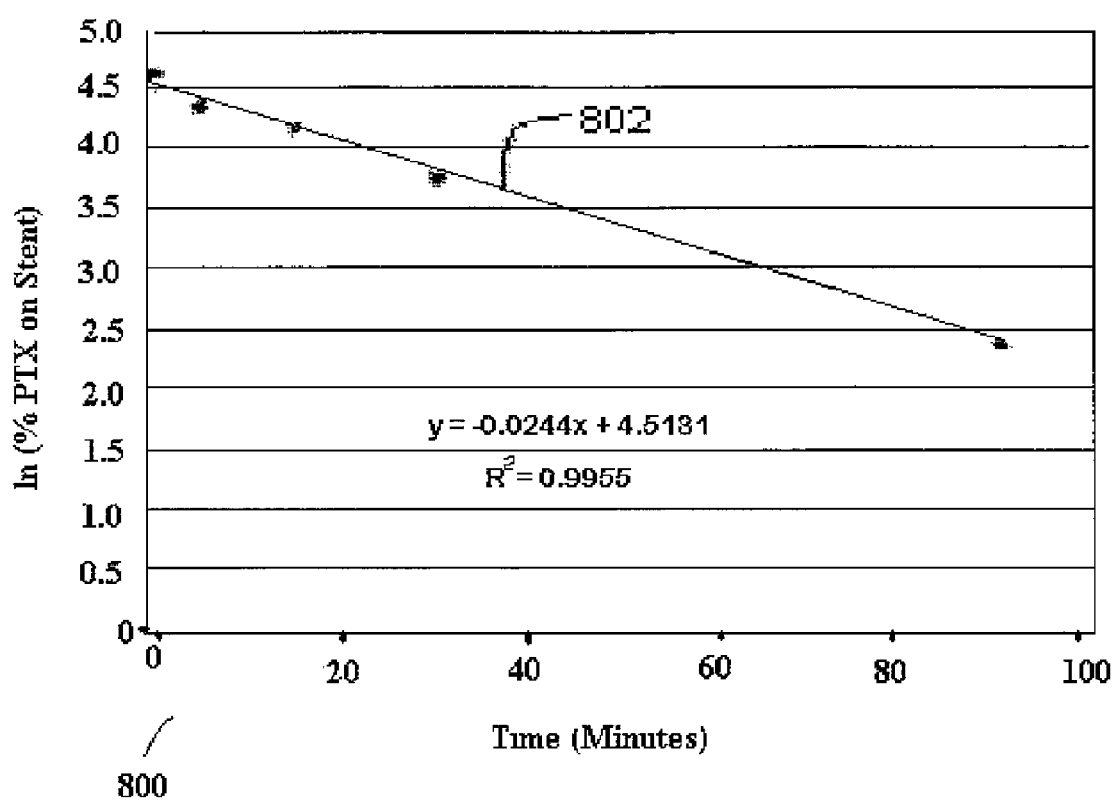
FIG. 8A is a kinetic plot for the dissolution of amorphous paclitaxel in porcine serum.

FIG. 8A shows a first-order kinetic plot 800 of the data from the first elution profile 710 in FIG. 6A. The first kinetic plot 800 plots the natural log of the percent of the amorphous paclitaxel coating remaining on the first vascular stent as a function of time (minutes). The data in the first kinetic plot 800 closely fits to straight line 802 ($R^2$=0.9955), indicating that the elution of amorphous paclitaxel in porcine serum at 37° C. follows first order kinetics. Based on the slope of the line 802, the first order rate constant of amorphous paclitaxel in porcine serum (37° C.) is about 0.0244 $min^{-1}$, with a half life of about 30 minutes.

Figure 8B:
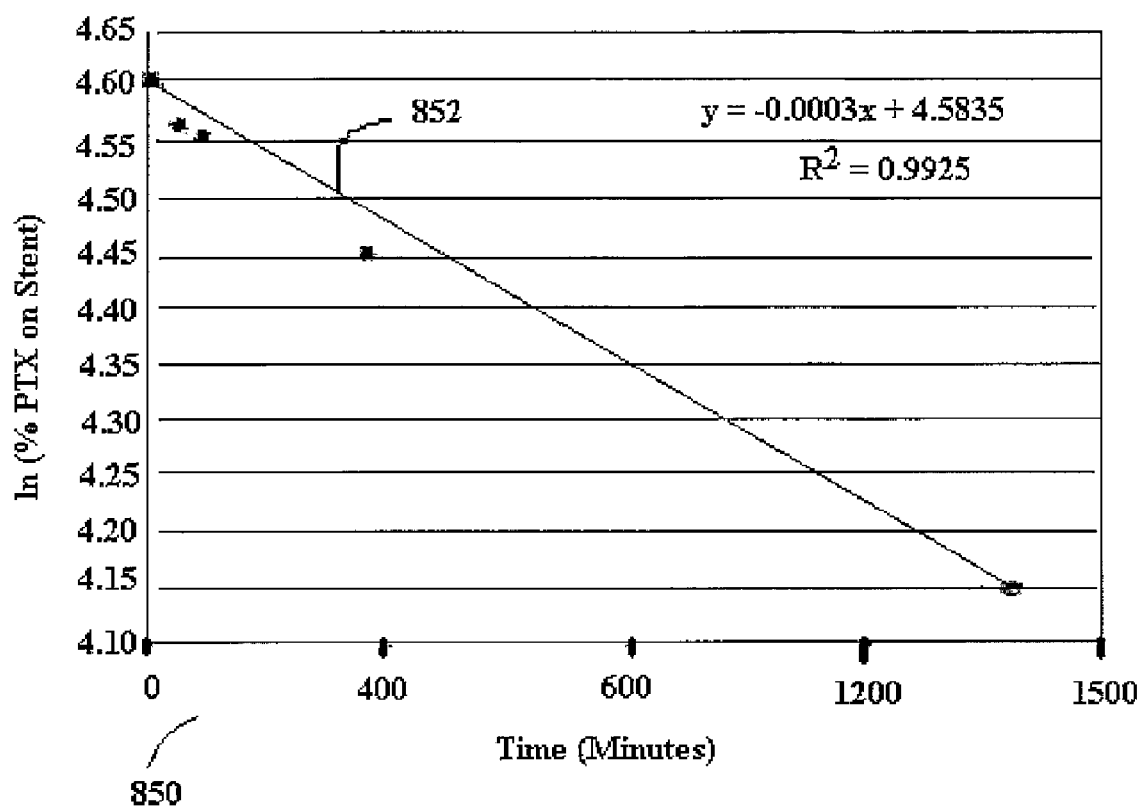
FIG. 8B is a kinetic plot for the dissolution of dihydrate paclitaxel in porcine serum.

Similarly, FIG. 8B shows a first-order kinetic plot 850 of the data from the second elution profile 720 in FIG. 6A. The kinetic plot 850 indicates the natural log of the percent of the dihydrate paclitaxel coating remaining on the second vascular stent as a function of time (minutes). The data in the first kinetic plot 850 also closely fits to straight line 852 ($R^2$=0.9925), indicating that the elution of dihydrate paclitaxel in porcine serum at 37° C. also follows first order kinetics. Based on the slope of the line 852, the first order rate constant of dihydrate paclitaxel in porcine serum (25° C.) is about 0.0003 $min^{-1}$, with a half life of about 38.5 hours (2,310 minutes). Therefore, the rate of elution of the amorphous paclitaxel is about 100-times faster than dihydrate paclitaxel in porcine serum (25° C.).

Figure 9:
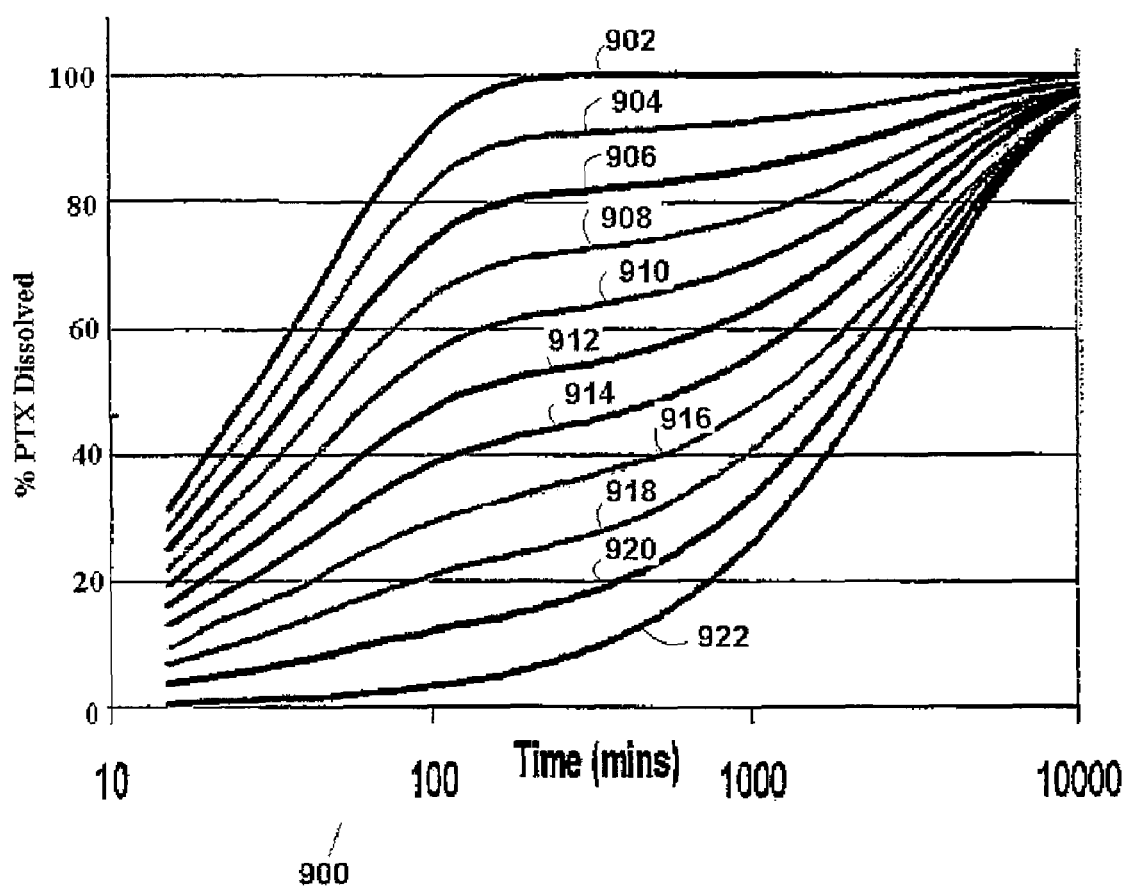
FIG. 9 is a graph of calculated (predicted) porcine serum solubility of a paclitaxel coating comprising varying amounts of the dihydrate paclitaxel and the amorphous paclitaxel in varying proportions.

Based on the first order rate constants obtained for amorphous paclitaxel ($k_1$=0.0244 $min^{-1}$) and for dihydrate paclitaxel ($k_2$=0.0003 $min^{-1}$), the rate of dissolution of a coating comprising of a mixture of amorphous and dihydrate taxane therapeutic agents can be formulated as a function of the proportion of each solid form by the formulae: $f=1-(ae^{k_1 t}+(1-a)e^{k_2 t})$ and $a=(1-f-e^{k_2 t})/e^{k_1 t}-e^{k_2 t}$, where f is the fraction dissolved, $k_1$ and $k_2$ are the rate constants for amorphous and dihydrate paclitaxel respectively, a is the proportion of amorphous taxane therapeutic agent in the coating layer, (1−a) is the amount of dihydrate taxane therapeutic agent in the coating layer and e is the natural logarithmic base. FIG. 9 shows a plot of the predicted dissolution of a mixture of amorphous paclitaxel and dihydrate paclitaxel having the first order rate constants $k_1$, and $k_2$ respectively as a function of time and composition. A first trace 904 corresponds to the predicted dissolution profile of a coating comprising 10% amorphous paclitaxel (aPTX) and 90% dihydrate paclitaxel (dPTX). The composition corresponding to the traces of FIG. 9 is provided in Table 5 below. The percentage of the paclitaxel dissolved as a function of time for about 1 week (10,000 minutes) is shown for each trace.

TABLE 5

Compositions of predicted elution profiles shown in FIG. 8

| Trace in FIG. 9 | Percentage aPTX | Percentage dPTX |
|---|---|---|
| 902 | 100 | 0 |
| 904 | 90 | 10 |
| 906 | 80 | 20 |
| 908 | 70 | 30 |
| 910 | 60 | 40 |
| 912 | 50 | 50 |
| 914 | 40 | 60 |
| 916 | 30 | 70 |
| 918 | 20 | 80 |
| 920 | 10 | 90 |
| 922 | 0 | 100 |

Preferably, the conditioning step(s) increase the amount of a hydrated solid form (such as the dihydrate solid form) within the coating. Accordingly, the conditioning step(s) may change the composition of a taxane therapeutic coating from a pre-conditioning composition represented by any composition corresponding to traces 902-920 to a composition represented by a higher-numbered trace. For example, a pre-conditioned coating consisting essentially of paclitaxel in mixture of solid forms corresponding to trace 906 may be conditioned prior to implantation to provide a coating corresponding to the slower-eluting trace 918. Varying the relative amounts of amorphous and dihydrate paclitaxel in the coating by conditioning can result in wide variation of the rate of release of paclitaxel from the coating. Referring again to FIG. 9, after about 1-2 hours (100 minutes), less than 10% of the dihydrate paclitaxel coating (922) has dissolved, while about 80% of the amorphous paclitaxel coating (902) has dissolved. Mixtures of amorphous and dihydrate paclitaxel (904-920) can show intermediate amounts of elution. Similarly, after about 16 hours (1,000 minutes), less than 30% of the dihydrate paclitaxel coating (922) has dissolved, about 100% of the amorphous paclitaxel coating (902) has dissolved and mixtures of amorphous and dihydrate paclitaxel (904-920) can show intermediate amounts of elution. Finally, after about 1 week (10,000 minutes), about 90-95% of the dihydrate paclitaxel coating (922) has dissolved, with mixtures of amorphous and dihydrate paclitaxel (904-920) showing nearly 100% elution.

The elution profiles of coatings modeled by the traces of FIG. 9 correspond to coatings having a taxane therapeutic agent distributed in a mixture of multiple solid forms within the coating, most preferably a coating formed from a mixture of amorphous state paclitaxel and a solvated (e.g., dihydrate) solid form paclitaxel. A coating having a mixture of the amorphous and taxane therapeutic agent solid forms can be prepared as described above with respect to the third embodiment.

The dihydrate paclitaxel taxane therapeutic agent is also less soluble than the amorphous taxane therapeutic agent or the anhydrous taxane therapeutic agent. In porcine serum at 37° C., samples of the dihydrate paclitaxel solid form were about 100-times less soluble than samples of the anhydrous paclitaxel solid form. Other studies have reported decreased solubility of dihydrate paclitaxel in water at 37° C. compared to anhydrous paclitaxel. Anhydrous paclitaxel is reported with a solubility of about 3.5 μg/mL after about 5 hours in 37° C. water, while dihydrate paclitaxel has a solubility of less than 1.0 μg/mL in 37° C. water over the same time period. R.

T. Liggins et al., "Solid-State Characterization of Paclitaxel," *Journal of Pharmaceutical Sciences*, v. 86, No. 12, 1458-1463 (December 1997).

Coating Durability

The conditioned coatings preferably comprise a taxane therapeutic agent with a desired level of durability for an intended use. Coating durability describes the resistance of a coating to loss of integrity due to abrasion, bending or mechanical loading through mechanisms such as flaking, cracking, chipping and the like. Coatings consisting of dihydrate taxane therapeutic agents demonstrated a low durability, and a high propensity for dissociation from the stent coating upon crimping. In contrast, the amorphous solid form of the taxane therapeutic agents demonstrated greater durability and substantially lower tendency to dissociate from a coated stent upon crimping of the stent. In aqueous media such as porcine serum and blood, the amorphous taxane therapeutic agent solid form is more soluble than the dihydrate taxane therapeutic agent. Therefore, the release rate and the durability of the coating can be altered during the conditioning step(s) by altering the fraction of dihydrate or amorphous solid forms of the taxane therapeutic agent in one or more coating layers.

The pre-conditioned coatings may be more durable than the conditioned coatings. Conditioned coatings preferably retain enough durability for an intended use (e.g., to prevent undesirable flaking or release of the taxane therapeutic agent from the coating prior to implantation), but have a slower rate of elution upon implantation than the unconditioned coating. For example, the conditioned coating preferably retains a suitable amount of an amorphous taxane therapeutic agent solid form to impart a desired durability to the coating. For example, the outer layer of a conditioned coating can comprise at least about 5, 10, 15, 20, 25, 30, 35, 40, 45, 50, 60, 70, 80%, or more, of an amorphous taxane therapeutic agent to impart durability to a coating. For sustained release coatings, durability may be balanced with the goal of extending the elution time by adding more of the slower-eluting dihydrate taxane therapeutic agent.

The durability of a coating can be measured by weighing a coated medical device prior to physical agitation of the coating by a test process such as crimping, shaking, freezing or abrading the stent, weighing the coated stent a second time after the test process is performed, and comparing the second weight to the first weight. For a given physical test procedure, coating durability can be quantified by the amount of weight loss from the first weight to the second weight. Accordingly, the lower the amount of weight loss as a result of performing a physical test on the coated medical device, the more durable the coating is. One preferred physical test for implantable coated vascular stents is the process of crimping the stent from an expanded state (in which the stent is coated), to a radially compressed state for delivery within a body vessel. The durability of a radially expandable medical device can be quantified as the percentage weight loss of the coated medical device before and after crimping the medical device.

The difference in weight of a coated stent before and after crimping provides one indicator of the coating durability. Preferably, the coated medical device is crimped prior to conditioning. Highly durable coatings typically have a lower weight loss during the crimping process. Taxane coatings with a higher proportion of dihydrate are typically less durable (i.e., higher weight loss during the crimping process). Preferred pre-conditioned taxane coatings exhibit a coating weight loss of less than about 10%, more preferably less than about 8%, 6%, 4%, 3%, 2%, 1% or 0.5% and most preferably less than about 0.1% before and after crimping to a diameter of 6 French (6 F). The coating weight loss can be measured by: (1) weighing an uncoated stent in the radially expanded state to obtain a first weight ("weight (1)"), (2) coating the stent in the expanded condition, (3) weighing the coated stent to obtain a second weight ("weight (2)"), (4) crimping the coated stent and (5) weighing the crimped, coated stent to obtain a third weight ("weight (3)"). The coating weight loss is: [weight (2)–weight (1)]–[weight (3)–weight (1)], or simply weight (2)–weight (3). Accordingly, one particularly preferred coating comprises a mixture of amorphous taxane therapeutic agent and dihydrate taxane therapeutic agent. Coatings comprising mixtures of dPTX with at least about 25-50% aPTX on the outside surface of the coating have shown desired durability characteristics.

The crimped coated medical device is preferably conditioned in the crimped state, prior to, during or after packaging. For example, the coated medical device may be crimped and conditioned during ETO sterilization, or within a sealed package. As discussed above, increasing the proportion of dPTX during conditioning decreases the elution rate of the coating while also decreasing the durability of the coating. Particularly preferred coatings applied with a 4.68 mM paclitaxel solution comprise about 30% aPTX and 70% dPTX after conditioning. These preferred ratios may be altered through the conditioning process. For example, a stent comprising a 30:70 aPTX:dPTX was coated in a radially expanded state, crimped to fit a delivery catheter, and re-weighed prior to conditioning. This 30:70 aPTX:dPTX coated stent lost less than 5% weight as a result of crimping to a 6 F size.

The durability of the coating may also be evaluated as the resistance to displacement of the coating in response to mechanical abrasion. For instance, scraping a non-durable coating may displace a portion of the coating from one area to another, resulting in a scratching or pitting of the surface without a net change in the weight of the coating. Preferably, coatings are sufficiently durable to resist displacement by mechanical abrasion as well as weight loss. Preferred coatings have a substantially uniform and smooth surface. Most preferably, coatings maintain a surface roughness (peak to valley) that is less than 50%, preferably 25%, of the total thickness of the coating. For instance, for a 10 micrometer thick coating, the surface is preferably not more than about 5 micrometers from its highest peak to its lowest valley. Also preferably, the coating roughness does not increase as a result of mechanical abrasion of a type encountered in crimping and loading the coated medical device into a delivery catheter.

Stents with coatings comprising a mixture of taxane therapeutic agents in the dihydrate solid form and in the amorphous form were prepared by: preparing a paclitaxel solution comprising a solvent comprising ethanol (e.g, to form a coating with a high fraction of the amorphous solid form) or methanol and water (e.g., to form a coating with a higher fraction of dihydrate or other solvated solid forms) to form a 2.4 mM paclitaxel solution (see Table 2 above for preferred solvent compositions), and spraying the paclitaxel solution onto a stent with an ultrasonic spray gun (Sono-tek Model 8700-60) using a 60 kHz nozzle at a flow rate of 0.03-0.10 mL/min, a coating velocity of 0.02-0.08 in/sec, a nozzle power of 1.4 W, a process gas pressure of 0.5-1.0 psi, and a distance from the nozzle to the stent of about 5-10 mm, while rotating the stent with an axial rotation rate of 50-70 rpm.

The composition of a coating comprising a mixture of aPTX and dPTX can be determined by differential elution of each of the solid forms in series. One preferred method of determining the composition of a coating comprises a destructive testing method, whereby a medical device coated with a taxane therapeutic agent is placed in contact with a first elution media, such as porcine serum, that dissolves one solid form of the taxane therapeutic agent at a much faster rate than other solid forms of the taxane therapeutic agent. The presence of the taxane therapeutic agent can be determined by measuring the absorption of the first elution medium at 227 nm, as discussed with respect to FIG. 2. The strength of absorption of the taxane therapeutic agent in the first elution medium can be correlated to the amount of the first solid form of the taxane therapeutic agent in the original coating. Similarly, the amount of absorption in the second elution medium can be correlated to the amount of the second solid form of the taxane therapeutic agent in the original coating. In addition, two stents coated in the same manner can be independently contacted with the first medium or the second medium, and the amount of taxane therapeutic agent elution in each medium can be compared.

For example, porcine serum can be used as a first elution medium to determine the amount of aPTX in a coating. The rate constant for aPTX in porcine serum is about 100-times the rate constant for dPTX in porcine serum. Accordingly, when a medical device coated with a mixture of aPTX and dPTX is placed in a stream of flowing porcine serum, aPTX will elute more rapidly than dPTX, and the downstream absorption of paclitaxel in the elution stream can be correlated to the amount of aPTX in the original coating. The elution medium can be analyzed with HPLC after contacting the coating to quantify the amount of paclitaxel eluted from the coating. SDS may be used as a second elution medium, to rapidly elute the remaining dPTX from the medical device coating. Measuring the amount of paclitaxel in the SDS stream by absorption by HPLC can be correlated to the amount of dPTX in the original coating.

Preferably, the coated medical device can be contacted with a modified porcine serum elution medium at a constant flow rate of 16 mL/min for a desired period of time (e.g., 6-24 hours) sufficient to elute the aPTX present on the stent. The percentage of the taxane therapeutic agent dissolved can be measured as a function of time by monitoring the optical density of the first elution medium at 227 nm after contacting the coated stent, as described above. The modified porcine serum elution medium can be prepared by adding 0.104 mL of a 6.0 g/L Heparin solution to porcine serum at 37° C. and adjusting the pH to 5.6+/−0.3 using a 20% v/v aqueous solution of acetic acid. The elution rate profile of the taxane therapeutic agent can be measured for any desired period, and correlated to the amount of aPTX in the coating. Subsequently, the coated medical device is contacted with a second elution medium comprising 0.3% sodium dodecyl sulfate (SDS) at 25° C. a constant flow rate of 16 mL/min for a suitable time period to elute the dPTX present in the coating. The elution rate profile of the taxane therapeutic agent can be measured for any desired period, and correlated to the amount of aPTX (e.g., by elution in porcine serum) and dPTX (e.g., by subsequent elution in SDS) in the coating.

FIGS. 10A-13B are optical micrographs of durable paclitaxel coatings on stents comprising various mixtures of dPTX and aPTX. The ratio of amorphous to dihydrate paclitaxel in each coating was subsequently determined by monitoring a characteristic paclitaxel UV absorption peak (e.g., 227 nm) in an elution media in contact with the paclitaxel coated stents. This determination was performed by sequentially dissolving the coating in two different elution media separately contacted with the coating. First, the paclitaxel coating was contacted with stream of a first elution medium (a 0.5-1.0% w/w aqueous HCD solution) in which the amorphous solid form of paclitaxel is substantially more soluble than the dihydrate solid form of paclitaxel. Second, after elution of the paclitaxel from the stents in the first elution medium, the remaining paclitaxel coating (presumed to be the more soluble dihydrate) was contacted with a stream of a second elution medium (ethanol or a 0.3% w/w aqueous Sodium Dodecyl Sulfate solution), in the absence of the first elution medium, effective to readily dissolve the dihydrate solid form paclitaxel in the coating. Based on the comparative solubility of the dPTX and aPTX solid forms in the first and second elution media (see, e.g., FIG. 7A and FIG. 7B), the concentration of paclitaxel in the elution media was measured by UV detection (at 227 nm) to determine the ratio of paclitaxel solid forms originally present in the taxane coatings on the stents.

Figure 10A:
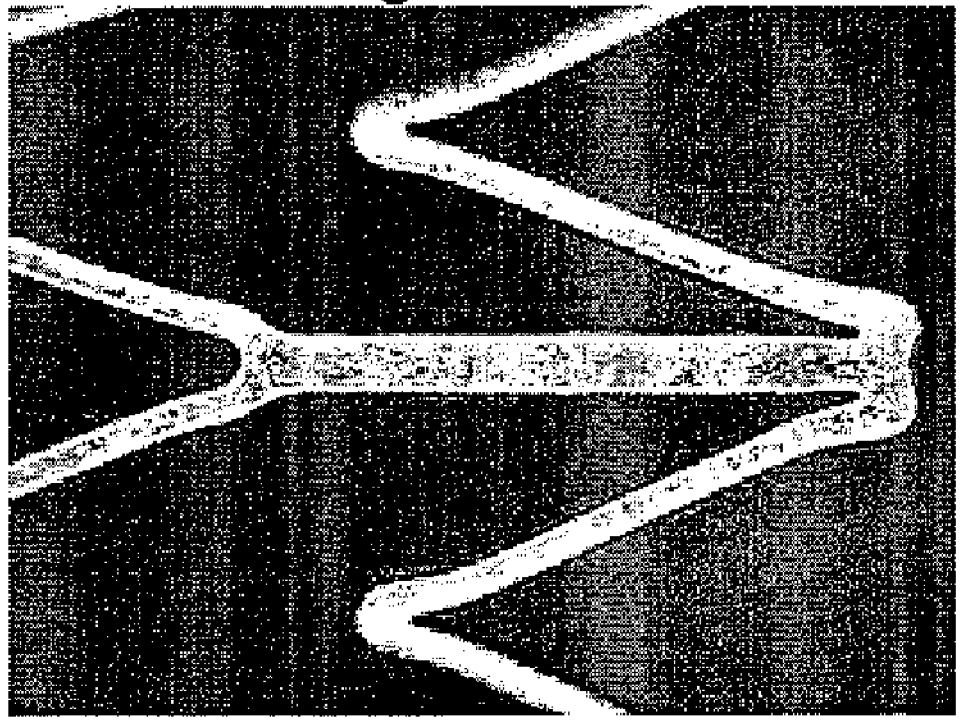
FIG. 10A and FIG. 10B are optical micrographs of a paclitaxel coated stent.
Figure 10B:
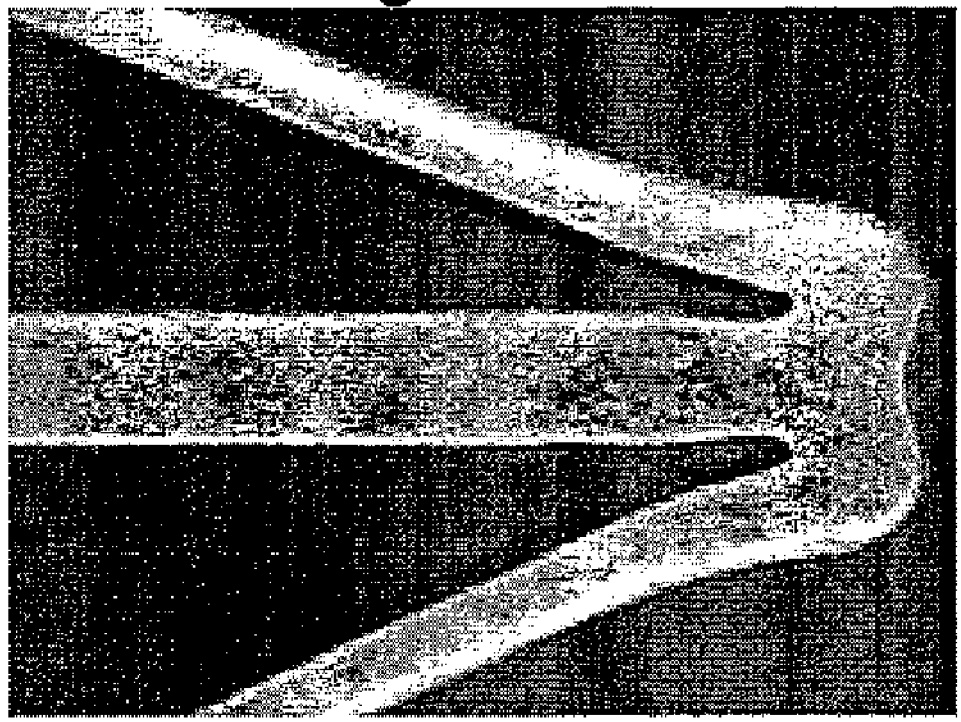

A mixture of amorphous and dihydrate taxane therapeutic agent coating has a cloudy or spotted appearance (clear coating with white opaque regions). FIG. 10A shows a 50× optical micrograph of a metal stent coated with about 65% dihydrate paclitaxel (35% amorphous paclitaxel) coating prepared by ultrasonic spray coating a 4.68 mM paclitaxel solution in a 93% v methanol (7% water) solvent. FIG. 10B shows a 115× optical micrograph of the coating shown in FIG. 10A. The 65:35 dPTX:aPTX coating has a largely cloudy and spotty appearance due to the presence of the dihydrate solid form of paclitaxel. Opaque white regions appear in the coating due to the mixture of the dihydrate (opaque, white) with lesser amounts of the amorphous (clear) solid form of paclitaxel.

Figure 11A:
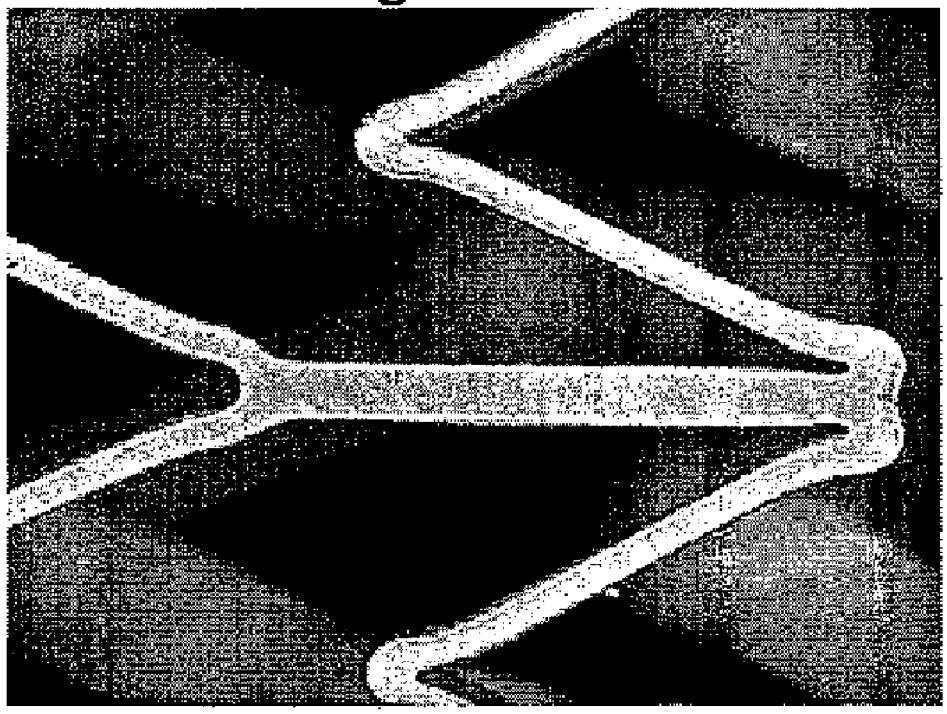
FIG. 11A and FIG. 11B are optical micrographs of a paclitaxel coated stent.
Figure 11B:
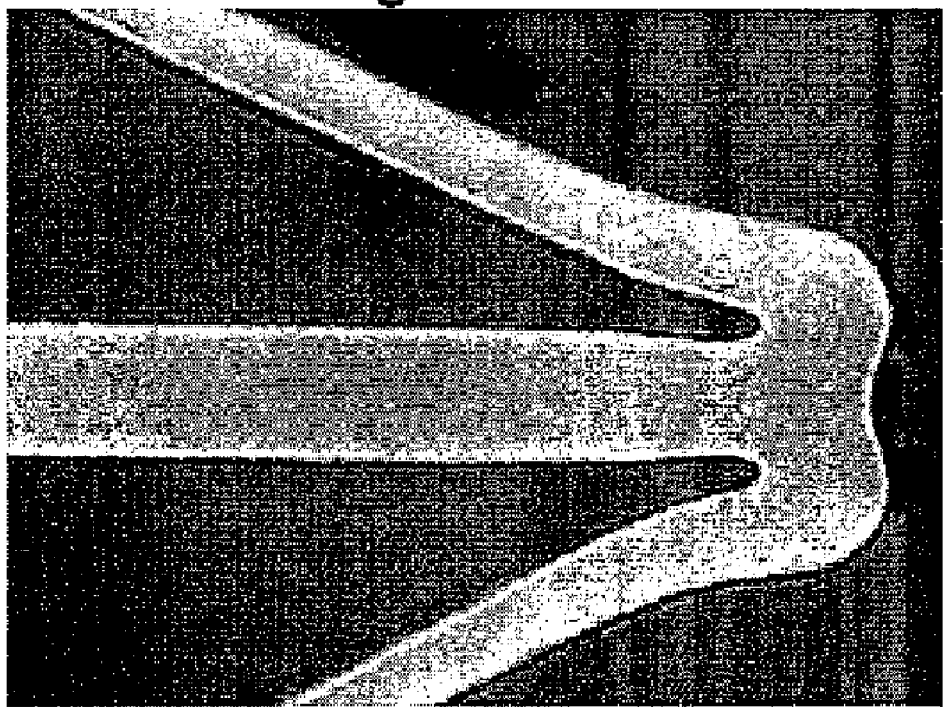

FIG. 11A shows a 50× optical micrograph of a metal stent coated with about 48% dihydrate paclitaxel and about 52% amorphous paclitaxel coating prepared by ultrasonic spray coating a 4.71 mM paclitaxel solution in a 93% w/w methanol (7% w/w water) solvent. FIG. 11B shows a 115× optical micrograph of the coating shown in FIG. 11A. The 48:52 w/w dPTX:aPTX coating has a total dose of paclitaxel of about 3 micrograms per $mm^2$, as well as a clearer and less spotty appearance compared to the coating in FIGS. 10A-10B due to a more uniform distribution of the amorphous solid form of paclitaxel. Regions of varying opacity in the coating result from the non-uniform mixture of the amorphous solid form of paclitaxel with the dihydrate (opaque) solid form.

Figure 12A:
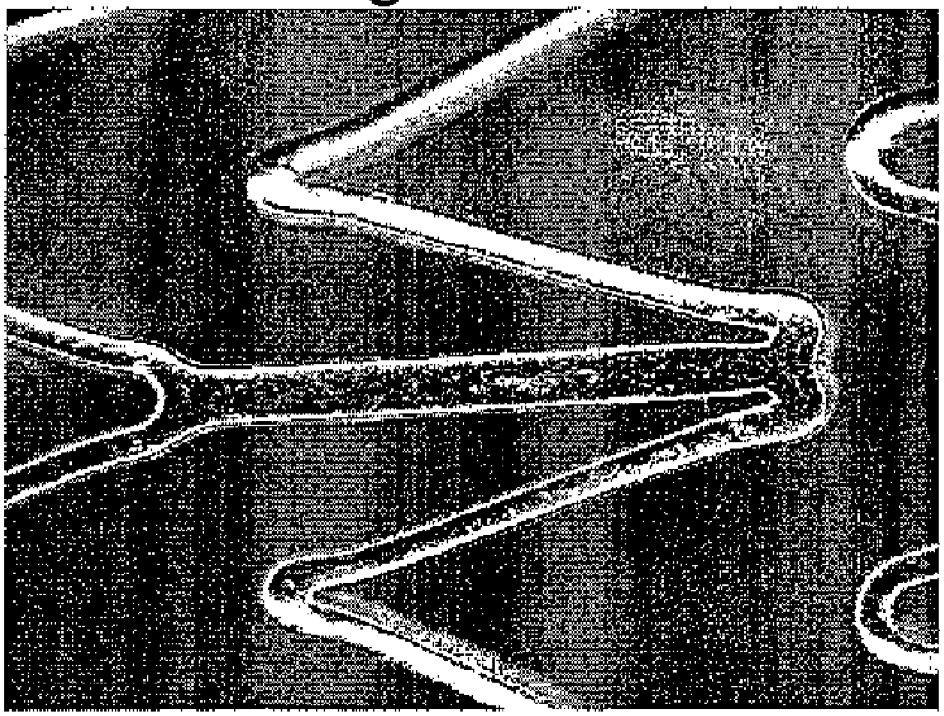
FIG. 12A and FIG. 12B are optical micrographs of a paclitaxel coated stent.
Figure 12B:
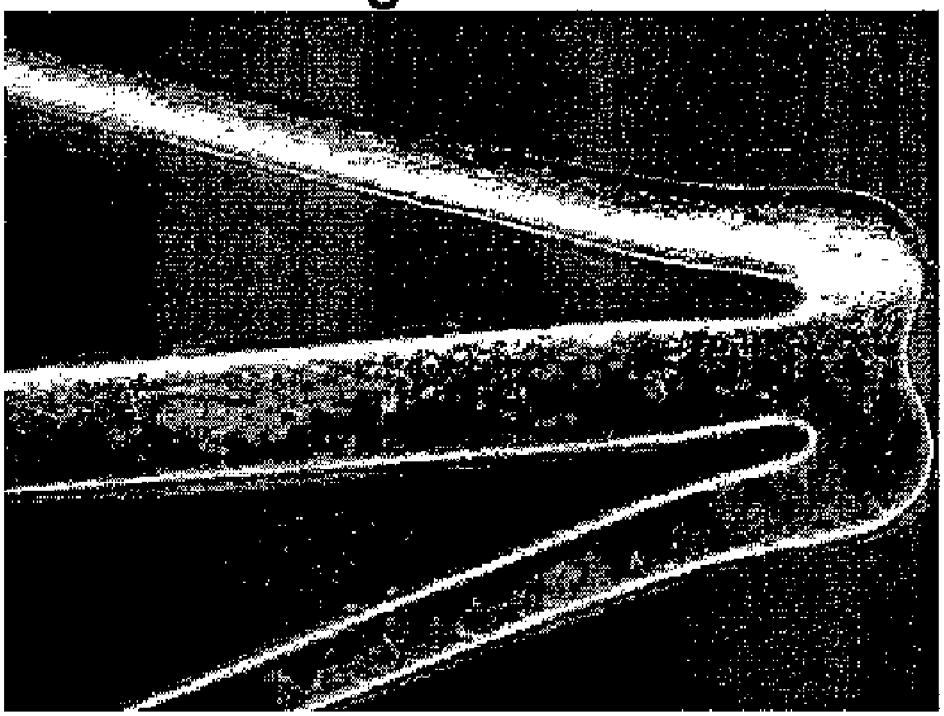

FIG. 12A shows a 50× optical micrograph of a metal stent coated with about 40% dihydrate paclitaxel (60% amorphous paclitaxel) coating prepared by ultrasonic spray coating a 4.68 mM paclitaxel solution in a 95% v methanol (5% water) solvent. FIG. 12B shows a 115× optical micrograph of the coating shown in FIG. 12A. The 40:60 w/w dPTX:aPTX coating has a clearer and less spotty appearance than the coating in FIGS. 10A-10B due to the increased proportion of the amorphous solid form of paclitaxel. Regions of varying opacity in the coating result from the mixture of the amorphous (clear) solid form of paclitaxel with the dihydrate (opaque, white) solid form.

Figure 13A:
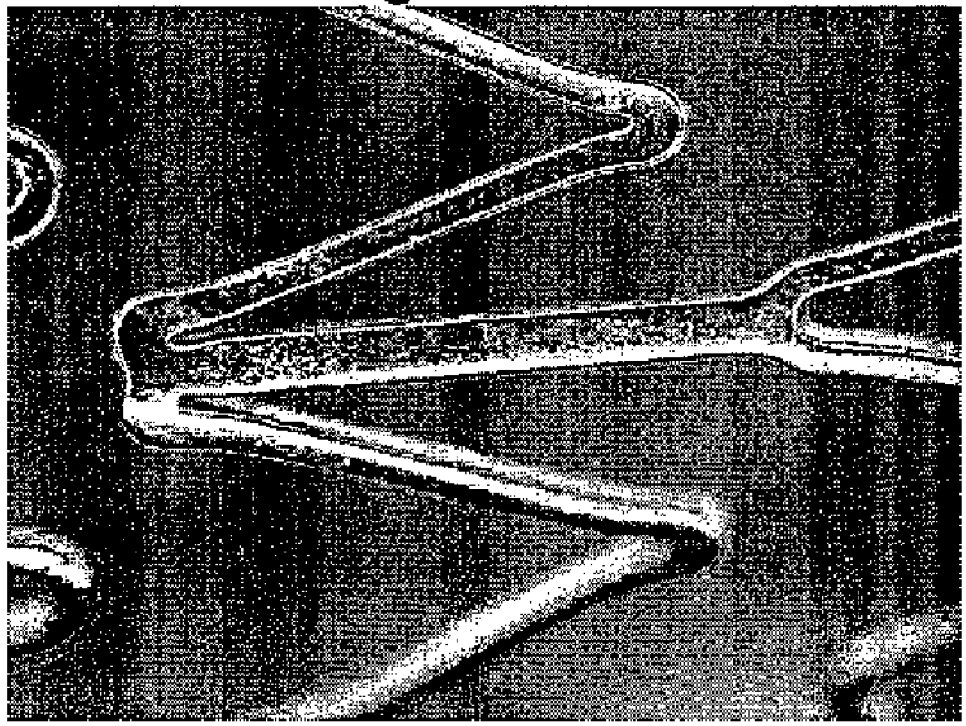
FIG. 13A and FIG. 13B are optical micrographs of a paclitaxel coated stent.
Figure 13B:
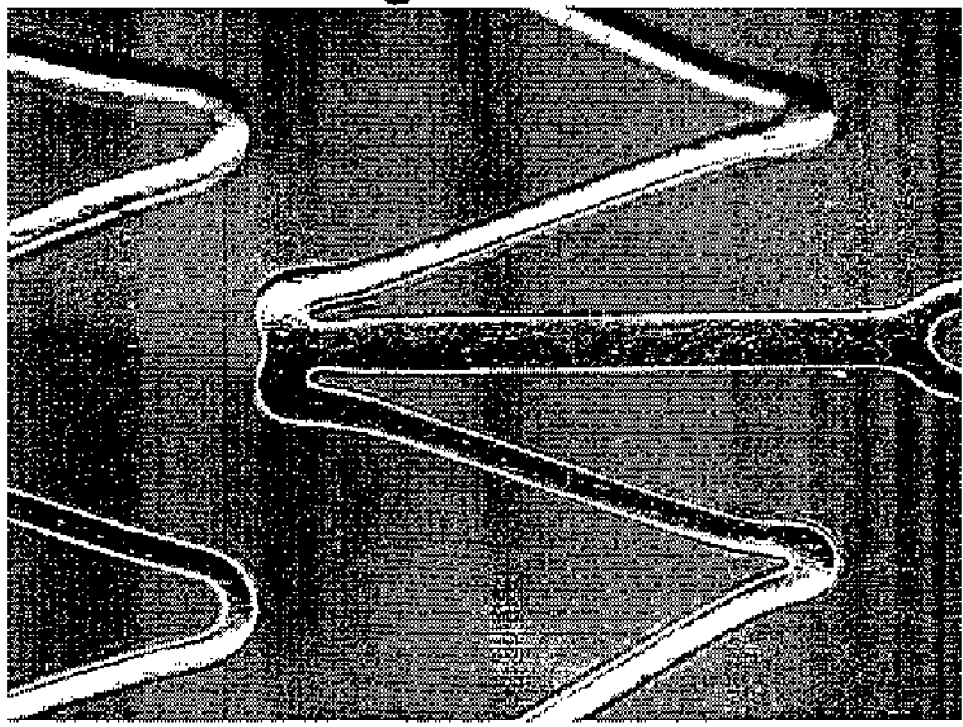

FIG. 13A shows a 50× optical micrograph of a metal stent coated with about 100% amorphous paclitaxel coating prepared by ultrasonic spray coating a 4.68 mM paclitaxel solution in a 95% v methanol (5% water) solvent. FIG. 13B shows a 115× optical micrograph of the coating shown in FIG. 13A. The aPTX coating has a clearer appearance indicative of the amorphous (clear) solid form of paclitaxel.

Notably, as the dose of paclitaxel in the coating increases, more amorphous solid form is typically needed to maintain a given level of durability. For example, a paclitaxel-only coating having a 50:50 ratio of the dihydrate:amorphous solid forms was durable at a dose of 3 micrograms/$mm^2$ but not for a dose of 1 micrograms/$mm^2$. That is, paclitaxel coatings with less than 50% dihydrate solid form were typically required to maintain durability at the 1 micrograms/$mm^2$ coating that was comparable to the 3 micrograms/$mm^2$ coating.

Table 6 below provides examples of preferred abluminal paclitaxel coatings on a 6×20 radially expandable vascular stent, showing the relationship between the composition of the spray solution and the resulting coating composition. Each coating is deposited using ultrasonic deposition according to Table 4 above at a temperature of about 87° F. The spray solution included the concentration of paclitaxel in Table 6 with methanol and water in a ratio that provides a desired amount of the dihydrate solid form. As described by Table 3a and Table 3b, increasing the amount of methanol relative to water resulted in less dihydrate in the coating at any concentration of paclitaxel.

TABLE 6

Preferred Paclitaxel Coatings

| Paclitaxel Dose (micrograms/mm²) | Total Paclitaxel (micrograms) | Preferred dPTX:aPTX for durability (%:%) | Concentration Paclitaxel in Spray Solution (mM) |
| --- | --- | --- | --- |
| 0.06 | 5 | 80:20 | 0.70 |
| 0.30 | 24 | 75:25 | 1.74 |
| 1.00 | 74 | 70:30 | 2.34 |
| 3.00 | 219 | 50:50 | 4.68 |

Medical Devices

The coatings may be applied to one or more surfaces of any implantable medical device having any suitable shape or configuration. The medical device may be adapted or selected for temporary or permanent placement in the body for the prophylaxis or treatment of a medical condition. The present invention is applicable to implantable or insertable medical devices of any shape or configuration. Typical subjects (also referred to herein as "patients") are vertebrate subjects (i.e., members of the subphylum cordata), including, mammals such as cattle, sheep, pigs, goats, horses, dogs, cats and humans.

Sites for placement of the medical devices include sites where local delivery of taxane therapeutic agents are desired. Common placement sites include the coronary and peripheral vasculature (collectively referred to herein as the vasculature). Other potential placement sites include the heart, esophagus, trachea, colon, gastrointestinal tract, biliary tract, urinary tract, bladder, prostate, brain and surgical sites, particularly for treatment proximate to tumors or cancer cells. Where the medical device is inserted into the vasculature, for example, the therapeutic agent is may be released to a blood vessel wall adjacent the device, and may also be released to downstream vascular tissue as well.

The medical device of the invention may be any device that is introduced temporarily or permanently into the body for the prophylaxis or therapy of a medical condition. For example, such medical devices may include, but are not limited to, stents, stent grafts, vascular grafts, catheters, guide wires, balloons, filters (e.g. vena cava filters), cerebral aneurysm filler coils, intraluminal paving systems, sutures, staples, anastomosis devices, vertebral disks, bone pins, suture anchors, hemostatic barriers, clamps, screws, plates, clips, slings, vascular implants, tissue adhesives and sealants, tissue scaffolds, myocardial plugs, pacemaker leads, valves (e.g. venous valves), abdominal aortic aneurysm (MA) grafts, embolic coils, various types of dressings, bone substitutes, intraluminal devices, vascular supports, or other known biocompatible devices.

In general, intraluminal stents for use in connection with the present invention typically comprise a plurality of apertures or open spaces between metallic filaments (including fibers and wires), segments or regions. Typical structures include: an open-mesh network comprising one or more knitted, woven or braided metallic filaments; an interconnected network of articulable segments; a coiled or helical structure comprising one or more metallic filaments; and, a patterned tubular metallic sheet (e.g., a laser cut tube). Examples of intraluminal stents include endovascular, biliary, tracheal, gastrointestinal, urethral, ureteral, esophageal and coronary vascular stents. The intraluminal stents of the present invention may be, for example, balloon-expandable or self-expandable. Thus, although certain embodiments of the present invention will be described herein with reference to vascular stents, the present invention is applicable to other medical devices, including other types of stents.

In one embodiment of the present invention, the medical device comprises an intraluminal stent. The stent may be self-expanding or balloon-expandable and may be a bifurcated stent, a coronary vascular stent, a urethral stent, a ureteral stent, a biliary stent, a tracheal stent, a gastrointestinal stent, or an esophageal stent, for example. More specifically, the stent may be, for example, a Wallstent, Palmaz-Shatz, Wiktor, Strecker, Cordis, AVE Micro Stent, Igaki-Tamai, Millenium Stent (Sahajanand Medical Technologies), Steeplechaser stent (Johnson & Johnson), Cypher (Johnson & Johnson), Sonic (Johnson & Johnson), BX Velocity (Johnson & Johnson), Flexmaster (JOMED) JoStent (JOMED), S7 Driver (Medtronic), R-Stent (Orbus), Tecnic stent (Sorin Biomedica), BiodivYsio (Abbott), Trimaxx (Abbott), DuraFlex (Avantec Vascular), NIR stent (Boston Scientific), Express 2 stent (Boston Scientific), Liberte stent (Boston Scientific), Achieve (Cook/Guidant), S-Stent (Guidant), Vision (Guidant), Multi-Link Tetra (Guidant), Multi-Link Penta (Guidant), or Multi-Link Vision (Guidant). Some exemplary stents are also disclosed in U.S. Pat. Nos. 5,292,331 to Boneau, 6,090,127 to Globerman, 5,133,732 to Wiktor, 4,739,762 to Palmaz, and 5,421,955 to Lau. Desirably, the stent is a vascular stent such as the commercially available Gianturco-Roubin FLEX-STENT®, GRII™, SUPRA-G, ZILVER or V FLEX coronary stents from Cook Incorporated (Bloomington, Ind.).

For restenosis treatment, it is desirable that the release be initiated before or at the time at which cell proliferation occurs, which generally begins approximately three days after the injury to the artery wall by the PTCA procedure. Of course, the release profile will be tailored to the condition that is being treated. For example, where an anti-inflammatory or anti-thrombotic effect is desired, release is typically initiated sooner. Moreover, in instances where DNA is used that has an expression half-life that is shorter than the time period desired for administration of the therapy, release of the DNA from the device is typically regulated such that it occurs over a time period longer than the half-life of the DNA expression, thus allowing new copies of DNA to be introduced over time and thereby extending the time of gene expression.

The stent or other medical device of the invention may be made of one or more suitable biocompatible materials such as stainless steel, nitinol, MP35N, gold, tantalum, platinum or platinum iridium, niobium, tungsten, inconel, ceramic, nickel, titanium, stainless steel/titanium composite, cobalt, chromium, cobalt/chromium alloys, magnesium, aluminum, or other biocompatible metals and/or composites or alloys such as carbon or carbon fiber. Other materials for medical devices, such as drainage stents or shunts, include cellulose acetate, cellulose nitrate, silicone, cross-linked polyvinyl alcohol (PVA) hydrogel, cross-linked PVA hydrogel foam, polyurethane, polyamide, styrene isobutylene-styrene block copolymer (Kraton), polyethylene terephthalate, polyurethane, polyamide, polyester, polyorthoester, polyanhydride, polyether sulfone, polycarbonate, polypropylene, high molecular weight polyethylene, polytetrafluoroethylene, or other biocompatible polymeric material, or mixture of copolymers thereof; polyesters such as, polylactic acid, polyglycolic acid or copolymers thereof, a polyanhydride, polycaprolactone, polyhydroxybutyrate valerate or other biodegradable polymer, or mixtures or copolymers thereof; extracellular matrix components, proteins, collagen, fibrin or other therapeutic agent, or mixtures thereof. Desirably, the device is made of stainless steel, cobalt-chromium or a nickel-titanium alloy (e.g., Nitinol).

The stent may be deployed according to conventional methodology, such as by an inflatable balloon catheter, by a self-deployment mechanism (after release from a catheter), or by other appropriate means. The stent may be formed through various methods, such as welding, laser cutting, or molding, or it may consist of filaments or fibers that are wound or braided together to form a continuous structure. The stent may also be a grafted stent in which the therapeutic agent is incorporated into the graft material.

Medical Device Packages

Figure 16:
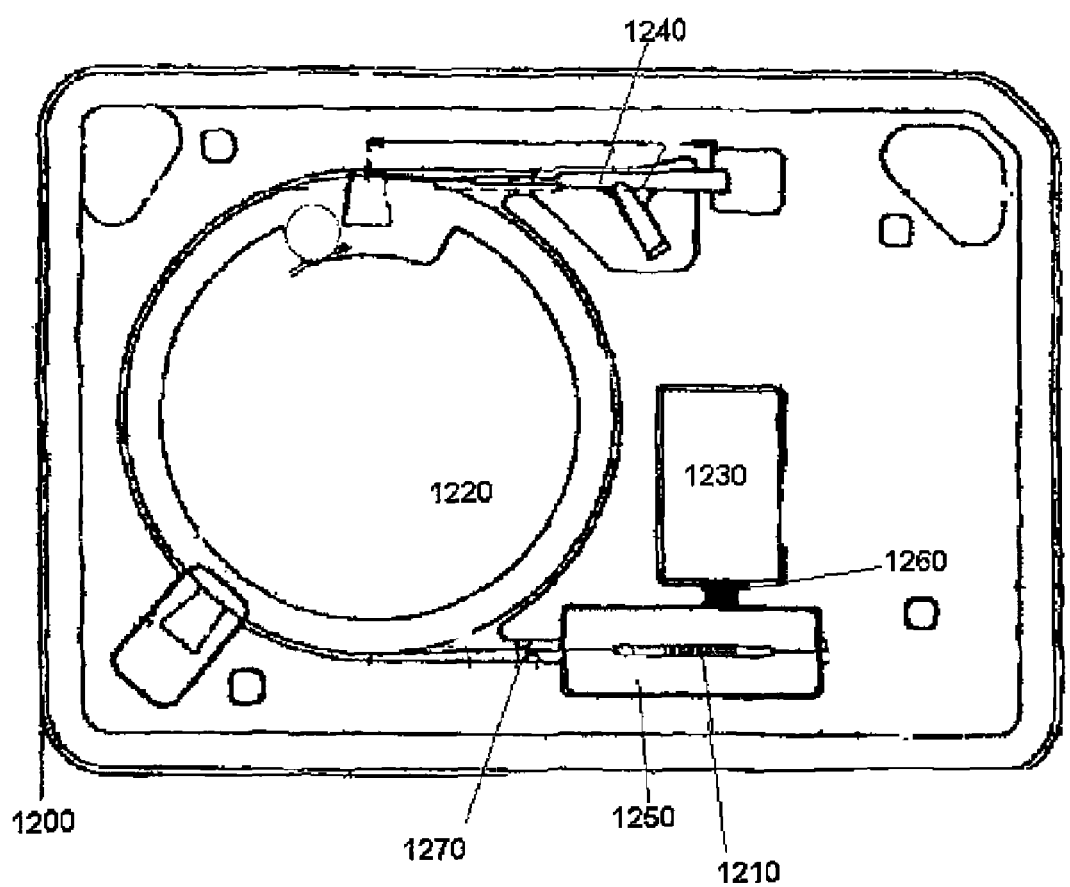
FIG. 16 is a package configuration suitable for packaging a taxane-coated medical device.

Another embodiment provides medical device packages and methods of packaging a medical device coated with a taxane therapeutic agent. The packaging for a treated stent delivery system may be configured as any suitable configuration, such as the tray 1200 shown in FIG. 16, a pouch or other structure. The tray 1200 is provided with a non-coated medical device storage portion 1220, a coated medical device storage portion 1250 and a conditioning compartment 1230.

The tray 1200 may be fabricated of clear material to allow for viewing. Alternatively, the tray 1200 may be fabricated of opaque material to aid in preventing degradation of the coating on a medical device from light. The tray 1200 may be made, for example, of a high barrier plastic, or other suitable materials. Tray 1200 may be thermoformed, for example, from polyethylene, or another suitable material. The tray 1200 may further comprise one or more voids which may be used to hold other materials and accessories. For example, a coated stent may be more sensitive to moisture. One or more of voids may therefore be used to hold desiccant packets or oxygen absorber packets. Voids may also hold any suitable chemicals that may be used to prolong shelf-life or prevent decay of coating on a stent. Additional accessories may also be stored within one or more of voids including, but not limited to, additional catheters, additional guidewires, additional introducer assemblies, flushing cannulas and additional stylets.

The tray 1200 may also include a lid fabricated of clear material to allow for viewing or an opaque material to aid in preventing degradation of the coating on a medical device from light. The lid may be made, for example, of a high barrier plastic, or other suitable materials. In some embodiments of the invention, tray 1200 and lid may be made of different materials. For example, tray 1200 may be made of a high barrier plastic and lid may be a foil cover over tray or a foil pouch into which tray may be sealed. The lid may be made of foil, for example, in order to prevent moisture and oxygen from affecting components packaged in tray 1200. Alternatively, the lid may be made from the same material as tray 1200. For example, lid and tray 1200 may be formed of the same thermoformed plastic, such as polyethylene. The lid may include one or more access ports to the conditioning compartment 1230 to permit passage of fluid, such as humidity, therethrough. The lid may also be adapted to permit removal of a barrier 1260 separating the coated medical device storage portion 1250 from the conditioning compartment 1230.

The coated medical device storage portion 1250 is sealed in a material effective to maintain the enclosed volume at desired level of humidity and/or temperature so as to prevent undesired changes in the medical device coating. For example, the coated medical device storage portion 1250 may be a sealed volume formed from an oxygen and moisture barrier material. A coated portion of a medical device may be secured within the coated medical device storage portion 1250. In the tray 1200, the coated medical device storage portion 1250 may enclose a paclitaxel coated stent crimped on the distal end of a delivery catheter. The delivery catheter may optionally include an expandable balloon portion formed from a material such as polyethylene, polyethylene terephthalate (PET), or from nylon or the like. The length and diameter of the balloon may be selected to accommodate the particular configuration of a stent crimped around the balloon. The balloon may be carried on any catheter, such as, for example PTCA low profile catheters and over the wire catheters. Alternatively, a coated stent may be self-expanding and the delivery catheter may include an outer sheath concentrically disposed around the crimped stent, rather having a balloon portion.

The proximal portion of the delivery catheter may be coiled within the non-coated medical device portion 1220, with the proximal end 1240 of the delivery catheter secured within a molded portion of the plastic housing of the tray 1200. The tray 1200 may be adapted to form a water or air tight seal 1270 around the catheter between the coated medical device portion 1250 of the tray 1200 and the non-coated medical device portion 1220. The coated medical device may be a paclitaxel coated stent having a high level of amorphous paclitaxel (e.g., at least 90% amorphous paclitaxel) to impart a high level of durability to the coating.

The tray 1200 is preferably adapted to permit conditioning of the coated medical device portion within the coated medical device portion 1250 of the tray 1200. The conditioning compartment 1230 may contain a fluid or other means of admitting humidity and/or heat into the coated medical device portion 1250 by breaking or removing a barrier 1260 between the two portions of the tray 1200. The barrier 1260 may be any suitable structure adapted to permit fluid communication between the coated medical device portion 1250 and the conditioning compartment 1230 upon alteration of the barrier 1260. For example, the barrier 1260 may be a strip or tab that can be removed, a material that can be melted or dissolved by heating or adding a fluid to the conditioning compartment 1230 and/or the coated medical device portion 1250. The conditioning compartment 1230 may contain a liquid, such as water, that can be evaporated within the conditioning compartment 1230. For example, the tray 1200 may be formed of plastic materials that can be exposed to microwave radiation to heat the fluid in the tray 1230 and permit steam to pass across the barrier 1260 into the coated medical device portion 1250. In one aspect, the tray 1200 is heated to evaporate fluid in the conditioning compartment 1230 and permit the evaporated fluid to contact the coated medical device 1210 within the coated medical device portion 1250 for a period sufficient to decrease the solubility of a taxane therapeutic agent in the coated medical device 1210, prior to removing the medical device from the tray 1200.

The conditioning compartment 1230 may also be configured to permit humidity to enter the tray 1200 from outside, for example by removing a barrier film or tab to expose the conditioning compartment 1230 to humidity or heat outside the tray 1200. In another aspect, the conditioning compartment 1230 is maintained at a vacuum prior to conditioning and conditioning of the coated medical device 1210 may be initiated by removing a sealing film defining a portion of the conditioning compartment 1230 to expose the conditioning compartment to humidity outside the tray 1200.

Instead of the tray 1200, the package and compartments (1250, 1230 and 1220) may also be formed as portions of a single pouch. The non-coated medical device storage portion 1220 may be formed of a sheet of impermeable membrane such as Tyvek® material laminated to a layer of foil. Tyvek® material is commercially available from DuPont and consists of multiple spun woven extruded polyethylene strands, compressed under high pressure to form a complex system of microscopic porous channels which provides a tortuous porous path within a thin flexible opaque sheet. Other breathable membranes, such as paper, that suitably provide a barrier to microbes but allow the passage of air and other gases and moisture could also be used. The compartment 1250 is preferably lined with an oxygen and moisture barrier (eg, EVOH or PVDC) film.

Optionally, the coated medical device storage portion 1250 may contain oxygen and moisture absorber packs. Suitable oxygen and moisture absorber packs are commercially available from Mitsubishi Gas chemical company, Inc./(Pharmakeep KD-20.TM.), and Silgel Ltd./(4 g Molecular Sieve sachets), respectively.

Methods of Treatment

Methods of treatment preferably include the step of inserting into a patient a coated medical device having any of the compositions and/or configurations described above. For example, when the medical device is a stent coated by the coating methods described above, the method of treatment involves implanting the stent into the vascular system of a patient and allowing the therapeutic agent(s) to be released from the stent in a controlled manner, as shown by the drug elution profile of the coated stent.

In one preferred embodiment, the conditioned and coated medical devices are implanted to treat peripheral vascular disease, for example by implanting the coated medical device in a peripheral artery. In one aspect, methods of treating peripheral vascular disease (PVD) are provided. PVD is a disease of the lower extremities that may present various clinical indications ranging from asymptomatic patients, to patients with chronic critical limb ischemia (CLI) that might result in amputation and limb loss.

Methods of treating peripheral vascular disease, including critical limb ischemia, preferably comprise the endovascular implantation of one or more conditioned and coated medical devices provided herein. Atherosclerosis underlies many cases of peripheral vascular disease, as narrowed vessels that cannot supply sufficient blood flow to exercising leg muscles may cause claudication, which is brought on by exercise and relieved by rest. As vessel narrowing increases, critical limb ischemia (CLI) can develop when the blood flow does not meet the metabolic demands of tissue at rest. While critical limb ischemia may be due to an acute condition such as an embolus or thrombosis, most cases are the progressive result of a chronic condition, most commonly atherosclerosis. The development of chronic critical limb ischemia usually requires multiple sites of arterial obstruction that severely reduce blood flow to the tissues. Critical tissue ischemia can be manifested clinically as rest pain, nonhealing wounds (because of the increased metabolic requirements of wound healing) or tissue necrosis (gangrene).

The coated medical device can be implanted in any suitable body vessel. Typical subjects (also referred to herein as "patients") are vertebrate subjects (i.e., members of the subphylum cordata), including, mammals such as cattle, sheep, pigs, goats, horses, dogs, cats and humans. Sites for placement of the medical devices include sites where local delivery of taxane therapeutic agents are desired. Common placement sites include the coronary and peripheral vasculature (collectively referred to herein as the vasculature). Other potential placement sites include the heart, esophagus, trachea, colon, gastrointestinal tract, biliary tract, urinary tract, bladder, prostate, brain and surgical sites, particularly for treatment proximate to tumors or cancer cells. Where the medical device is inserted into the vasculature, for example, the therapeutic agent is may be released to a blood vessel wall adjacent the device, and may also be released to downstream vascular tissue as well.

The configuration of the implantable frame can be selected based on the desired site of implantation. For example, for implantation in the superficial artery, popliteal artery or tibial artery, frame designs with increased resistance to crush may be desired. For implantation in the renal or iliac arteries, frame designs with suitable levels of radial force and flexibility may be desired. Preferably, a coated vascular stent is implanted in a non-coronary peripheral artery, such as the iliac or renal arteries.

In one embodiment, a medical device comprising a balloon-expandable frame portion coated with a taxane therapeutic agent can be endoluminally delivered to a point of treatment within an infrapopliteal artery, such as the tibial or peroneal artery or in the iliac artery, to treat CLI. For treating disease conditions, coated balloon-expandable medical devices can comprise an expandable frame attached to a coating. The frame can be also be formed from a bioabsorbable material, or comprise a coating of the therapeutic agent material over at least a portion of the frame. The frame can be configured to include a barb or other means of securing the medical device to the wall of a body vessel upon implantation.

In another aspect, a coated medical device can be a self-expanding device such as a coated NITINOL stent coated with the taxane therapeutic agent, and configured to provide a desirable amount of outward radial force to secure the medical device within the body vessel. The medical device can be preferably implanted within the tibial arteries for treatment of CLI. For instance, the coated medical device can be configured as a vascular stent having a self-expanding support frame formed from a superelastic self-expanding nickel-titanium alloy coated with a metallic bioabsorbable material and attached to a graft material. A self-expanding frame can be used when the body vessel to be stented extends into the distal popliteal segment. The selection of the type of implantable frame can also be informed by the possibility of external compression of an implant site within a body vessel during flexion of the leg.

In one aspect, methods of delivering a therapeutic agent to a blood vessel are provided. The methods may include the step of providing a coated vascular stent comprising a radially-expandable vascular stent having an abluminal side and a luminal side defining a substantially cylindrical lumen and being movable from a radially expanded configuration to a radially compressed configuration; and a coating on at least one surface of the vascular stent. The coating may include a taxane therapeutic agent such as paclitaxel in one or more solid forms. Preferably, the coating includes paclitaxel in the dihydrate solid form. The method may also include the steps of: intralumenally inserting the coated vascular stent into the blood vascular system using a means for intralumenal delivery comprising a catheter, positioning the coated vascular stent within a peripheral artery; and radially expanding the coated vascular stent within the peripheral artery so as to place the coated vascular stent in contact with a portion of a wall of the peripheral artery in a manner effective to deliver the therapeutic agent to the wall of the blood vessel.

A consensus document has been assembled by clinical, academic, and industrial investigators engaged in preclinical interventional device evaluation to set forth standards for evaluating drug-eluting stents such as those contemplated by the present invention. See "Drug-Eluting Stents in Preclinical Studies—Recommended Evaluation From a Consensus Group" by Schwartz and Edelman (available at "http://www.circulationaha.org." (incorporated herein by reference).

EXAMPLES

In the following examples, the equipment and reagents specified below were used:

TABLE 7

Reagents and Equipment

| Equipment Name | Manufacturer | Manufacturer ID | Vendor |
|---|---|---|---|
| 1 µg Balance | Mettler | AX 26 | VWR |
| 10 µg Balance | Mettler | AX 105 DR | VWR |
| Top Loading Balance | Ohaus | GT 4100 | VWR (not avail.) |
| Inline Spectrometer | Agilent | 8453 | Agilent |
| Chemstation | Agilent | Version A.10.01 | Agilent |
| Coating Spectrometer 1 | Perkin Elmer | Lambda 14 P | Perkin Elmer |
| Coating Spectrometer 2 | Perkin Elmer | Lambda 45 | Perkin Elmer |
| UV Winlab | Perkin Elmer | Version 5.1 | Perkin Elmer |
| Cuvettes | Perkin Elmer | B0631077 | VWR |
| Electrostatic Coater | Terronics | Custom | Terronics |
| MED Spray Gun/Badger | Badger | Model 200 | Ding-A-Ling |
| Cook Incorporated Spray Gun | EFD | 780S-SS | EFD |
| Cook Incorporated Spray Controller | EFD | Valvemate 7040 | EFD |
| Microscope | Leica | MZ-16 | Nuhsbaum Inc. |
| Image Pro Plus | MediaCybernetics | Version 5.1 | Media Cybernetics |
| Microsoft Office | Microsoft | Version 2003 | New Egg |
| Stopwatch | Private Label | n/a | VWR |
| Glassware | Kimball | Various | VWR |
| Ethanol | Aaper | E 200 PP | Aaper |
| Methanol | Sigma | M 3641 | Sigma |
| Dichloromethane | Sigma | 15,479-2 | Sigma |
| Water | Ricca Chemical | 9150-5 | VWR |

Example 1

Preparation of Amorphous, Anhydrous and Dihydrate Paclitaxel

Bulk samples of amorphous, anhydrous and dihydrate paclitaxel solid forms were prepared by the methods described below. These preparations were reproduced based on Jeong Hoon Lee et al., "Preparation and Characterization of Solvent Induced Dihydrate, Anhydrous and Amorphous Paclitaxel," *Bull. Korean Chem. Soc.* v. 22, no. 8, pp. 925-928 (2001).

Samples of bulk amorphous paclitaxel were prepared as follows: 1.01 g of paclitaxel (Phytogen Life Sciences) was dissolved in 5 mL dichloromethane (Mallinckrodt) while agitating to form a paclitaxel solution; the paclitaxel solution was left open to air at about 23° C. for about 10 hours to permit evaporation of the dichloromethane and formation of amorphous paclitaxel. The melting temperature of the amorphous paclitaxel was 209-215° C.

Samples of bulk anhydrous paclitaxel were prepared as follows: 1.06 g of paclitaxel (Phytogen Life Sciences) were dissolved in 40 mL methanol (Sigma Aldrich, 99.93% HPLC Grade) while sonnicating the container and inversion of the container to form a paclitaxel solution; about 2 mL of hexane (Sigma Aldrich) was added to the paclitaxel solution, and the solution was placed in a freezer at about −20° C. overnight (approximately 10 hours) to form anhydrous crystalline paclitaxel. The melting temperature of the anhydrous paclitaxel was 190-210° C.

Samples of dihydrate paclitaxel were prepared as follows: 1.09 g paclitaxel (Phytogen Life Sciences) were dissolved in 25 mL methanol while sonnicating the container to form a paclitaxel solution; about 5 mL of water was added to the paclitaxel solution; and the sample was placed in a freezer at about −20° C. overnight to form dihydrate crystals. The melting temperature of the dihydrate crystal was 209-215° C. Subsequently, the sample was sealed under vacuum to 0.025 torr for 2.5 hours to remove residual solvent. Dihydrate paclitaxel samples were also prepared as follows: 50.08 g paclitaxel (Phytogen Life Sciences) was dissolved in 1.1 L methanol to form a solution; 275 mL water was subsequently added to the methanol solution in a drop-wise fashion to form a precipitate that was refrigerated at about −20° C. overnight (about 10 hours); the resulting solid precipitate was filtered, dissolved in 1500 mL methanol and 375 mL water and was subsequently added in a drop-wise fashion; the resulting crystals were recrystallized a third time using 1200 mL methanol with 300 mL water; and the resulting dihydrate crystals were collected.

Example 2

Ultraviolet (UV) Spectra of Bulk Paclitaxel Samples

The three solid samples prepared in Example 1 (amorphous, dihydrate and anhydrous paclitaxel) were dissolved in ethanol to form spray sample solutions. The ultraviolet spectra of each of the three samples were taken (Agilent In-Line UV Spectrophotometer), to obtain three spectra that were indistinguishable from the spectrum 100 shown in FIG. 2. The spectra all included a peak at 227 nm indicative of the taxane core structure in the paclitaxel, indicating that the paclitaxel solid forms of Example 1 were not distinguishable from each other based on UV spectra of the paclitaxel in solution.

Example 3

Infrared Spectra of Bulk Paclitaxel Samples

FTIR Infrared spectra each of the samples prepared in Example 1 were obtained following procedure: a pellet of KBr was made by grinding the paclitaxel crystal with KBr using a mortar and pestle at room temperature (about 23° C.); the resulting solid was placed under vacuum to remove residual methanol solvent (0.025 mmHg); and a spectra was recorded of the paclitaxel analyte. Representative spectra of each solid form of paclitaxel are provided in FIGS. 3A-3C, as discussed above. Infrared spectra may also be obtained using Attenuated Total Reflection Infrared (ATR-IR) from a coating or a small sample of a solid taxane sample from a coating. One suitable ATR-IR apparatus is the PerkinElmer Horizontal ATR model L1200361.

Example 4

Ultrasonic Spray Coating of Stents with Paclitaxel

Stents with coatings consisting of paclitaxel taxane therapeutic agent coatings including both the dihydrate solid form and in the amorphous solid forms of paclitaxel were prepared by spray coating a solution comprising paclitaxel, methanol and water. A paclitaxel solution in methanol and water was prepared. Specifically, a 1.74 mM paclitaxel solution was prepared in 68% methanol by dissolving 7.43 mg of paclitaxel in 5 mL of previously made solution of 68% methanol 32% water. The solution was sprayed from an ultrasonic spray gun (Sono-tek Model 06-04372) in a glove box. Before spraying, the glove box was purged with nitrogen at 20 psi for 15 minutes. The atmosphere in the glove box was adjusted until the oxygen meter reads a constant 200 ppm within the glove box. The heat in the glovebox was set to 31° C. (88° F.), the air shroud to 2.0 psi and the ultrasonic power to 1.0 W. The paclitaxel solution was loaded into a syringe and place on the syringe pump in the ultrasonic coating apparatus and a bare metal stent (6×20 ZILVER, Cook Inc., Bloomington, Ind.) was mounted on a mandrel aligned with the spray nozzle. The solution was sprayed onto a stent using a 60 kHz nozzle at a flow rate of 0.03 mL/min, a coating velocity of 0.025 in/sec, a nozzle power of 1.0 W, a process gas pressure of 2.0 psi, and a distance from the nozzle to the stent of about 12 mm, while rotating the stent with an axial rotation rate of 60 rpm. Only the abluminal surface of the stent was coated.

Example 5A

Post-Deposition Conditioning of Paclitaxel-Coated Stents

Paclitaxel-coated stents may be prepared by spraying the abluminal surface of a medical device with a solution of paclitaxel in a suitably volatile solvent, such as ethanol. The coating preferably contains enough paclitaxel in the amorphous (clear) solid state to provide a suitable level of durability. The coating may be conditioned by, in this example, raising the temperature to between about 35° C. and 50° C. (or higher) and a relative humidity level of about 75%-100% for a period of at least about 5 hours, and preferably about 12-15 hours or longer.

In this example, a substantially visually clear paclitaxel coating was applied to the abluminal surface of a 6×20 mm ZILVER stent (Cook Incorporated, Bloomington, Ind.) by spraying a solution consisting of paclitaxel dissolved in ethanol onto the abluminal surface of the stent. The spray gun was passed over the stent for multiple passes until a desired dose of paclitaxel is coated on the abluminal surface of the stent. For example, the paclitaxel coatings may be spray deposited until the coatings contain a dose of about up to about 4 µg of the taxane therapeutic agent per mm$^2$ of the abluminal surface area of the stent, depending on the number of applications by the spray gun. The spray coating conditions were selected to evaporate the ethanol solvent during the spraying process, or in combination with a step of drying the sprayed stents. The resulting coating consisted of the paclitaxel on the abluminal side of the stent one or more solid forms, including the amorphous solid form.

The solid form(s) of paclitaxel present in the coating may be identified by visual inspection and solubility of the coating in an elution medium described herein. Elution medium such as an aqueous solution of cyclodextrin may be contacted with the paclitaxel coating, and the concentration of paclitaxel in the elution medium can be monitored as a function of time using UV spectrophotometry as described above. A clear paclitaxel coating is indicative of an amorphous solid form, while a white or cloudy coating is indicative of a solvated (e.g., dehydrate) solid form of paclitaxel. The dihydrate solid form is more soluble in an aqueous cyclodextrin elution medium than the amorphous solid form. Accordingly, a paclitaxel coating having a higher percentage of the dihydrate solid form typically has a slower rate of elution from the coating than a coating with a higher percentage of the amorphous solid form.

By coating multiple stents using comparable or identical coating methods, the composition of the coatings may be estimated by eluting one of the coatings in a suitable elution medium as an estimate of the coating composition of other stents coated using comparable or identical coating methods. One representative coated stent can be tested to determine the paclitaxel solid forms present in the other coatings. The presence of both dihydrate and amorphous solid forms may be identified by the difference in solubility properties of the two solid forms: contacting the coating with a porcine serum elution medium can elute the amorphous solid form, while subsequent contact with sodium dodecyl sulfate can elute the remaining paclitaxel. The elution rate can be monitored by UV-detection of the elution medium after contact with the paclitaxel coating. Another representative coated stent can be weighed before and after crimping, and the percentage of coating weight loss can be measured. Typical coating weight loss during crimping is about 6%.

The coated stent was crimped onto the distal portion of a delivery catheter and then conditioned by maintaining the paclitaxel coated stent at a temperature to about 120° F. (48° C.) at a relative humidity to about 100% for a period of about 13 hours. After the conditioning process, areas of the paclitaxel coating that were substantially clear (transparent) became white and clouded, indicated formation of dihydrate paclitaxel. Subsequent elution tests of the coating indicated an increase in the amount of dihydrate paclitaxel in the coating relative to other comparable paclitaxel stent coatings that were not conditioned.

After conditioning, a coated stent can be tested by dissolution in any suitable elution medium, such as aqueous HCD solution followed by sodium dodecyl sulfate or ethanol to identify the solid forms present in the conditioned coating. The weight percentage of the dihydrate paclitaxel solid form is higher in the conditioned coating than in the coating before conditioning. The dihydrate paclitaxel is preferably up to about 75% of the coating weight. Another conditioned stent can be weighed before and after crimping, and the percentage of coating weight loss measured. Typical values for coating weight loss of a conditioned stent are expected to be less than 6%, for example about 3-5%.

Example 5B

Post-Deposition Conditioning of Paclitaxel-Coated Stents

In this example, the abluminal surface of six ZILVER stents (Cook Incorporated, Bloomington, Ind.) of various sizes were coated with paclitaxel by spraying a solution consisting of paclitaxel dissolved in dichloromethane onto the abluminal surface of the stent. The spray gun was passed over the stent for multiple passes until a desired dose of paclitaxel is coated on the abluminal surface of the stent. The paclitaxel coatings were spray deposited until the coatings contained therapeutically effective dose about up to about 5 µg of paclitaxel per mm² of the abluminal surface area of the stent, depending on the number of applications by the spray gun. The spray coating conditions were selected to evaporate the dichloromethane solvent during the spraying process, or in combination with a step of drying the sprayed stents. The spray coating solution and resulting dose of paclitaxel deposited on each stent are summarized in Table 8A below. A total of 120 mL of each spray solution was applied with a spray gun in a series of separate 10 mL spray applications to each stent, while rotating the stent 90-degrees with respect to the spray gun after each spray application. The resulting coating consisted of the paclitaxel on the abluminal side of the stent one or more solid forms, including the amorphous solid form. Each of the coatings was substantially transparent (clear) after deposition and before conditioning.

Each coated stent was conditioned by suspending each stent in a sealed chamber above heated circulating water maintained at 52° C. for 12 hours, providing a relative humidity of about 100%. The conditioned coated stents were removed from the chamber and visually inspected. Each coating changed appearance during the conditioning process. The conditioned coatings had increased portions of cloudy, white and largely opaque regions within portions of the coating that were substantially clear or transparent prior to the conditioning process. This change in visual appearance is believed to be indicative of increased presence of the cloudy, opaque dihydrate paclitaxel solid form compared to the substantially transparent amorphous paclitaxel solid form.

In this example, a coating consisting of paclitaxel was applied to a series of vascular stents, and the coatings were conditioned at temperature and humidity levels that are adequate to convert at least 5% of the coating from the amorphous paclitaxel solid form to the dihydrate paclitaxel solid form when the conditioning process is maintained for an effective period of time, such as in Example 5A. However, the short-duration conditioning processes for periods of up to 3 hours did not result in the expected changes to the coating.

The abluminal side of seven 6×20 mm ZILVER stents (Cook Incorporated, Bloomington, Ind.) were coated ultrasonically with a solution of 4.68 mM paclitaxel in ethanol and designated stents 1-7. The composition of Stent 1 was determined by first contacting the coating in a 1% aqueous HCD cyclodextrin solution to dissolve the amorphous solid form paclitaxel, followed by contacting the remaining coating with ethanol to dissolve the remaining paclitaxel, which was attributed to dihydrate paclitaxel. Coated stents 2-4 were subsequently exposed to humidity at room temperature by suspending the coated stents in a sealed chamber connected to a humidifier, providing an environment of about 100% RH for different periods of time. Stent 2 was maintained in this environment for 1 hour; stent 3 was maintained for 2 hours and stent 3 was maintained for 3 hours. All of the stents were rotated on the mandrel while being maintained in the 100% humidity. The stents were then Photographs of the stents before and after humidity are shown below. Coated stents 5-7 were subsequently exposed to humidity at a temperature of 85° F. (29.5° C.) by suspending the coated stents in a sealed chamber connected to a humidifier, providing an environment of about 100% RH for different periods of time. Stent 5 was

TABLE 8A

Spray Coating and Conditioning Parameters (Example 5B)

| Stent No. (Example Number) | mM Paclitaxel in Dichloromethane used as Spray Solution | Dose of Paclitaxel (micrograms/mm²) | Conditioning Temperature (° C.) | Conditioning Humidity | Conditioning Time (hrs) | Change in Appearance After Conditioning |
|---|---|---|---|---|---|---|
| 1 | 2.34 | 4.9 | 52 | 100% | 12 | All Coatings |
| 2 | 1.96 | 1.8 | 52 | 100% | 12 | Change from |
| 3 | 1.96 | 2.1 | 52 | 100% | 12 | Substantially |
| 4 | 1.96 | 3.0 | 52 | 100% | 12 | Clear to |
| 5 | 1.96 | 3.0 | 52 | 100% | 12 | Substantially |
| 6 | 1.96 | 3.0 | 52 | 100% | 12 | White/Cloudy |

Comparative Example 5C

Short-Duration Conditioning of Paclitaxel-Coated Stents

The conditioning process is preferably performed for a time period sufficient to increase the durability of the stents or decrease the solubility of the paclitaxel coating. For example, the conditioning process may be performed by maintaining a taxane therapeutic agent coating at a relative humidity of about 90% or higher and a temperature of about 85-95° F. (29.5-35° C.) for a period of time effective to effect one or more of the desired changes in the coating. The effective period of time is preferably at least 4 hours.

maintained in this environment for 1 hour; stent 6 was maintained for 2 hours and stent 7 was maintained for 3 hours. All of the stents were rotated on the mandrel while being maintained in the 100% humidity. The visual appearance of the stents was noted prior to elution to determine the solubility of the coating. The composition of Stents 2-7 was individually determined by first contacting each coating with a 1% aqueous HCD cyclodextrin solution to dissolve the amorphous solid form paclitaxel, followed by contacting the remaining coating with ethanol to dissolve the remaining paclitaxel, which was attributed to dihydrate paclitaxel. The difference in solubility of each coating was correlated to the solid form composition of the coating. Results are summarized in Table 8 below.

TABLE 8B

Comparative Conditioning Parameters (Example 5C)

| Stent No. (Example Number) | % Coating Amorphous/ Dihydrate Paclitaxel Solid Form pre-conditioning | Approximate Conditioning Temperature (° C.) | Conditioning Humidity | Conditioning Time | Change in Appearance After Conditioning | % Coating Amorphous Paclitaxel Solid Form post-conditioning |
|---|---|---|---|---|---|---|
| 1 | 93%/7% | 25 | <10% | 0 | None | 92%/8% |
| 2 | 99%/1% | 25 | 100 | 1 | Slightly cloudy | 98%/2% |
| 3 | 99%/1% | 25 | 100 | 2 | Slightly cloudy | 98%/2% |
| 4 | 99%/1% | 25 | 100 | 3 | Slightly cloudy | 98%/2% |
| 5 | 99%/1% | 30 | 100 | 1 | Areas of white spots appear | 93%/7% |
| 6 | 99%/1% | 30 | 100 | 2 | Slightly cloudy | 98%/2% |
| 7 | 99%/1% | 30 | 100 | 3 | Slightly cloudy | 98%/2% |

Example 6

Elution of Paclitaxel-Coated Stents in Porcine Serum

Stents with coatings consisting of paclitaxel taxane therapeutic agents in both the dihydrate solid form and in the amorphous form were prepared by spray coating a solution comprising various amounts of paclitaxel, methanol and water. A 2.34 mM paclitaxel solution in 88% methanol and 12% water (v) was made with a total volume of about 10 mL (20.04 mg paclitaxel). Twelve (12) 6×20 ZILVER (Cook Inc., Bloomington, Ind.) stents were spray coated using the ultrasonic coating procedure of Example 5 and the parameters in Table 8 below. Table 9 also shows the amount of paclitaxel coated on each stent.

TABLE 9

Coating Parameters for Stents Coated with 2.34 mM Paclitaxel

| Coating Solution | 2.34 mM PTX in 88% MeOH/H$_2$O | | | |
|---|---|---|---|---|
| Stents | 1-3 | 4-6 | 7-9 | 10-12 |
| Relative Humidity (%) | 8.7-13.3 | 7.3-8.5 | 7.1-8.3 | 7.4-8.2 |
| Temperature (degrees F.) | 82.4-83.1 | 83.1 | 83.3-83.4 | 83.7-84.0 |
| Target Dose (micrograms) | 74 | | | |
| Actual Dose (micrograms) | 84 ± 5.89 | | | |
| Flow Rate (mL/min) | 0.03 | | | |
| Loops | 5 | | | |
| Air Shroud (psi) | 1.0 | | | |
| Linear Velocity (in/sec) | 0.025 | | | |
| Rotational Velocity (rpm) | 60 | | | |
| Oxygen Content (ppm) | 145-155 | | | |
| Power (Watts) | 0.8 | | | |
| Nozzle Distance from Stent (mm) | 8 | | | |

Figure 14:
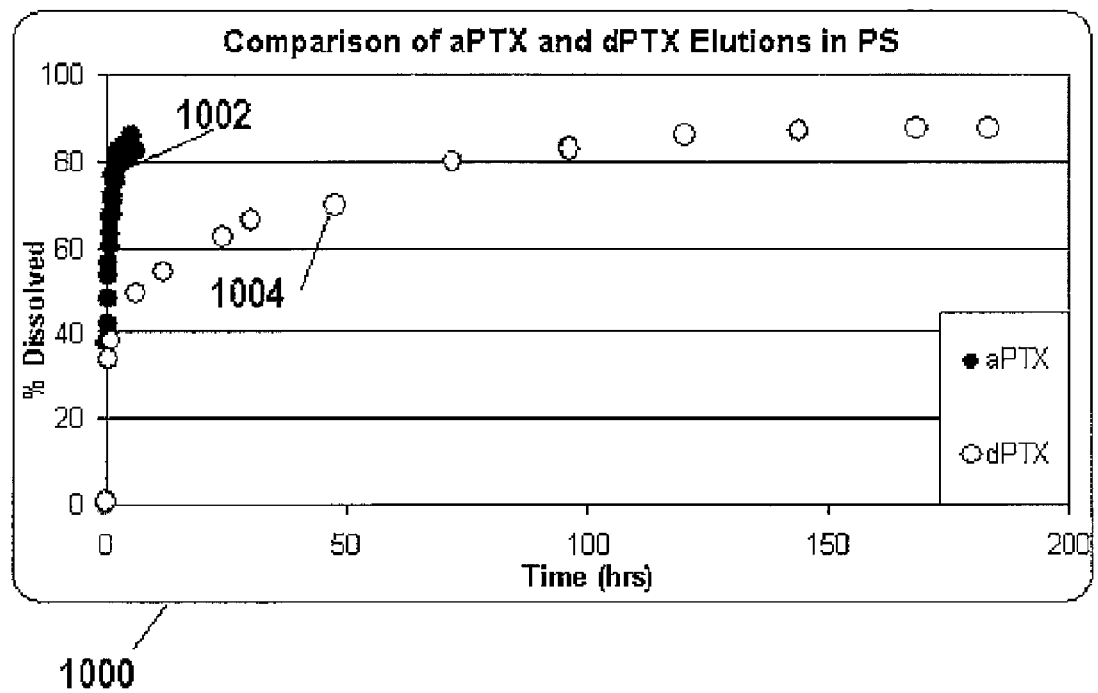
FIG. 14 is a graph showing the elution profiles of two different paclitaxel coated stents, described in Example 6.

FIG. 14 shows an elution graph 1000 comparing a first elution profile 1002 for a 100% amorphous paclitaxel coating (formed by spray coating an ethanol-paclitaxel according to Example 4B) compared to a second elution profile 1004 obtained as the average of the 12 stent coatings according to Table 8 (containing about 50% dihydrate paclitaxel) (both in porcine serum). Increasing the amount of dihydrate resulted in sustained release of the paclitaxel in the second elution profile 1004 compared to the first elution profile 1002. FIG. 14 was obtained from a coated vascular stent having an amorphous paclitaxel (1002) or a 50% dihydrate:50% amorphous paclitaxel coating (1004) obtained in separate experiments during the continuous flow of a porcine serum elution medium. The coatings did not comprise a polymer. The amount of paclitaxel in the elution medium was measured by UV absorption at 227 nm. The first elution profile 1002 shows substantially all of the amorphous paclitaxel eluting within less than about 5 hours. The second elution profile 1004 in porcine serum elution medium showed about 60% of the paclitaxel coating eluted after about 25 hours and about 80% of the paclitaxel coating eluted from the coating after 75 hours.

Example 7

Elution of Paclitaxel-Coated Stents in HCD

Stents with coatings consisting of paclitaxel taxane therapeutic agents in both the dihydrate solid form and in the amorphous form were prepared by spray coating a solution comprising various amounts of paclitaxel, methanol and water. First, a first coating solution of 4.68 mM paclitaxel solution in 100% ethanol was prepared with 19.96 mg paclitaxel in 5 mL ethanol. Second, a second solution of 4.68 mM paclitaxel in 93% methanol and 7% water (v) was made with a total volume of about 5 mL (19.99 mg paclitaxel). Five (5) 6×20 ZILVER (Cook Inc., Bloomington, Ind.) stents were spray coated with the first spray solution and five (5) more 6×20 ZILVER (Cook Inc., Bloomington, Ind.) stents were spray coated with the second spray solution. All coating was performed on the abluminal surface only using the ultrasonic coating procedure of Example 5 and the parameters in Table 10 below. Table 10 also shows the amount of paclitaxel coated on each stent. Coatings formed from the first solution (ethanol) contained 93% amorphous paclitaxel, 7% dihydrate paclitaxel; coatings formed from the second solution (methanol/water) contained about 82% dihydrate and 18% amorphous paclitaxel.

TABLE 10

Coating Parameters for Stents Coated with 4.68 mM Paclitaxel

| Coating Solvent | EtOH | | 93% MeOH/H$_2$O | |
|---|---|---|---|---|
| Stent #s | 100-102 | 103-105 | 200-202 | 203-205 |
| Temperature (degrees F.) | 79.2 | 79.4-79.5 | 78.3-79.0 | 77.2-78.1 |
| Oxygen Content (ppm) | 135-165 | 125-145 | 135-145 | 135-180 |
| Relative Humidity (%) | 0.0 | | 0.0-0.8 | 0.0 |
| Power (Watts) | 1.1 | | 0.8 | |
| Actual Dose (µg) | 195 ± 17 | | 301 ± 10 | |
| Flow Rate (mL/min) | 0.03 | | | |
| Loops | 7 | | | |
| Air Shroud (psi) | 1.0 | | | |
| Linear Velocity (in/sec) | 0.025 | | | |
| Rotational Velocity (rpm) | 60 | | | |
| Nozzle Distance from Stent (mm) | 8 | | | |
| Target Dose (µg) | 219 | | | |

Figure 15:
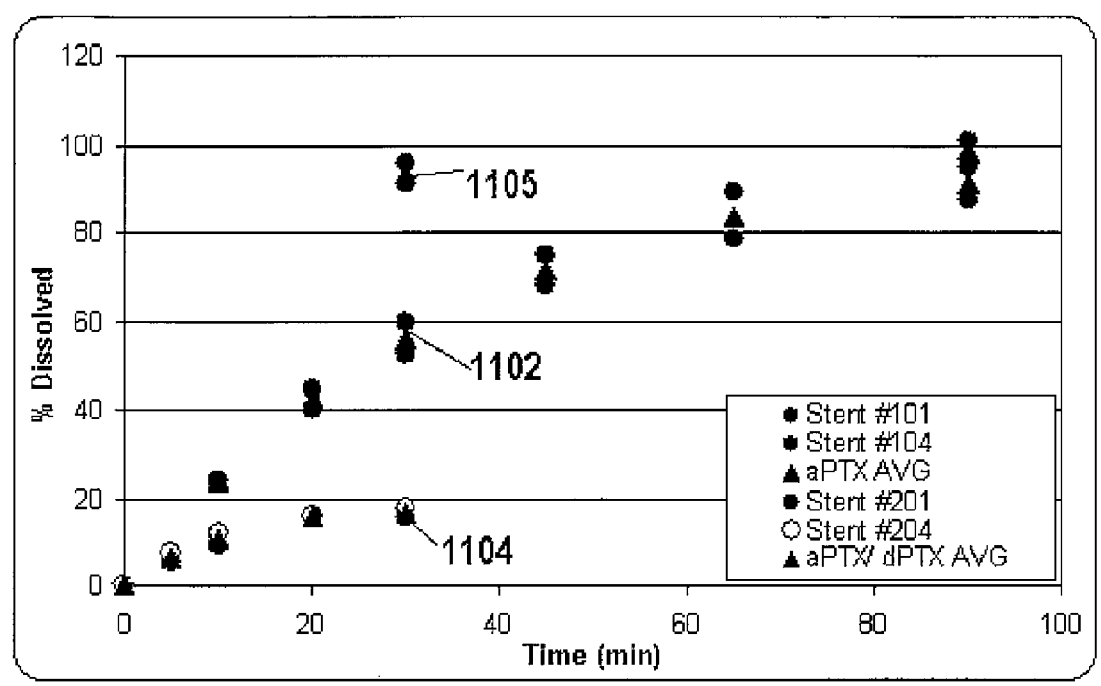
FIG. 15 is a graph showing the elution profiles from two different paclitaxel coated stents, described in Example 7.

FIG. 15 shows an elution graph 1100 obtained in a 0.5% aqueous HCD solution, comparing a first elution profile 1102 from the coatings formed from the 93% amorphous paclitaxel coating deposited from the first solution (formed by ultrasonic spray coating an according to Example 5, except as indicated in Example 7) compared to a second elution profile 1104 obtained from the stent coatings from the 82% dihydrate coating deposited from the second solution (formed by ultrasonic spray coating an according to Example 5, except as indicated in Example 7). The coatings did not comprise a polymer. The amount of paclitaxel in the elution medium was measured by UV absorption at 227 nm. The first elution profile 1102 shows a more rapid elution rate than the second elution profile 1104. Data points 1105 were obtained by contacting the coated stent formed from the second solution with 100% ethanol after obtaining the second elution profile 1104, resulting in rapid release of all remaining paclitaxel from the coating.

We claim:

1. A method of manufacturing a coated endolumenal medical device having at least one coated surface, the method comprising the steps of:
   applying a taxane therapeutic agent to at least one surface of an endolumenal medical device to form a coating of the taxane therapeutic agent on at least one surface of the endolumenal medical device; and
   conditioning the taxane therapeutic agent coating by maintaining the coating of the taxane therapeutic agent at a temperature and a relative humidity for a time period effective to decrease the solubility of the coating of the taxane therapeutic agent in a 0.5% w/w aqueous solution of Heptakis-(2,6-di-O-methyl)-β-cyclodextrin (HCD) elution medium at 25° C. for 24 hours.

2. The method of claim 1, wherein the coating includes a first weight percentage of a first solid form of the taxane therapeutic agent characterized by a vibrational spectrum having fewer than three peaks between 1735 and 1700 cm$^{-1}$ and a solubility of greater than 50% weight after 24 hours in porcine serum at 37° C.

3. The method of claim 2, wherein the conditioning of the taxane therapeutic agent coating is effective to decrease the first weight percentage and to provide a taxane therapeutic agent in a second taxane solid form having a second weight percentage within the coating, the second taxane solid form characterized by a vibrational spectrum comprising at least three peaks between 1735 and 1700 cm$^{-1}$ and a solubility of less than 40% weight after 24 hours in porcine serum at 37° C.

4. The method of claim 1, wherein the method further comprises the step of radially compressing the medical device after applying the taxane therapeutic agent coating and before conditioning the taxane therapeutic agent coating.

5. The method of claim 2, wherein the conditioning of the coating is performed by contacting the coated surface with an atmosphere having at least 90% humidity for a time effective to decrease the first weight percentage to less than about 50% of the coating.

6. The method of claim 2, wherein the taxane therapeutic agent is paclitaxel and the first solid form is amorphous paclitaxel.

7. The method of claim 3, wherein the taxane therapeutic agent is paclitaxel and the second solid form is dihydrate paclitaxel.

8. The method of claim 7, wherein the taxane therapeutic agent coating comprises a third weight percentage of the second solid form of the taxane therapeutic agent before conditioning, the third weight percentage being less than the second weight percentage.

9. The method of claim 8, wherein the first solid form is amorphous paclitaxel and the second solid form is dihydrate paclitaxel.

10. The method of claim 9, wherein the third weight percentage is less than about 25%.

11. The method of claim 10, wherein the second weight percentage is at least about 25% after conditioning of the coating.

12. The method of claim 3, wherein the medical device comprises a implantable frame configured as a radially expandable stent having a luminal surface and an abluminal surface, the coated surface is a portion of the abluminal surface of the stent, the coating comprises between 0.2 and 4 micrograms of the taxane therapeutic agent per mm$^2$ on the abluminal surface area of the stent, and the luminal surface has less than about less than about 0.10 microgram of the taxane therapeutic agent per mm$^2$ of luminal surface area.

13. The method of claim 12, wherein the first solid form is dihydrate paclitaxel and the second solid form is amorphous paclitaxel; and wherein the coating comprises at least 25% of the amorphous paclitaxel after the conditioning process.

14. The method of claim 13, wherein the coating comprises a first layer positioned between the at least one surface and a second layer, the first layer comprising the amorphous solid form and the second layer comprising the dihydrate solid form.

15. A method of manufacturing a coated medical device having a luminal surface and an abluminal surface and being moveable from a radially expanded configuration to a radially compressed configuration, the method comprising the steps of:
   applying paclitaxel to at least one surface of the medical device to form a paclitaxel coating on at least one of the luminal surface and the abluminal surface to form a paclitaxel coating attached to the at least one surface, the coating comprising a first weight percentage of paclitaxel in a hydrated solid form characterized by a vibrational spectrum comprising fewer than three peaks between 1740 and 1700 cm$^{-1}$ and a solubility of greater than 60% weight after 24 hours in a 0.5% w/w aqueous solution of Heptakis-(2,6-di-O-methyl)-β-cyclodextrin (HCD) elution medium at 25° C.;
   radially compressing the medical device with the paclitaxel coating attached to the at least one surface; and
   conditioning the paclitaxel coating at a humidity effective to decrease the first weight percentage and to provide a taxane therapeutic agent in a second taxane solid form within the coating, the second taxane solid form characterized by a vibrational spectrum at least three peaks between 1740 and 1700 cm$^{-1}$ and a solubility of less than 30% wt. after 24 hours in a 0.5% w/w aqueous solution of Heptakis-(2,6-di-O-methyl)-β-cyclodextrin (HCD) elution medium at 25° C.

16. The method of claim 15, wherein the paclitaxel coating is free of additional materials that change the elution of rate of the paclitaxel in 0.5% w/w aqueous solution of Heptakis-(2, 6-di-O-methyl)-β-cyclodextrin (HCD) elution medium at 25° C.

17. The method of claim 15, wherein the paclitaxel coating is conditioned at a temperature of about 30-60° C. and a relative humidity of 75-100% for a time period of 12-24 hours.

18. The method of claim 15, wherein the paclitaxel coating has a lower solubility of in the 0.5% w/w aqueous solution of Heptakis-(2,6-di-O-methyl)-β-cyclodextrin (HCD) elution medium at 25° C. after the conditioning step compare to the solubility of the paclitaxel coating in the 0.5% w/w aqueous solution of HCD elution medium at 25° C. before the conditioning step.

19. The method of claim 15, wherein the medical device is provided in the radially expanded configuration and the coating has a higher durability after the conditioning step than before the conditioning step, the durability being measured by the percentage weight reduction of the coating upon moving the coated medical device from the radially expanded configuration to the radially compressed radial configuration, and an increase in durability being measured by a decrease in the percentage weight reduction of the coating.

20. A method of manufacturing a coated stent having a luminal surface and an abluminal surface and being moveable from a radially expanded configuration to a radially compressed configuration, the method comprising the steps of:

applying paclitaxel to at least one surface of a radially expandable vascular stent to form a paclitaxel coating on at least one of the luminal surface and the abluminal surface of the vascular stent to form a paclitaxel coating attached to the at least one surface, the coating being free of additional materials that change the elution of rate of the paclitaxel in 0.5% w/w aqueous solution of Heptakis-(2,6-di-O-methyl)-β-cyclodextrin (HCD) elution medium at 25° C., the paclitaxel coating being free of a polymer that changes the elution rate of the paclitaxel in the HCD elution medium at 25° C.;

crimping the vascular stent having the paclitaxel coating attached to the at least one surface without reducing the weight of the coating by more than 10% wt to form a crimped vascular stent having a paclitaxel coating on at least one surface; and conditioning the paclitaxel coating on the crimped vascular stent at a temperature of about 30-60° C. and a relative humidity of 75-100% for a time period of 12-24 hours to form a conditioned paclitaxel coating that is less soluble in a 0.5% w/w aqueous solution of Heptakis-(2,6-di-O-methyl)-β-cyclodextrin (HCD) elution medium at 25° C. for 24 hours than the paclitaxel coating prior to conditioning.

* * * * *